US008389214B2

(12) United States Patent
Cervin et al.

(10) Patent No.: US 8,389,214 B2
(45) Date of Patent: *Mar. 5, 2013

(54) GLUCOSE TRANSPORT MUTANTS FOR PRODUCTION OF BIOMATERIAL

(75) Inventors: Marguerite A. Cervin, Redwood City, CA (US); Philippe Soucaille, Deyme (FR); Fernando Valle, Burlingame, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 767 days.

This patent is subject to a terminal disclaimer.

(21) Appl. No.: 11/971,341

(22) Filed: Jan. 9, 2008

(65) Prior Publication Data

US 2009/0142843 A1   Jun. 4, 2009

Related U.S. Application Data

(63) Continuation of application No. 10/728,337, filed on Oct. 3, 2003, now abandoned.

(51) Int. Cl.
    *C12Q 1/68*    (2006.01)
(52) U.S. Cl. ... 435/6.1; 435/471; 435/320.1; 435/252.3; 435/252.31; 435/252.33; 536/24.1
(58) Field of Classification Search .................. None
    See application file for complete search history.

(56) References Cited

U.S. PATENT DOCUMENTS

| | | | |
|---|---|---|---|
| 4,683,202 | A | 7/1987 | Mullis |
| 5,032,514 | A | 7/1991 | Anderson et al. |
| 5,168,056 | A | 12/1992 | Frost |
| 5,272,073 | A | 12/1993 | Frost et al. |
| 5,374,543 | A | 12/1994 | Murdock |
| 5,487,987 | A | 1/1996 | Frost et al. |
| 5,602,030 | A | 2/1997 | Ingrahm et al. |
| 5,629,181 | A | 5/1997 | Frost et al. |
| 5,776,736 | A | 7/1998 | Frost et al. |
| 5,985,617 | A | 11/1999 | Liao |
| 7,371,558 | B2 * | 5/2008 | Cervin et al. ............ 435/252.33 |

FOREIGN PATENT DOCUMENTS

| | | |
|---|---|---|
| WO | WO/87/01130 | 2/1987 |
| WO | WO 96/34961 | 11/1996 |
| WO | WO 98/07846 | 2/1998 |
| WO | WO 01/12833 | 2/2001 |
| WO | WO 03/089604 | 10/2003 |

OTHER PUBLICATIONS

U.S. Appl. No. 08/307,371, filed Sep. 16, 1994, Liao, J.C.
Altschul et al., "Gapped BLAST and PSI-BLAST: a new generation of protein database search programs," Nucl. Acids Res., 25(17):3389-3402, 1997.
Amann et al., "Vectors bearing a hybrid trp-lac promoter useful for regulated expression of cloned genes in *Escherichia coli*," *Gene*. Nov;25 (2-3):167-78, 1983.
Amore et al., "The fermentation of xylose—an analysis of the expression of *Bacillus* and *Actinoplanes* xylose isomerase genes in yeast," Appl. Microbiol. Biotech. 30:351-357, 1989.
*Arora et al., << Glucokinase of *Escherichia coli* : Induction in Response to the Stress of Overexpressing Foreign Proteins, *Archives of Biochemistry and Biophysics*, V. 319, N. 2, Jun. 1, pp. 574-578, 1995.
*Baez-Viveros, et al., Determination of 3-deoxy-D-arabino-heptulosonate 7-phosphate productivity and yield from glucose in *Escherinchia coli* devoid of the glucose phosphotransferease transport system, >> *Biotechnology and Bioengineering*, V. 73, N. 6, Jun. 20, 2001, pp. 530-535.
*Baez-Viveros, et al., << Metabolic engineering and protein directed evolution increase the yield of L-phenylalanine synthesized from glucose in *Escherichia coli*. >> Biotechnology and Bioengineering, V. 87, N. 4, Aug. 20, 2004, pp. 516-524.
Benthin, Stig et al. "Transport of Sugars via Two Anomer-Specific Sites on Mannose-Phosphotransferase System in *Lactococcus cremoris*: in Vivo Study of Mechanism, Kinetics, and Adaptation" Biotechnol. Bioeng. 42:440-448, 1993.
Bouvet et al., "Taxonomic Diversity of the D-Glucose Oxidation Pathway in the Enterobacteriacea" International Journal of Systematic Bacteriology, 39:61-67, 1989.
Bouvet et al., "Diversity of the phosphoenolpyruvate/glucose phosphotransferase system in the Enterobacteriaceae," *Ann Inst Pasteur Microbiol*. Jan.-Feb. 1987;138(1):3-13.
Burr et al., "DNA sequence elements located immediately upstream of the -10 hexamer in *Escherichia coli* promoters: a systematic study," *Nucleic Acids Res*. May 1, 2000;28(9):1864-70.
Carrier et al., "Controlling messenger RNA stability in bacteria: strategies for engineering gene expression," *Biotechnol Prog.* Nov.-Dec. 1997;13(6):669-708.
Chattopadhyay et al., "Azospirillum brasilense locus coding for phosphoenolpyruvate:fructose phosphotransferase system and global regulation of carbohydrate metabolilsm," *J Bacteriol.*; 175(10):3240-3, 1993.
Chen et al., "Sequence analysis of scrA and scrB from *Streptococcus sobrinus* 6715," *Infect Immun*.;61(6):2602-10, 1993.
Cocaign et al. "Batch kinetics of *Corynebacterium glutamicum* during growth on various carbon substrates: use of substrate mixtures to localize metabolic bottlenecks" Appl. Microbiol. and Biotechnol. 40:526-5301993.
Cordaro et al., "Fosfomycin resistance: selection method for internal and extended deletions of the phosphoenolpyruvate:sugar phosphotransferase genes of *Salmonella typhimurium*," *J Bacteriol.*; 128(3):785-93, 1976.
Curtis et al., "Phosphorylation of D-glucose in *Escherichia coli* mutants defective in glucosephosphotransferase, mannosephosphotransferase, and glucokinase," *J Bacteriol.*; 122(3):1189-99, 1975.
Datsenko et al., "One-step inactivation of chromosomal genes in *Escherichia coli* K-12 using PCR products," Proc. Natl. Acad. Sci 97:6640-6645, 2000.

(Continued)

*Primary Examiner* — Jim Ketter
(74) *Attorney, Agent, or Firm* — Danisco US Inc.

(57) ABSTRACT

A method is disclosed for restoring a Glu$^+$ phenotype to a PTS$^-$/Glu$^-$ bacterial cell which was originally capable of utilizing a phosphotransferase transport system (PTS) for carbohydrate transport. Bacterial cells comprising the Glu$^+$ phenotype have modified endogenous chromosomal regulatory regions which are operably linked to polynucleotides encoding galactose permeases and glucokinases.

44 Claims, 20 Drawing Sheets

OTHER PUBLICATIONS

Degnan et al., "Transport and metabolism of glucose and arabinose in *Bifidobacterium breve*," *Arch Microbiol.* 160(2):144-51 1993.

DeReuse et al.," the ptsH, ptsI, and crr Genes of the *Escherichia coli* Phosphoenolpyrubate-Dependent Phosphotransferase System: a complex Operon with Several Modes of Transcription" (1988) J. Bacteriol. 176:3827-3837.

Deuschle et al., "Promoters of *Escherichia coli*: a hierarchy of in vivo strength indicates alternate structures," EMBO J. 5: 2987-2994, 1986.

Erni et al., "Glucose-permease of the bacterial phosphotransferase system. Gene cloning, overproduction, and amino acid sequence of enzyme IIGIc," *J Biol Chem.*;261(35):16398-402 1986.

Erni et al., "The mannose permease of *Escherichia coli* consists of three different proteins. Amino acid sequence and function in sugar transport, sugar phosphorylation, and penetration of phage lambda DNA," *J Biol Chem.* 15;262(11):5238-47, 1987.

Ferenci T., "Adaptation to life at micromolar nutrient levels: the regulation of *Escherichia coli* glucose transport by endoinduction and cAMP," *FEMS Microbiol Rev.*;18(4):301-17, 1996.

Ferrari et al., in Harwood, *Bacillus*, "Genetics," Plenum Publishing Corporation, pp. 57-72, 1989.

*Flores et al., "Analysis of Carbon Metabolism in *Escherichia coli* Strains with an Inactive Phosphotransferase System by 13C Labeling and NMR Spectroscopy,"Met. Eng. 4:124-137, 2002.

*Flores et al., "Pathway engineering for the production of aromatic compounds in *Escherichia coli*," Nature Biotechnol. 14:620-623, 1996.

*Flores et al., << Adaptation for fast growth on glucose by differential expression of central carbon metabolism and gal regulon genes in an *Excherichia coli* strain lacking the phosphoenolpyruvate : carbohydrate phosphotransferease system, >> Metabolic Engineering, Academic Press, US, V. 7, Mar. 2005, pp. 70-87.

Fox et al., "Regulation of sugar transport by the bacterial phsophoenolpyruvate: glucose phosphotransferase system", Biochem. Soc. Trans. 12:155-157, 1984.

Gachelin, G., "A new assay of the phosphotransferase system in *Escherichia coli*," *Biochem Biophys Res Commun.*;34(4):382-7, 1969.

*Garcia-Alles et al., << The glucose-specific carrier of the *Escherichia coli* phosphotransferase system, >> Eur. J. Biochem. V. 269, 4969-4980 (2002) FEBS 2002.

Gosset, et al., << A direct comparison of approaches for increasing carbon flow to aromatic biosynthesis in *Escherichia coli*, >> J. of Industrial Microbiology S. for Industrila Micro., NL., V.17, N. 1, Jul. 1996, pp. 47-52.

Hawley, D.K et al., "Intermediates on the pathway to open-complex formation" Chapter 3: in: Promoters: Structure and Function.. Praeger Scientific. New York, 1982.

Henderson et al., "Homologous sugar proteins in *Escherichia coli* and their relatives in both prokaryotes and eukaryotes," *Philos Trans R Soc Lond B Biol Sci.*;326(1236):391-410, 1990.

*Hernandez-Montalvo V. et al., <<Characterization of sugar mixtures utilization by an *Excherichia coli* mutant devoid of the phosphotransferease system, : *Applied Microbiology and Biotechnology*, V.57, pp. 186-191 (Oct. 2001).

*Hernandez-Montalvo V. et al., <<Expression of galP and glk in a *Excherichia coli* PTS mutant restores glucose transport and increases glycolytic flux to fermentation products, >>: *Biotechnology and Bioengineering* V.83, N. 6, Sep. 20, 2003 pp. 687-694.

Hoess et al., "The role of the loxP spacer region in P1 site-specific recombination," *Nucleic Acids Res.*;14(5):2287-300, 1986.

Hogg et al., "Nucleotide sequence and analysis of the mgl operon of *Escherichia coli* K12," *Mol Gen Genet.*;229(3):453-9, Oct. 1991.

Holms, W.H., "The central metabolic pathways of *Escherichia coli*: Relationship between flux and control at a branch point, efficiency of conversion to biomass, and excretion of acetate", Curr. Top. Cell. Reg., vol. 28, pp. 69-105, 1986.

Huang et al., "A bacterial model system for chromosomal targeting" NAR. 19:443, 1991.

Huffman et al., "DNA-sequence asymmetry directs the alignment of recombination sites in the FLP synaptic complex,"*J Mol Biol.*;286 (1):1-13, 1999.

Iida et al., "Identification and characterization of tktB gene encoding a second transketolase in *Escherichia coli* K-12," *J Bacteriol.*; 175(17):5375-83, 1993.

*Jahreis et al., << Adaptation of Sucrose Metabolism in the *Escherichia coli* Wild-Type Strain EC3132, >> J. of Bacteriology, V. 184, N. 19, Oct. 2002, pp. 5307-5316.

Kilby et al., "Site-specific recombinases: tools for genome engineering" Trends Genet. 9:414-421, 1993.

Levy et al., "cyclic AMP synthesis in*Escherichia coli* strains bearing known deletions in the pts phosphotransferase operon" Gene 86:27-33, 1990.

Meadow et al. "The bacterial phosphoenol-pyruvate: Glycose phosphotransferase system" Annu. Rev. Biochem. 59:497-542, 1990.

Miller et al., "production of phenylanine and organic acids by phosphoenolypyrubate carboxylase-deficient mutants of *Escherichia coli*" J. Ind. Microbiol. 2:143-149, 1987.

Mitchell et al., "Identification of a phosphoenolpyruvate:fructose phosphotransferase system (fructose-1-phosphate forming) in *Listeria monocytogenes*," *J Bacteriol.*;175(9):2758-61, May 1993.

Mix-Wagner et al., "Recovery of potato apices after years of storage in liquid nitrogen," *Cryo Letters.*;24(1):33-41, 2003.

Mori et al., "Pyrubate Formation and Sugar Metabolism in an Amino Acid-Producing Bacterium, *Brevibacterium flavum*" Agric. Biol. Chem. 51:129-138, 1987.

Muller J. et al., "Repression of lac promoter as a function of distance, phase and quality of an auxiliary lac operator," *J Mol Biol.*;257(1):21-9, 1996.

Navas-Castillo et al. "Evidence for a phosphoenolpyruvate dependent sugar-phosphotransferase system in the mollicute *Acholeplasma florum*" Biochimie 75:675-679, 1993.

Nunes-Duby et al, "Similarities and differences among 105 members of the Int family of site-specific recombinases," *Nucleic Acids Res.*; 26(2):391-406, 1998.

Palmeros et al., "A family of removable cassettes designed to obtain antibiotic-resistance-free genomic modifications of *Escherichia coli* and other bacteria," Gene, 247: 255-264, 2000.

Pandey A, Production, purification and properties of microbial phytases, Bioresour Technol. 2001, 77(3):203-14.

Pearson et al., "Improved tools for biological sequence comparison," Proc. Natl. Acad. Sci., 85:2444-2448, 1988.

Postma et al., "Phosphoenolpyruvate: carbohydrate phosphotransferase system of bacteria," *Microbiol Rev.* Sep. 1985;49(3):232-69.

Postma et al., "Phosphoenolpyruvate: carbohydrate phosphotransferase systems of bacteria," *Microbiol Rev.*;57(3):543-94, 1993.

Postma P.W. Phosphotransferase System for Glucose and Other Sugars. In: Neidhardt et al., Eds. *Escherichia coli* and *Salmonella typhimurium*: Cellular and Molecular Biology. vol. 1. Washington, D.C. ASM Press pp. 127-141, 1996.

Romano et al., "Distribution of the phosphoenolpyruvate:glucose phosphotransferase system in fermentative bacteria," J Bacteriol.; 139(1):93-7, 1979.

Ruijter et al., "Analysis of mutations that uncouple transport from phosphorylation in enzyme IIGIc of the *Escherichia coli* phosphoenolpyruvate-dependent phosphotransferase system," *J Bacteriol.* :174(9):2843-50, 1992.

Russell et al., "Construction and analysis of in vivo activity of *E. coli* promoter hybrids and promoter mutants that alter the -35 to -10 spacing," Gene, 20: 231-243, 1982.

Saffen et al., "Sugar transport by the bacterial phosphotransferase system. Molecular cloning and structural analysis of the *Escherichia coli* ptsH, ptsI, and crr genes," *J Biol Chem.*;25;262(33):16241-53, 1987.

Saier et al., "Energetics of the Bacterial Phosphotransferase System in Sugar Transport and the Regulation of Carbon metabolism" In: Bacterial Energetics pp. 273-299, 1990.

Saier, Milton H., Jr., "Molecular Phylogeny as a Basis for the Classificaiton of Transport Proteins from Bacteria, Archea and Eukarya," *Advanced in Microbial Physiology*, Ed. R. K. Poole, Academic Press V40, pp. 81-136, 1998.

Sauer B. "Site-specific recombination: developments and applications" Curr. Opinions in Biotechnol. 5:521-527, 1994.

Silhavy, et al. "Experiments with gene fusions" In: Experiments with Gene Fusions, pp. 110-112, 1984.

Snoep et al., "Reconstruction of glucose uptake and phosphorylation in a glucose-negative mutant of *Escherichia coli* by using *Zymomonas mobilis* genes encoding the glucose facilitator protein and glucokinase," *J Bacteriol.*;176(7):2133-5, 1994.

Sommer et al., "T4 early promoter strength probed in vivo with unribosylated and ADP-ribosylated *Escherichia coli* RNA polymerase: a mutation analysis," Microbiol.146:2643-2653, 2000.

Sternberg et al., "Bacteriophage P1 site-specific recombination. I. Recombination between loxP sites," *J Mol Biol.* 25;150(4):467-86, 1981.

*Valle, et al., << Overexpression of chromosomal genes in *Escherichia coli*, >> Method in Molecular Biology (Clifton, N.J.), V. 267, 2004, pp. 113-122.

Weigel et al., "Sugar transport by the bacterial phosphotransferase system. Isolation and characterization of enzyme I from *Salmonella typhimurium*," *J Biol Chem.*;257(23):14461-9, 1982.

Wood, Noel R. et al. "Properties of cellulolytic enzyme systems", Biochem. Soc. Trans., vol. 13, pp. 407-410, 1985.

Yanisch-Perron et al. "Improved M13 phage cloning vectors and host strains: nucelotide sequences of the M13mp18 and pUC19 vectors", Gene 33:103-119, 1985.

Yoon, K-H et al., "Cloning and Characterization of the Gene Encoding Enzyme II of the *Brevibacterium lactofermentum* Phosphoenolpyruvate-Dependent Sugar Phosphotrasnferase System" Abstr. O-25 in 93rd Ann. Meet. Am. Soc. Microbiol., p. 323, 1993.

Yu et al., "Chemotaxis of the marine bacterium *Vibrio furnissii* to sugars. A potential mechanism for initiating the chitin catabolic cascade," *J Biol Chem.*;268(13):9405-9, 1993.

Zhu et al., "Homology requirements for ligation and strand exchange by the FLP recombinase," *J Biol Chem.*;270(19):11646-53, 1995.

*Database DNA, Accession No. D12473, *Escherichia coli* gene for transketolase, complete cds, Feb. 3, 1999.

* cited by examiner

TCGGTTTTCACAGTTGTTACATTTCTTTTCAGTAAAGTCTGGATGCATATGGCGGCCGC*ATAA*
*CTTCGTATAGCATACATTATACGAAGTTATCTA*GAGTTGCATGCCTGCAGGTCCGAATTTCTG
CCATTCATCCGCTTATTATCACTTATTCAGGCGTAGCACCAGGCGTTTAAGGGCACCAATAAC
TGCCTTAAAAAAA<u>TTACGCCCCGCCCTGCCACTCATCGCAGTACTGTTGTAATTCATTAAGCA</u>
<u>TTCTGCCGACATGGAAGCCATCACAAACGGCATGATGAACCTGAATCGCCAGCGGCATCAGCA</u>
<u>CCTTGTCGCCTTGCGTATAATATTTGCCCATGGTGAAAACGGGGGCGAAGAAGTTGTCCATAT</u>
<u>TGGCCACGTTTAAATCAAAACTGGTGAAACTCACCCAGGGATTGGCTGAGACGAAAACATAT</u>
<u>TCTCAATAAACCCTTTAGGGAAATAGGCCAGGTTTTCACCGTAACACGCCACATCTTGCGAAT</u>
<u>ATATGTGTAGAAACTGCCGGAAATCGTCGTGGTATTCACTCCAGAGCGATGAAAACGTTTCAG</u>
<u>TTTGCTCATGGAAAACGGTGTAACAAGGGTGAACACTATCCCATATCACCAGCTCACCGTCTT</u>
<u>TCATTGCCATACGGAATTCCGGATGAGCATTCATCAGGCGGGCAAGAATGTGAATAAAGGCCG</u>
<u>GATAAAACTTGTGCTTATTTTTCTTTACGGTCTTTAAAAAGGCCGTAATATCCAGCTGAACGG</u>
<u>TCTGGTTATAGGTACATTGAGCAACTGACTGAAATGCCTCAAAATGTTCTTTACGATGCCATT</u>
<u>GGGATATATCAACGGTGGTATATCCAGTGATTTTTTTCTCCAT</u>TTTAGCTTCCTTAGCTCCTG
AAAATCTCGATAACTCAAAAAATACGCCCGGTAGTGATCTTATTTCATTATGGTGAAAGTTGG
AACCTCTTACGTGCCGATCAACGTCTCATTTTCGCCAAAAGTTGGCCCAGGGCTTCCCGGTAT
CAACAGGGACACCAGGATTTATTTATTCTGCGAAGTGATCTTCCGTCACAGGTATTTATTCGG
ACTC*TAGATAACTTCGTATAGCATACATTATACGAAGTTAT*GGATCATGGCTGTGCAGGTCGT
AAATCACTGCATAATTCGTGTCGCTCAAGGCGCACTCCCGTTCTGGATAATGTTTTTGCGCC
GACATCATAACGGTTCTGGCAAATATTCTGAAATGAGCTG<u>TTGACA</u>ATTAATCATCCGGCTCG
<u>TATAAT</u>GTGTGG*AATTGTGAGCGGATAACAATTT*CACACAGGAAACAGACTAATTCACAATAA
AAAATAACCATATTGGAGGGCATCATG

FIG. 2

CAGCAGTGGTGGTGATCGGTTTTGGCTGGGGCCCCTCCCCGCACCGGAGGCCGATTACAGCCAA
CCACAACAGGCAAAGGGTTTGGAAGATATTCATATTATTATTGCGGTTGTCACAGTTGTTACAT
TTCTTTTCAGTAAAGTCTGGATG*CATATGGCGGCCGCATAACTTCGTATAGCATACATTATACG*
*AAGTTAT*GGATCATGGCTGTGCAGGTCGTAAATCACTGCATAATTGGTGTCGCTCAAGGCGCAC
TCCCGTTCTGGATAATGTTTTTTGCGCCGACATCATAACGGTTCTGGCAAATATTCTGAAATGA
GCTG<u>TTGACA</u>ATTAATCATCCGGCTCG<u>TATAAT</u>GTGTGGCATTG

FIG. 3

ACTTAGTTTGCCCAGCTTGCAAAAAGGCATCGCTGCAATTGGATGCATATGGCGGCCGC*ATAA*
*CTTCGTATAGCATACATTATACGAAGTTATCTA*GAGTTGCATGCCTGCAGGTCCGAATTTCTG
CCATTCATCCGCTTATTATCACTTATTCAGGCGTAGCACCAGGCGTTTAAGGGCACCAATAAC
TGCCTTAAAAAAA<u>TTACGCCCCGCCCTGCCACTCATCGCAGTACTGTTGTAATTCATTAAGCA</u>
<u>TTCTGCCGACATGGAAGCCATCACAAACGGCATGATGAACCTGAATCGCCAGCGGCATCAGCA</u>
<u>CCTTGTCGCCTTGCGTATAATATTTGCCCATGGTGAAAACGGGGGCGAAGAAGTTGTCCATAT</u>
<u>TGGCCACGTTTAAATCAAAACTGGTGAAACTCACCCAGGGATTGGCTGAGACGAAAAACATAT</u>
<u>TCTCAATAAACCCTTTAGGGAAATAGGCCAGGTTTTCACCGTAACACGCCACATCTTGCGAAT</u>
<u>ATATGTGTAGAAACTGCCGGAAATCGTCGTGGTATTCACTCCAGAGCGATGAAAACGTTTCAG</u>
<u>TTTGCTCATGGAAAACGGTGTAACAAGGGTGAACACTATCCCATATCACCAGCTCACCGTCTT</u>
<u>TCATTGCCATACGGAATTCCGGATGAGCATTCATCAGGCGGGCAAGAATGTGAATAAAGGCCG</u>
<u>GATAAAACTTGTGCTTATTTTTCTTTACGGTCTTTAAAAAGGCCGTAATATCCAGCTGAACGG</u>
<u>TCTGGTTATAGGTACATTGAGCAACTGACTGAAATGCCTCAAAATGTTCTTTACGATGCCATT</u>
<u>GGGATATATCAACGGTGGTATATCCAGTGATTTTTTCTCCAT</u>TTTAGCTTCCTTAGCTCCTG
AAAATCTCGATAACTCAAAAAATACGCCCGGTAGTGATCTTATTTCATTATGGTGAAAGTTGG
AACCTCTTACGTGCCGATCAACGTCTCATTTTCGCCAAAAGTTGGCCCAGGGCTTCCCGGTAT
CAACAGGGACACCAGGATTTATTTATTCTGCGAAGTGATCTTCCGTCACAGGTATTTATTCGG
ACTC*TAGATAACTTCGTATAGCATACATTATACGAAGTTAT*GGATCATGGCTGTGCAGGTCGT
AAATCACTGCATAATTCGTGTCGCTCAAGGCGCACTCCCGTTCTGGATAATGTTTTTGCGCC
GACATCATAACGGTTCTGGCAAATATTCTGAAATGAGCTG<u>CTTGAC</u>AATTAATCATCCGGCTC
G<u>TATAAT</u>GTGTGG*AATTGTGAGCGGATAACAATTT*CACACAGGAAACAGACGAGAAAGAATTA
TTTTGACTTTAGCGGAGCAGTTGAGAATG

*FIG. 4*

```
TAGTAAAGCCCTCGCTAGATTTTAATGCGGATGTTGCGATTACTTCGCCAACTATTGCGATAAC
AAGAAAAAGCCAGCCTTTCATGATATATCTCCCAATTTGTGTAGGGCTTATTATGCACGCTTAA
AAATAATAAAAGCAGACTTGACCTGATAGTTTGGCTGTGAGCAATTATGTGCTTAGTGCATCTA
ACGCTTGAGTTAAGCCGCGCCGCGAAGCGGCGTCGGCTTGAACGAATTGTTAGACATTATTTGC
CGACTACCTTGGTGATCTCGCCTTTCACGTAGTGGACAAATTCTTCCAACTGATCTGCGCGCGA
GGCCAAGCGATCTTCTTCTTGTCCAAGATAAGCCTGTCTAGCTTCAAGTATGACGGGCTGATAC
TGGGCCGGCAGGCGCTCCATTGCCCAGTCGGCAGCGACATCCTTCGGCGCGATTTTGCCGGTTA
CTGCGCTGTACCAAATGCGGGACAACGTAAGCACTACATTTCGCTCATCGCCAGCCCAGTCGGG
CGGCGAGTTCCATAGCGTTAAGGTTTCATTTAGCGCCTCAAATAGATCCTGTTCAGGAACCGGA
TCAAAGAGTTCCTCCGCCGCTGGACCTACCAAGGCAACGCTATGTTCTCTTGCTTTTGTCAGCA
AGATAGCCAGATCAATGTCGATCGTGGCTGGCTCGAAGATACCTGCAAGAATGTCATTGCGCTG
CCATTCTCCAAATTGCAGTTCGCGCTTAGCTGGATAACGCCACGGAATGATGTCGTCGTGCACA
ACAATGGTGACTTCTACAGCGCGGAGAATCTCGCTCTCTCCAGGGGAAGCCGAAGTTTCCAAAA
GGTCGTTGATCAAAGCTCGCCGCGTTGTTTCATCAAGCCTTACGGTCACCGTAACCAGCAAATC
AATATCACTGTGTGGCTTCAGGCCGCCATCCACTGCGGAGCCGTACAAATGTACGGCCAGCAAC
GTCGGTTCGAGATGGCGCTCGATGACGCCAACTACCTCTGATAGTTGAGTCGATACTTCGGCGA
TCACCGCTTCCCTCATGATGTTTAACTTTGTTTTAGGGCGACTGCCCTGCTGCGTAACATCGTT
GCTGCTCCATAACATCAAACATCGACCCACGGCGTAACGCGCTTGCTGCTTGGATGCCCGAGGC
ATAGACTGTACCCCAAAAAAACAGTCATAACAAGCCATGAAAACCGCCACTGCGCCGTTACCAC
CGCTGCGTTCGGTCAAGGTTCTGGACCAGTTGCGTGAGCGCATACGCTACTTGCATTACAGCTT
ACGAACCGAACAGGCTTATGTCCACTGGGTTCGTGCCTTCATCCGTTTCCACGGTGTGCGTCAC
CCGGCAACCTTGGGCAGCAGCGAAGTCGAGGCATTTCTGTCCTGGCTGGCGAACGAGCGCAAGG
TTTCGGTCTCCACGCATCGTCAGGCATTGGCGGCCTTGCTGTTCTTCTACGGCAAGGTGCTGTG
CACGGATCTGCCCTGGCTTCAGGAGATCGGAAGACCTCGGCCGTCGCGGCGCTTGCCGGTGGTG
CTGACCCCGGATGAAGTGGTTCGCATCCTCGGTTTTCTGGAAGGCGAGCATCGTTTGTTCGCCC
AGCTTCTGTATGGAACGGGCATGCGGATCAGTGAGGGTTTGCAACTGCGGGTCAAGGATCTGGA
TTTCGATCACGGCACGATCATCGTGCGGGAGGGCAAGGGCTCCAAGGATCGGGCCTTGATGTTA
CCCGAGAGCTTGGCACCCAGCCTGCGCGAGCAGGGGAATTAATTCCCACGGGTTTTGCTGCCCG
CAAACGGGCTGTTCTGGTGTTGCTAGTTTGTTATCAGAATCGCAGATCCGGCTTCAGCCGGTTT
GCCGGCTGAAAGCGCTATTTCTTCCAGAATTGCCATGATTTTTTCCCCACGGGAGGCGTCACTG
GCTCCCGTGTTGTCGGCAGCTTTGATTCGATAAGCAGCATCGCCTGTTTCAGGCTGTCTATGTG
TGACTGTTGAGCTGTAACAAGTTGTCTCAGGTGTTCAATTTCATGTTCTAGTTGCTTTGTTTTA
CTGGTTTCACCTGTTCTATTAGGTGTTACATGCTGTTCATCTGTTACATTGTCGATCTGTTCAT
GGTGAACAGCTTTGAATGCACCAAAAACTCGTAAAAGCTCTGATGTATCTATCTTTTTTACACC
GTTTTCATCTGTGCATATGGACAGTTTTCCCTTTGATATGTAACGGTGAACAGTTGTTCTACTT
TTGTTTGTTAGTCTTGATGCTTCACTGATAGATACAAGAGCCATAAGAACCTCAGATCCTTCCG
TATTTAGCCAGTATGTTCTCTAGTGTGGTTCGTTGTTTTGCGTGAGCCATGAGAACGAACCAT
TGAGATCATACTTACTTTGCATGTCACTCAAAATTTTGCCTCAAAACTGGTGAGCTGAATTTT
TGCAGTTAAAGCATCGTGTAGTGTTTTCTTAGTCCGTTATGTAGGTAGGAATCTGATGTAATG
GTTGTTGGTATTTTGTCACCATTCATTTTATCTGGTTGTTCTCAAGTTCGGTTACGAGATCCA
TTTGTCTATCTAGTTCAACTTGGAAAATCAACGTATCAGTCGGGCGGCCTCGCTTATCAACCAC
CAATTTCATATTGCTGTAAGTGTTTAAATCTTTACTTATTGGTTTCAAAACCCATTGGTTAAGC
CTTTTAAACTCATGGTAGTTATTTTCAAGCATTAACATGAACTTAAATTCATCAAGGCTAATCT
CTATATTTGCCTTGTGAGTTTTCTTTTGTGTTAGTTCTTTTAATAACCACTCATAAATCCTCAT
AGAGTATTTGTTTTCAAAAGACTTAACATGTTCCAGATTATATTTATGAATTTTTTTAACTGG
AAAAGATAAGGCAATATCTCTTCACTAAAAACTAATTCTAATTTTTCGCTTGAGAACTTGGCAT
```

FIG. 8A

```
AGTTTGTCCACTGGAAAATCTCAAAGCCTTTTAACCAAAGGATTCCTGATTTCCACAGTTCTCGT
CATCAGCTCTCTGGTTGCTTTAGCTAATACACCATAAGCATTTTCCCTACTGATGTTCATCATC
TGAGCGTATTGGTTATAAGTGAACGATACCGTCCGTTCTTTCCTTGTAGGGTTTTCAATCGTGG
GGTTGAGTAGTGCCACACAGCATAAAATTAGCTTGGTTTCATGCTCCGTTAAGTCATAGCGACT
AATCGCTAGTTCATTTGCTTTGAAAACAACTAATTCAGACATACATCTCAATTGGTCTAGGTGA
TTTTAATCACTATACCAATTGAGATGGGCTAGTCAATGATAATTACTAGTCCTTTTCCTTTGAG
TTGTGGGTATCTGTAAATTCTGCTAGACCTTTGCTGGAAAACTTGTAAATTCTGCTAGACCCTC
TGTAAATTCCGCTAGACCTTTGTGTGTTTTTTTGTTTATATTCAAGTGGTTATAATTTATAGA
ATAAAGAAGAATAAAAAAAGATAAAAAGAATAGATCCCAGCCCTGTGTATAACTCACTACTTT
AGTCAGTTCCGCAGTATTACAAAAGGATGTCGCAAACGCTGTTTGCTCCTCTACAAAACAGACC
TTAAAACCCTAAAGGCTTAAGTAGCACCCTCGCAAGCTCGGGCAAATCGCTGAATATTCCTTTT
GTCTCCGACCATCAGGCACCTGAGTCGCTGTCTTTTCGTGACATTCAGTTCGCTGCGCTCACG
GCTCTGGCAGTGAATGGGGGTAAATGGCACTACAGGCGCCTTTTATGGATTCATGCAAGGAAAC
TACCCATAATACAAGAAAAGCCCGTCACGGGCTTCTCAGGGCGTTTTATGGCGGGTCTGCTATG
TGGTGCTATCTGACTTTTTGCTGTTCAGCAGTTCCTGCCCTCTGATTTTCCAGTCTGACCACTT
CGGATTATCCCGTGACAGGTCATTCAGACTGGCTAATGCACCCAGTAAGGCAGCGGTATCATCA
ACAGGCTTACCCGTCTTACTGTCGGGAATTCATTTAAATAGTCAAAAGCCTCCGACCGGAGGCT
TTTGACTGCTAGGCGATCTGTGCTGTTTGCCACGGTATGCAGCACCAGCGCGAGATTATGGGCT
CGCACGCTCGACTGTCGGACGGGGGCACTGGAACGAGAAGTCAGGCGAGCCGTCACGCCCTTGA
CAATGCCACATCCTGAGCAAATAATTCAACCACTAAACAAATCAACCGCGTTTCCCGGAGGTAA
CCAAGCTTGCGGGAGAGAATGATGAACAAGAGCCAACAAGTTCAGACAATCACCCTGGCCGCCG
CCCAGCAAATGGCGGCGGCGGTGGAAAAAAAGCCACTGAGATCAACGTGGCGGTGGTGTTTTC
CGTAGTTGACCGCGGAGGCAACACGCTGCTTATCCAGCGGATGGACGAGGCCTTCGTCTCCAGC
TGCGATATTTCCCTGAATAAAGCCTGGAGCGCCTGCAGCCTGAAGCAAGGTACCCATGAAATTA
CGTCAGCGGTCCAGCCAGGACAATCTCTGTACGGTCTGCAGCTAACCAACCAACAGCGAATTAT
TATTTTTGGCGGCGGCCTGCCAGTTATTTTTAATGAGCAGGTAATTGGCGCCGTCGGCGTTAGC
GGCGGTACGGTCGAGCAGGATCAATTATTAGCCCAGTGCGCCCTGGATTGTTTTTCCGCATTAT
AACCTGAAGCGAGAAGGTATATTATGAGCTATCGTATGTTCCGCCAGGCATTCTGAGTGTTAAC
GAGGGGACCGTCATGTCGCTTTCACCGCCAGGCGTACGCCTGTTTTACGATCCGCGCGGGCACC
ATGCCGGCGCCATCAATGAGCTGTGCTGGGGCTGGAGGAGCAGGGGGTCCCCTGCCAGACCAT
AACCTATGACGGAGGCGGTGACGCCGCTGCGCTGGGCGCCCTGGCGGCCAGAAGCTCGCCCCTG
CGGGTGGGTATCGGGCTCAGCGCGTCCGGCGAGATAGCCCTCACTCATGCCCAGCTGCCGGCGG
ACGCGCCGCTGGCTACCGGACACGTCACCGATAGCGACGATCAACTGCGTACGCTCGGCGCCAA
CGCCGGGCAGCTGGTTAAAGTCCTGCCGTTAAGTGAGAGAAACTGAATGTATCGTATCTATACC
CGCACCGGGGATAAAGGCACCACCGCCCTGTACGGCGGCAGCCGCATCGAGAAGACCATATTC
GCGTCGAGGCCTACGGCACCGTCGATGAACTGATATCCCAGCTGGGCGTCTGCTACGCCACGAC
CCGCGACGCCGGGCTGCGGGAAAGCCTGCACCATATTCAGCAGACGCTGTTCGTGCTGGGGCT
GAACTGGCCAGCGATGCGCGGGCCTGACCCGCCTGAGCCAGACGATCGGCGAAGAGGAGATCA
CCGCCCTGGAGCGGCTTATCGACCGCAATATGGCCGAGAGCGGCCCGTTAAAACAGTTCGTGAT
CCCGGGGAGGAATCTCGCCTCTGCCCAGCTGCACGTGGCGCGCACCCAGTCCCGTCGGCTCGAA
CGCCTGCTGACGGCCATGGACCGCGCGCATCCGCTGCGCGACGCGCTCAAACGCTACAGCAATC
GCCTGTCGGATGCCCTGTTCTCCATGGCGCGAATCGAAGAGACTAGGCCTGATGCTTGCGCTTG
AACTGGCCTAGCAAACACAGAAAAAGCCCGCACCTGACAGTGCGGGCTTTTTTTTCCTAGGC
GATCTGTGCTGTTTGCCACGGTATGCAGCACCAGCGCGAGATTATGGGCTCGCACGCTCGACTG
TCGGACGGGGGCACTGGAACGAGAAGTCAGGCGAGCCGTCACGCCCTTGACAATGCCACATCCT
GAGCAAATAATTCAACCACTAAACAAATCAACCGCGTTTCCCGGAGGTAACCAAGCTTCACCTT
```

FIG. 8B

```
TTGAGCCGATGAACAATGAAAAGATCAAAACGATTTGCAGTACTGGCCCAGCGCCCCGTCAATC
AGGACGGGCTGATTGGCGAGTGGCCTGAAGAGGGGCTGATCGCCATGGACAGCCCCTTTGACCC
GGTCTCTTCAGTAAAAGTGGACAACGGTCTGATCGTCGAACTGGACGGCAAACGCCGGGACCAG
TTTGACATGATCGACCGATTTATCGCCGATTACGCGATCAACGTTGAGCGCACAGAGCAGGCAA
TGCGCCTGGAGGCGGTGGAAATAGCCCGTATGCTGGTGGATATTCACGTCAGCCGGGAGGAGAT
CATTGCCATCACTACCGCCATCACGCCGGCCAAAGCGGTCGAGGTGATGGCGCAGATGAACGTG
GTGGAGATGATGATGGCGCTGCAGAAGATGCGTGCCCGCCGGACCCCCTCCAACCAGTGCCACG
TCACCAATCTCAAAGATAATCCGGTGCAGATTGCCGCTGACGCCGCCGAGGCCGGGATCCGCGG
CTTCTCAGAACAGGAGACCACGGTCGGTATCGCGCGCTACGCGCCGTTTAACGCCCTGGCGCTG
TTGGTCGGTTCGCAGTGCGGCCGCCCCGGCGTGTTGACGCAGTGCTCGGTGGAAGAGGCCACCG
AGCTGGAGCTGGGCATGCGTGGCTTAACCAGCTACGCCGAGACGGTGTCGGTCTACGGCACCGA
AGCGGTATTTACCGACGGCGATGATACGCCGTGGTCAAAGGCGTTCCTCGCCTCGGCCTACGCC
TCCCGCGGGTTGAAAATGCGCTACACCTCCGGCACCGGATCCGAAGCGCTGATGGGCTATTCGG
AGAGCAAGTCGATGCTCTACCTCGAATCGCGCTGCATCTTCATTACTAAAGGCGCCGGGGTTCA
GGGACTGCAAAACGGCGCGGTGAGCTGTATCGGCATGACCGGCGCTGTGCCGTCGGGCATTCGG
GCGGTGCTGGCGGAAAACCTGATCGCCTCTATGCTCGACCTCGAAGTGGCGTCCGCCAACGACC
AGACTTTCTCCCACTCGGATATTCGCCGCACCGCGCGCACCCTGATGCAGATGCTGCCGGGCAC
CGACTTTATTTTCTCCGGCTACAGCGCGGTGCCGAACTACGACAACATGTTCGCCGGCTCGAAC
TTCGATGCGGAAGATTTTGATGATTACAACATCCTGCAGCGTGACCTGATGGTTGACGGCGGCC
TGCGTCCGGTGACCGAGGCGGAAACCATTGCCATTCGCCAGAAAGCGGCGCGGGCGATCCAGGC
GGTTTTCCGCGAGCTGGGGCTGCCGCCAATCGCCGACGAGGAGGTGGAGGCCGCCACCTACGCG
CACGGCAGCAACGAGATGCCGCCGCGTAACGTGGTGGAGGATCTGAGTGCGGTGGAAGAGATGA
TGAAGCGCAACATCACCGGCCTCGATATTGTCGGCGCGCTGAGCCGCAGCGGCTTTGAGGATAT
CGCCAGCAATATTCTCAATATGCTGCGCCAGCGGGTCACCGGCGATTACCTGCAGACCTCGGCC
ATTCTCGATCGGCAGTTCGAGGTGGTGAGTGCGGTCAACGACATCAATGACTATCAGGGGCCGG
GCACCGGCTATCGCATCTCTGCCGAACGCTGGGCGGAGATCAAAAATATTCCGGGCGTGGTTCA
GCCCGACACCATTGAATAAGGCGGTATTCCTGTGCAACAGACAACCCAAATTCAGCCCTCTTTT
ACCCTGAAAACCCGCGAGGGCGGGGTAGCTTCTGCCGATGAACGCGCCGATGAAGTGGTGATCG
GCGTCGGCCCTGCCTTCGATAAACACCAGCATCACACTCTGATCGATATGCCCCATGGCGCGAT
CCTCAAAGAGCTGATTGCCGGGGTGGAAGAAGAGGGGCTTCACGCCCGGGTGGTGCGCATTCTG
CGCACGTCCGACGTCTCCTTTATGGCCTGGGATGCGGCCAACCTGAGCGGCTCGGGGATCGGCA
TCGGTATCCAGTCGAAGGGGACCACGGTCATCCATCAGCGCGATCTGCTGCCGCTCAGCAACCT
GGAGCTGTTCTCCCAGGCGCCGCTGCTGACGCTGGAGACCTACCGGCAGATTGGCAAAAACGCT
GCGCGCTATGCGCGCAAAGAGTCACCTTCGCCGGTGCCGGTGGTGAACGATCAGATGGTGCGGC
CGAAATTTATGGCCAAAGCCGCGCTATTTCATATCAAAGAGACCAAACATGTGGTGCAGGACGC
CGAGCCCGTCACCCTGCACATCGACTTAGTAAGGGAGTGACCATGAGCGAGAAAACCATGCGCG
TGCAGGATTATCCGTTAGCCACCCGCTGCCCGGAGCATATCCTGACGCCTACCGGCAAACCATT
GACCGATATTACCCTCGAGAAGGTGCTCTCTGGCGAGGTGGGCCCGCAGGATGTGCGGATCTCC
CGCCAGACCCTTGAGTACCAGGCGCAGATTGCCGAGCAGATGCAGCGCCATGCGGTGGCGCGCA
ATTTCCGCCGCGCGGCGGAGCTTATCGCCATTCCTGACGAGCGCATTCTGGCTATCTATAACGC
GCTGCGCCCGTTCCGCTCCTCGCAGGCGGAGCTGCTGGCGATCGCCGACGAGCTGGAGCACACC
TGGCATGCGACAGTGAATGCCGCCTTTGTCCGGGAGTCGGCGGAAGTGTATCAGCAGCGGCATA
AGCTGCGTAAAGGAAGCTAAGCGGAGGTCAGCATGCCGTTAATAGCCGGGATTGATATCGGCAA
CGCCACCACCGAGGTGGCGCTGGCGTCCGACTACCCGCAGGCGAGGGCGTTTGTTGCCAGCGGG
ATCGTCGCGACGACGGGCATGAAAGGGACGCGGGACAATATCGCCGGGACCCTCGCCGCGCTGG
AGCAGGCCCTGGCGAAAACACCGTGGTCGATGAGCGATGTCTCTCGCATCTATCTTAACGAAGC
```

FIG. 8C

```
CGCGCCGGTGATTGGCGATGTGGCGATGGAGACCATCACCGAGACCATTATCACCGAATCGACC
ATGATCGGTCATAACCCGCAGACGCCGGGCGGGGTGGGCGTTGGCGTGGGGACGACTATCGCCC
TCGGGCGGCTGGCGACGCTGCCGGCGGCGCAGTATGCCGAGGGGTGGATCGTACTGATTGACGA
CGCCGTCGATTTCCTTGACGCCGTGTGGTGGCTCAATGAGGCGCTCGACCGGGGATCAACGTG
GTGGCGGCGATCCTCAAAAAGGACGACGGCGTGCTGGTGAACAACCGCCTGCGTAAAACCCTGC
CGGTGGTGGATGAAGTGACGCTGCTGGAGCAGGTCCCCGAGGGGTAATGGCGGCGGTGGAAGT
GGCCGCGCCGGGCCAGGTGGTGCGGATCCTGTCGAATCCCTACGGGATCGCCACCTTCTTCGGG
CTAAGCCCGGAAGAGACCCAGGCCATCGTCCCCATCGCCCGCGCCCTGATTGGCAACCGTTCCG
CGGTGGTGCTCAAGACCCCGCAGGGGATGTGCAGTCGCGGGTGATCCCGGCGGGCAACCTCTA
CATTAGCGGCGAAAAGCGCCGCGGAGAGGCCGATGTCGCCGAGGGCGCGGAAGCCATCATGCAG
GCGATGAGCGCCTGCGCTCCGGTACGCGACATCCGCGGCGAACCGGGCACCCACGCCGGCGGCA
TGCTTGAGCGGGTGCGCAAGGTAATGGCGTCCCTGACCGGCCATGAGATGAGCGCGATATACAT
CCAGGATCTGCTGGCGGTGGATACGTTTATTCCGCGCAAGGTGCAGGGCGGGATGGCCGGCGAG
TGCGCCATGGAGAATGCCGTCGGGATGGCGGCGATGGTGAAAGCGGATCGTCTGCAAATGCAGG
TTATCGCCCGCGAACTGAGCGCCCGACTGCAGACCGAGGTGGTGGTGGGCGGCGTGGAGGCCAA
CATGGCCATCGCCGGGGCGTTAACCACTCCCGGCTGTGCGGCGCCGCTGGCGATCCTCGACCTC
GGCGCCGGCTCGACGGATGCGGCGATCGTCAACGCGGAGGGGCAGATAACGGCGGTCCATCTCG
CCGGGGCGGGGAATATGGTCAGCCTGTTGATTAAAACCGAGCTGGGCCTCGAGGATCTTTCGCT
GGCGGAAGCGATAAAAAAATACCCGCTGGCCAAAGTGGAAAGCCTGTTCAGTATTCGTCACGAG
AATGGCGCGGTGGAGTTCTTTCGGGAAGCCCTCAGCCCGGCGGTGTTCGCCAAAGTGGTGTACA
TCAAGGAGGGCGAACTGGTGCCGATCGATAACGCCAGCCCGCTGGAAAAAATTCGTCTCGTGCG
CCGGCAGGCGAAAGAGAAAGTGTTTGTCACCAACTGCCTGCGCGCGCTGCGCCAGGTCTCACCC
GGCGGTTCCATTCGCGATATCGCCTTTGTGGTGCTGGTGGGCGGCTCATCGCTGGACTTTGAGA
TCCCGCAGCTTATCACGGAAGCCTTGTCGCACTATGGCGTGGTCGCCGGGCAGGGCAATATTCG
GGGAACAGAAGGGCCGCGCAATGCGGTCGCCACCGGGCTGCTACTGGCCGGTCAGGCGAATTAA
ACGGGCGCTCGCGCCAGCCTCTAGGTACAAATAAAAAAGGCACGTCAGATGACGTGCCTTTTTT
CTTGTCTAGAGTACTGGCGAAAGGGGATGTGCTGCAAGGCGATTAAGTTGGGTAACGCCAGGG
TTTTCCCAGTCACGACGTTGTAAAACGACGGCCAGTGAATTCGAGCTCGGTACCCGGGGCGGCC
GCGCTAGCGCCCGATCCAGCTGGAGTTTGTAGAAACGCAAAAAGGCCATCCGTCAGGATGGCCT
TCTGCTTAATTTGATGCCTGGCAGTTTATGGCGGGCGTCCTGCCCGCCACCCTCCGGGCCGTTG
CTTCGCAACGTTCAAATCCGCTCCCGGCGGATTTGTCCTACTCAGGAGAGCGTTCACCGACAAA
CAACAGATAAAACGAAAGGCCCAGTCTTTCGACTGAGCCTTTCGTTTTATTTGATGCCTGGCAG
TTCCCTACTCTCGCATGGGGAGACCCCACACTACCATCGGCGCTACGGCGTTTCACTTCTGAGT
TCGGCATGGGGTCAGGTGGGACCACCGCGCTACTGCCGCCAGGCAAATTCTGTTTTATCAGACC
GCTTCTGCGTTCTGATTTAATCTGTATCAGGCTGAAAATCTTCTCTCATCCGCCAAAACAGCCA
AGCTTGCATGCCTGCAGCCCGGGTTACCATTTCAACAGATCGTCCTTAGCATATAAGTAGTCGT
CAAAAATGAATTCAACTTCGTCTGTTTCGGCATTGTAGCCGCCAACTCTGATGGATTCGTGGTT
TTTGACAATGATGTCACAGCCTTTTTCCTTTAGGAAGTCCAAGTCGAAAGTAGTGGCAATACCA
ATGATCTTACAACCGGCGGCTTTTCCGGCGGCAATACCTGCTGGAGCGTCTTCAAATACTACTA
CCTTAGATTTGGAAGGGTCTTGCTCATTGATCGGATATCCTAAGCCATTCCTGCCCTTCAGATA
TGGTTCTGGATGAGGCTTACCCTGTTGACATCATTAGCGGTAATGAAGTACTTTGGTCTCCTG
ATTCCCAGATGCTCGAACCATTTTGTGCCATATCACGGGTACCGGAAGTTGCCACAGCCCATT
TCTCTTTTGGTAGAGCGTTCAAAGCGTTGCACAGCTTAACTGCACCTGGGACTTCAATGGATTT
TTCACCGTACTTGACCGGAATTTCAGCTTCTAATTTGTTAACATACTCTTCATTGGCAAAGTCT
GGAGCGAACTTAGCAATGGCATCAAACGTTCTCCAACCATGCGAGACTTGGATAACGTGTTCAG
CATCGAAATAAGGTTTGTCCTTACCGAAATCCCTCCAGAATGCAGCAATGGCTGGTTGAGAGAT
```

FIG. 8D

```
GATAATGGTACCGTCGACGTCGAACAAAGCGGCGTTAACTTTCAAAGATAGAGGTTTAGTAGTC
AATCCCATAATTCTAGTCTGTTTCCTGGATCCAATAAATCTAATCTTCATGTAGATCTAATTCT
TCAATCATGTCCGGCAGGTTCTTCATTGGGTAGTTGTTGTAAACGATTTGGTATACGGCTTCAA
ATAATGGGAAGTCTTCGACAGAGCCACATGTTTCCAACCATTCGTGAACTTCTTTGCAGGTAAT
TAAACCTTGAGCGGATTGGCCATTCAACAACTCCTTTTCACATTCCCAGGCGTCCTTACCAGAA
GTAGCCATTAGCCTAGCAACCTTGACGTTTCTACCACCAGCGCAGGTGGTGATCAAATCAGCAA
CACCAGCAGACTCTTGGTAGTATGTTTCTTCTAGATTCTGGGAAAAACATTTGACCGAATCT
GATGATCTCACCCAAACCGACTCTTTGGATGGCAGCAGAAGCGTTGTTACCCCAGCCTAGACCT
TCGACGAAACCACAACCTAAGGCAACAACGTTCTTCAAAGCACCACAGATGGAGATACCAGCAA
CATCTTCGATGACACTAACGTGGAAGTAAGGTCTGTGGAACAAGGCCTTTAGAACCTTATGGTC
GACGTCCTTGCCCTCGCCTCTGAAATCCTTTGGAATGTGGTAAGCAACTGTTGTTTCAGACCAG
TGTTCTTGAGCGACTTCGGTGGCAATGTTAGCACCAGATAGAGCACCACATTGAATACCTAGTT
CCTCAGTGATGTAAGAGGATAGCAATTGGACACCTTTAGCACCAACTTCAAAACCCTTTAGACA
GGAGATAGCTCTGACGTGTGAATCAACATGACCTTTCAATTGGCTACAGATACGGGCAAAAAT
TGATGTGGAATGTTGAAAACGATGATGTCGACATCCTTGACTGAATCAATCAAGTCTGGATTAG
CAACCAAATTGTCGGGTAGAGTGATGCCAGGCAAGTATTTCACGTTTTGATGTCTAGTATTTAT
GATTTCAGTCAATTTTTCACCATTGATCTCTTCTTCGAACACCCACATTTGTACTATTGGAGCG
AAAACTTCTGGGTATCCCTTACAATTTTCGGCAACCACCTTGGCAATAGTAGTACCCCAGTTAC
CAGATCCAATCACAGTAACCTTGAAAGGCTTTTCGGCAGCCTTCAAAGAAACAGAAGAGGAACT
TCTCTTTCTACCAGCATTCAAGTGGCCGGAAGTTAAGTTTAATCTATCAGCAGCAGCAGCCATG
GAATTGTCCTCCTTACTAGTCATGGTCTGTTTCCTGTGTGAAATTGTTATCCGCTCACAATTCC
ACACATTATACGAGCCGGATGATTAATTGTCAACAGCTCATTTCAGAATATTTGCCAGAACCGT
TATGATGTCGGCGCAAAAAACATTATCCAGAACGGGAGTGCGCCTTGAGCGACACGAATTATGC
AGTGATTTACGACCTGCACAGCCATACCACAGCTTCCGATGGCTGCCTGACGCCAGAAGCATTG
GTGCACGCTAGCCAGTACATTTAAATGGTACCCTCTAGTCAAGGCCTTAAGTGAGTCGTATTAC
GGACTGGCCGTCGTTTTACAACGTCGTGACTGGGAAAACCCTGGCGTTACCCAACTTAATCGCC
TTGCAGCACATCCCCCTTTCGCCAGCTGGCGTAATAGCGAAGAGGCCCGCACCGATCGCCCTTC
CCAACAGTTGCGCAGCCTGAATGGCGAATGGCGCCTGATGCGGTATTTTCTCCTTACGCATCTG
TGCGGTATTTCACACCGCATATGGTGCACTCTCAGTACAATCTGCTCTGATGCCGCATAGTTAA
GCCAGCCCCGACACCCGCCAACACCCGCTGACGAGCT
```

```
GCCGCTGAAAGGCCGGCGATTTTGGCATCACCTGCTCCACTGCCACCAACTGGATTGCCAACATGATCGTTGGGCAACGTTCCTGACCATGCTCAACACG    1500
CGGCGACTTTCCGGCCGCTAAAACCGTAGTGGACGAGGTGACGGTTGACCTTGACGTTGTACTAGCAACGCGGTTGCAAGGACTGGTACGAGTTGTGC
         Pro Leu Lys Gly Arg Asp Phe Gly Ile Thr Cys Ser Thr Ala Thr Asn Trp Ile Ala Asn Met Ile Val Gly Ala Thr Phe Leu Thr Met Leu Asn Thr
                                                                    galP CTGGGTAACGCCACAACCTTCTGGGTGTGTATGCGGCTACTGTTTATCCTGCTGAACGTACTGTTATCTCTGACATTGTGGCTGGTACCGGAAACCAAACACGTTTCGCTGG    1600
GACCCATTGCGGTGTGGAAGACCACACATACGCCGAGAGTTGCATGACAGGACGACTGTAACACCGACCATGGCCTTTGGTTTGTGCAAAGCGACC
     Leu Gly Asn Ala Asn Thr Phe Trp Val Tyr Ala Ala Leu Asn Val Leu Phe Ile Leu Leu Trp Leu Thr Leu Val Pro Glu Thr Lys His Val Ser Leu
                                                                    galP AACATATTGAACGTAATCTGATGAAACGTCGTAAACTGCGCGAAATAGGCGCTAAAGGTCGTAAACTGCGACGCTTTCCAGCATTTTGACGCTACTTTCCAGCTGCTAATTAGAGAGGGTTCGAAGGAGGTAGCGCCTCCTTTGGTGGA    1700
TTGTATAACTTGCATTAGACTACTTTGCTGCGCATTTGACGCTGTAATTAGAGAGGGTTCGAAGGAGGTAGCGCCTCCTTTGGTGGA .
     Glu His Ile Glu Arg Asn Leu Met Lys Gly Arg Lys Leu Arg Glu Ile Gly Ala His Asp                               galP CTTGCAGTCATCTTTTCTGCTCTATCCTCGCGCTAATCATATGACTAGATCTGCAGAATTCGCCCTTAAGGAAGCTGTGCACCATACCGACACGTCCA    1800
GAACGTCAGTAGTCAGTCAGTAGAAAAGAAGCGAGAGATAGGAGCGATTAGTATACTGATCTAGACGTCTTAAGCGGGAATTCCTTCGACACGTGGT
                                                   Trc promoter CGTAAATCACTGCATAATTCGTGTCGTCGCTCAAGGCGCACTCCCGTTCTGGATAATGTTTTTGGCGCCGACATCATATAAGCGGTTCTGCCAAAAATATTCTGAAAT    1900
GCATTTAGTGACGTATTAAGCACAGCAGCGAGTTCCGCGTGAGGCAAGCATTTAAACAACAAAAACGGCGGCTGTAGTATTGCCAAGACCGTTTATAAGACTTTA GAGCTGTTGACAATTAATCATCCGGCTCGTATAATGTGTGGAATTGTGAGCGGATAACAATTCACACAGGAAACAGACCATGACAAAGTATGCATTAGT    2000
CTCGACAACTGTTAATTAGTAGGCCGAGCATATTACACACCTTAACACTCGCCTATTGTTAAGTGTGTCCTTTGTGGTACTGTTTCATACGTAATCA
                                                                                     Met Thr Lys Tyr Ala Leu Val
                                                                                                       glk CGGTGATGTGGGCGGCACCAACGCACGTCTTGCTCTCTGTGATATTGCCAGTGGTGAAATCTCGCAGGCTAAGACCTATTCAGGGCTTGATTACCCCAGC    2100
GCCACTACACCCGCCGTGGTTGCGTGCAGAACGACGAGACACTAGAAGCGTCACCACTTTAGAGCGTCCGATTCTGGATAAGTCCCGAACTAATGGGGTCG
     Gly Asp Val Gly Gly Thr Asn Ala Arg Leu Ala Leu Cys Asp Ile Ala Ser Gly Glu Ile Ser Gln Ala Lys Thr Tyr Ser Gly Leu Asp Tyr Pro Ser
                                                            glk
```

*FIG. 14C*

```
CTCGAAGGGTCATTCGGCTTTATCTTGAAGAACATAAGGTCGAGGTGAAAGACGGCTGTATTGCCATCGCTTGCCCAATTACCGGTGACTGGGTGGGCGA  2200
GAGCTTGCGCAGTAAGCGCAAATAGAACTTCTTGTATTCCAGTCCACTACTTCTGCCGACATAACGGTCGAACGGGTTAATGCCACTGACCGACCGCT
Leu Glu Ala Val Ile Arg Val Tyr Leu Glu Glu His Lys Val Glu Val Lys Asp Gly Cys Ile Ala Ile Ala Cys Pro Ile Thr Gly Asp Trp Val Ala
                                                                                                    ──glk──

TGACCAACCATACCTGGGCGTTCTCAATTGCCGAAATGAAAAAGAATCTCGGTTTTAGCCATCTGGAAATTATTAACGATTTTACCGCTGTATCGATGGC  2300
ACTGGTTGGTATGGACCCGCAAGAGTTAACGGCTTTACTTTTCTTAGAGCCAAAATCGGTAGACCTTTAATAATTGCTAAAATGGCGACATAGCTACCG
Met Thr Asn His Thr Gly Phe Ile Ala Glu Met Lys Lys Asn Leu Gly Phe Ser His Leu Glu Ile Ile Asn Asp Phe Ala Val Ser Met Ala
                                                                                                    ──glk──

GAACCCGATGCTGAAAAAAGAGCATCTGATTCAGTTTGGTGGCGCAGAACCGGTCGAAGGTAAGCCTATTGCGGTTGCCGGAACCGGGCTTGGG  2400
CTTGGGCTACGACTTTTTTCTCGTAGACTAAGTCAAACCACCGCGTCTTGGCCAGCTTCCATTCGGATAACGCCAAATGCCACGGCTTGCCCGAACCC
Asn Pro Met Leu Lys Lys Glu His Leu Ile Gln Phe Gly Gly Ala Glu Pro Val Glu Gly Lys Pro Ile Ala Val Tyr Gly Ala Gly Thr Gly Leu Gly
                                                                                                    ──glk──

GTTGCGCATCTCGTCCATGTCGATAAGCGTTGGGTAAGCTTGCCAGGCAAGGGCGGTCACGTTGATTTTGCCGCCGAATAGTGAAGAAGAGGCCATTATCC  2500
CAACGCGTAGAGCAGGTACAGCTATTCGCAACCCATTCGAACGGTCCGCACCAGTGCAACTAAAACGGCGGCTTATCACTTCTTCTCCGGTAATAGG
Val Ala His Leu Val His Val Asp Lys Arg Trp Val Ser Leu Pro Gly Gly Gly His Val Asp Phe Ala Pro Asn Ser Glu Glu Ala Ile Ile
                                                                                                    ──glk──

TCGAAATATTGGCTGCGGAAATTGGTCATGTTTCGGCGGAGGCGTGCCTTTCTGGCCTGGTGAATTTGTATCGGCAATTGTGAAAGCTGACAA  2600
AGCTTTATAACGACGCCTTTAACCAGTACAAAGCCGCTCCGCACGGAAAGACCGGACCACTTAACATAGCCGTTAACACTTTCGACTGTT
Leu Glu Ile Leu Arg Ala Glu Ile Gly His Val Ser Ala Glu Ala Cys Leu Ser Gly Pro Gly Leu Val Asn Leu Tyr Arg Ala Ile Val Lys Ala Asp Asn
                                                                                                    ──glk──

CGGCCTGCCAGAAATCTCAAGCCAAAAGATATTACCGAACGCGCTGGCTGACAGCTGCACCGATTGCCGCCGCCGCATTGTCCGTGTTTGCGTCATT  2700
GGGGACGGTCTCTTTAGAGTTCGGTTTCTATAAATGGCTTGCGCGACCGACTGCGACGTGCTGACGTGGCTAACGCGGGCGCGTAACAGGCGACAAACGCAGTAA
Arg Leu Pro Glu Asn Leu Lys Pro Lys Asp Ile Thr Glu Arg Ala Ala Leu Ala Asp Ser Cys Thr Asp Cys Arg Arg Arg Ala Leu Ser Leu Phe Cys Val Ile
                                                                                                    ──glk──
```

FIG. 14D

ATGGGCCGTTTGCGGGCAATCTGGCGCTCAATCTCGGACACATTTGGGCGCGGTGTTTATTGGGGGCGGTATCGTGCCGGCGCTTCCTTGAGTTCTTCAAAG 2800
TACCCGGCAAAACCGCCGTTAGACCGCGAGTTAGAGCCCTGTAAACCGCCGCCACAATAACGCCCGCCATAGCACGGCGAAGGAACTCAAGAAGTTC
Met Gly Arg Phe Gly Gly Asn Leu Ala Leu Asn Leu Gly Thr Phe Gly Gly Val Phe Ile Ala Gly Gly Ile Val Pro Arg Phe Leu Glu Phe Lys
<u>────────────────────────────────────────────────────────────────────── glk ──</u>

GCTCCGGGTTTCCGTGCCGGCATTTGAAGATAAAGGGCGCTTTAAAGAATAAAGGGGCGCTTTAAAGAATATGTCCATGATATATTCCGGTGTATCTCATCGTCATCGTCCATGACAATCCGGGCCTTCT 2900
CGAGGCCAAAGGCACGGCCGTAAACTTCTATTTCCCGCGAATTCTTATAAGGCCACATAGAGTAGCAGTAGCAGTACTGTTAGGCCCGGAAGA
Gly Ser Gly Phe Arg Ala Ala Phe Glu Asp Lys Gly Arg Phe Lys Glu Tyr Val His Asp Ile Pro Val Tyr Leu Ile Val His Asp Asn Pro Gly Leu Leu
<u>────────────────────────────────────────────────────────────────────── glk ──</u>

CGGTTCCGGTGCACATTACGCCAGACCTTAGGTCACATTCTGTAAATCCTTCCTTTATATCGGGAGGTAACTCTCCGATAATCTTTAAATCATACA 3000
GCCAAGGCCACGTGTAAATGGCGGTCTGGAATCCAGTGTCCAGTGAAGACATTTAGGAAGGAAAATAGCCCTCCATTGAGAGGGCTATTAGAAATTTAGTATGT
Gly Ser Gly Ala His Leu Arg Gln Thr Leu Gly His Ile Leu •
<u>────────────────────── glk ──</u>

GTTTATTCAATTTTTCTTTGTGTCCCCTCACAAGGTCGAC 3040
CAAATAAGTTAAAAGAAACACAGGGGAGTGTTCCAGCTG

*FIG. 14E*

GLUCOSE TRANSPORT MUTANTS FOR PRODUCTION OF BIOMATERIAL

CROSS-REFERENCE TO RELATED APPLICATIONS

This application is a continuation application of application Ser. No. 10/728,337, filed Dec. 3, 2003, now abandoned, and claims priority to application PCT/US03/31,544, filed Oct. 3, 2003, U.S. Provisional Application No. 60/416,166 filed Oct. 4, 2002 and U.S. Provisional Application No. 60/374,931 filed Oct. 4, 2002, which are hereby incorporated by reference.

TECHNICAL FIELD

The present invention relates to genetically engineering metabolic pathways in bacterial host cells and provides methods and systems for the production of desired products in the engineered host cells. In particular, the invention relates to the enhancement of glucose transport in host strains, which were originally capable of using a phosphoenolpyruvate (PEP): phosphotransferase transport system (PTS) for glucose transport, by reducing PTS phosphoenolpyruvate (PEP) consumption and redirecting PEP or PEP precursors into a desired metabolic pathway, such as the common aromatic amino acid pathway.

BACKGROUND ART

Many industrially important microorganisms use glucose as their main carbon source to produce biosynthetic products. Therefore, cost-effective and efficient biosynthetic production of these products require that a carbon source, such as glucose be converted to said products at a high percentage yield. To meet this need, it would be advantageous to increase the influx of carbon sources into and through various metabolic pathways, such as the common aromatic pathway, the tricarboxylic acid (TCA) pathway, and the anaplerotic oxaloacetate synthetic pathway.

In the initial stage of host cell carbohydrate metabolism, each glucose molecule is converted to two molecules of phosphoenolpyruvate (PEP) in the cytosol. PEP is one of the major metabolic building blocks that cells use in their biosynthetic as routes. For example, PEP may be further converted to pyruvate and chemical reactions that convert glucose to pyruvate are referred to as the Embden-Meyerhoff pathway. All of the metabolic intermediates between the initial glucose carbohydrate and the final product, pyruvate, are phosphorylated compounds. Bacteria, which ferment glucose through the Embden-Meyerhof pathway, such as members of *Enterobacteriacea* and *Vibrionaceae*, are described in Bouvet et al., (1989) *International Journal of Systematic Bacteriology*, 39:61-67. Pyruvate may then by metabolized to yield products such as lactate, ethanol, formate, acetate and acetyl CoA. (See FIGS. 1A and 1B).

In addition to the Embden-Meyerhof pathway, many bacteria posses an active transport system known as the phosphoenolpyruvate (PEP)—dependent phosphotransferase transport system (PTS). This system couples the transport of a carbon source, such as glucose to its phosphorylation. The phosphoryl group is transferred sequentially from PEP to enzyme I and from enzyme I to protein HPr. The actual translocation step is catalyzed by a family of membrane bound enzymes (called enzyme II), each of which is specific for one or a few carbon sources. Reference is made to Postma et al., (1993) Phosphoenolpyruvate: Carbohydrate Phosphotransferase Systems in Bacteria, *Microbiol. Reviews.* 57:543-594 and Postma P. W. (1996) Phosphotransferase System for Glucose and Other Sugars. In: Neidhardt et al., Eds. *Escherichia coli* AND *Salmonella typhimurium*: CELLULAR AND MOLECULAR BIOLOGY. Vol. 1. Washington, D.C. ASM Press pp 127-141. However, due to the fact that PTS metabolizes PEP to phosphorylate the carbon source, the PTS system decreases the efficiency of carbon substrate conversion to a desired product. In glycolysis, two molecules of PEP are formed for every molecule of glucose catabolized. However, one molecule of PEP is required for PTS to function, leaving only one molecule of PEP available for other biosynthetic reactions.

Due to the role of PEP as a central metabolite, numerous approaches have been utilized to increase PEP supply in the cell and some of these are listed below:

a) eliminating pyruvate kinase activity by producing pyk mutants. Pyruvate kinase catalyzes the conversion of PEP to pyruvate. (Mori et al., (1987) *Agric. Biol. Chem.* 51:129-138);

b) eliminating PEP carboxylase activity by producing ppc mutants. PEP carboxylase catalyzes the conversion of PEP to oxaloacetate. (Miller et al., (1987) *J. Ind. Microbiol.* 2:143-149);

c) amplifying the expression of pps which encodes PEP synthase. PEP synthase catalyzes the conversion of pyruvate to PEP (U.S. Ser. No. 08/307,371); and d) increasing the supply of D-erythrose-4-phosphate (E4P) by for example overexpression of a transketolase gene (tktA or tktB) (U.S. Pat. No. 5,168,056) or overexpression of the transaldolase gene (talA) (Iida et al., (1983) *J. Bacteriol.* 175:5375-5383). Transketolase catalyzes the conversion of D-fructose-6-phosphate to E4P and transaldolase catalyzes the conversion of D-sedoheptulose-7-phosphate plus glyceraldehyde-3-phosphate to E4P plus fructose-6-phophate.

In addition to the above listed approaches, researchers have looked at methods of decreasing PTS:PEP dependent consumption by eliminating or modifying the function of the PTS. This approach is also attractive because PEP is twice as energetic as ATP. Many of these efforts focus on using an inactive PTS system. Examples of studies manipulating the PTS system include a) restoring a glucose phenotype (Glu$^+$) in PTS inactivated *E. coli* cells by introducing the genes glf and glk which encode a glucose-facilitated diffusion protein and glucokinase, respectively, from *Zymomonas mobilis*, wherein the *E. coli* cells have an inactivated PTS due to a deletion of the pstHIcrr operon (U.S. Pat. No. 5,602,030 and Snoep et al., (1994) *J. Bact.* 176:2133-2135) and b) subjecting PTS$^-$/Glu$^-$ *E. coli* strains to continuous culture selection on glucose and obtaining Glu+ revertants (PTS$^-$/Glu$^+$) with the capacity to obtain growth rates similar or higher than that of wild-type PTS$^-$/Glu$^-$ strains. (Flores et al., (2002) *Metab. Eng* 4:124-137; Flores et al., (1996) *Nature Biotechnol.* 14:620-623 and WO96/34961).

However, these approaches have various limitations. In general, the use of heterologous genes does not always work efficiently in new hosts. Additionally, membrane proteins, such as a glucose-facilitated diffusion protein, are usually intimately associated with lipids in the cell membrane and these can vary from species to species. Introduced soluble proteins such as glucokinase, may be subject to protease degradation. Further the use of spontaneous mutations in a cell to regain a phenotype can have unpredictable outcomes, and for industrial processes it is desirable to use completely characterized strains.

Contrary to the methods previously described, the present invention increases carbon flow to metabolic pathways in bacterial strains capable of transporting glucose without consuming PEP during the process. The conserved PEP or PEP precursors can then be redirected into a given metabolic pathway for enhanced production of a desired product. These strains are generated in cells having an inactivated PEP-dependent PTS by modifying an endogenous chromosomal regulatory region that is operably linked to a glucose assimilation protein and more specifically to a glucose transporter and/or a glucose phosphorylating protein, to restore or re-attain the ability of the cell to use glucose as a carbon source while maintaining an inactivated PTS. These cells are designated $PTS^-/Glu^+$.

SUMMARY OF THE INVENTION

Accordingly, there is provided by the present invention a method for increasing carbon flow into a metabolic pathway of a bacterial host cell wherein the host cell was originally capable of utilizing a PTS for carbohydrate transport. The method comprises selecting a bacterial host cell which is phenotypically $PTS^-/Glu^-$ and modifying an endogenous chromosomal regulatory region which is operably linked to a nucleic acid encoding a polypeptide involved in glucose assimilation to restore the $Glu^+$ phenotype.

In a first aspect, the invention pertains to a method of increasing carbon flow into a metabolic pathway of a $PTS^-/Glu^-$ bacterial host cell which was originally capable of utilizing a phosphotransferase transport system (PTS) for carbohydrate transport which comprises a) modifying an endogenous chromosomal regulatory region which is operably linked to a nucleic acid encoding a glucose assimilation protein in a $PTS^-/Glu^-$ host cell by transforming the $PTS^-/Glu^-$ host cell with a DNA construct comprising a promoter and DNA flanking sequences corresponding to upstream (5') regions of the glucose assimilation protein; b) allowing integration of the DNA construct to restore a Glu+ phenotype; and c) culturing the transformed host cell under suitable culture conditions, wherein the carbon flow into a metabolic pathway of the transformed host cell is increased compared to the carbon flow into the same metabolic pathway in a corresponding PTS bacterial host cell cultured under essentially the same culture conditions. In one embodiment of the method the promoter is a non-host cell promoter or a modified endogenous promoter. In a second embodiment the glucose assimilation protein is a glucose transporter, preferably a galactose permease obtained from *E. coli* or a glucose transporter having at least 80% sequence identity thereto. In a third embodiment the glucose assimilation protein is a phosphorylating protein, preferably a glucokinase obtained from *E. coli* or a glucokinase having at least 80% sequence identity thereto. In a fourth embodiment of the method the bacterial host cell is selected from the group consisting of *E. coli* cells, *Bacillus* cells and *Pantoea* cells. In a fifth embodiment, the $PTS^-/Glu^-$ host cell is obtained from a PTS cell by deletion of one or more genes selected from the group consisting of ptsI, ptsH and crr. In a sixth embodiment, the $PTS^-/Glu^+$ host cell is transformed with a polynucleotide encoding a protein selected from the group consisting of a transketolase, a transaldolase, a phosphoenolpyruvate synthase, DAHP syntheses DHQ synthase, DHQ dehydratase, shikimate dehydrogenase, shikimate kinase EPSP synthase and chorismate synthase.

In a second aspect, the invention pertains to a method as described in the first aspect and further comprising modifying an endogenous chromosomal regulatory region which is operably linked to a nucleic acid encoding a glucokinase in the $PTS^-/Glu^-$ host cell by transforming the $PTS^-/Glu^-$ host cell with a second DNA construct comprising a promoter and DNA flanking sequences corresponding to upstream (5') regions of the glucokinase.

In a third aspect, the invention pertains to a method for increasing the production of a desired product in a $PTS^-/Glu^-$ bacterial host cell originally capable of utilizing a PTS for carbohydrate transport which comprises a) transforming a bacterial host cell having a $PTS^-/Glu^-$ phenotype with a DNA construct comprising a promoter, wherein said DNA construct is chromosomally integrated into the $PTS^-/Glu^-$ host cell replacing an endogenous promoter which is operably linked to a nucleic acid encoding a glucose assimilation protein; b) culturing the transformed bacterial host cell under suitable conditions; c) allowing expression of the glucose assimilation protein to obtain a host cell having a $PTS^-/Glu^+$ phenotype, and d) obtaining an increased amount of a desired product in the transformed bacterial host cell compared to the amount of the desired product produced in a corresponding PTS bacterial cell cultured under essentially the same culture conditions, wherein said desired product is selected from the group consisting of pyruvate, PEP, lactate, acetate, glycerol, succinate, ethanol and chorismate. In one embodiment the host cell is selected from the group consisting of *E. coli* cells, *Bacillus* cells and *Pantoea* cells. In a second embodiment the glucose assimilation protein is a galactose permease obtained from *E. coli* or a glucose transporter having at least 80% sequence identity thereto. In a third embodiment, the glucose assimilation protein is a glucokinase obtained from *E. coli* or a glucokinase having at least 70% sequence identity thereto.

In a fourth aspect, the invention pertains to a method of increasing carbon flow into a metabolic pathway of a $PTS^-/Glu^-$ bacterial host cell originally capable of utilizing a phosphotransferase transport system (PTS) for carbohydrate transport which comprises a) modifying an endogenous chromosomal regulatory region which is operably linked to a nucleic acid encoding a galactose permease in a $PTS^-/Glu^-$ host cell by transforming the $PTS^-/Glu^-$ host cell with a first DNA construct comprising a promoter and DNA flanking sequences corresponding to upstream (5') regions of the galactose permease; b) modifying an endogenous chromosomal regulatory region which is operably linked to a nucleic acid encoding a glucokinase in the $PTS^-/Glu^-$ host cell by transforming the $PTS^-/Glu^-$ host cell with a second DNA construct comprising a promoter and DNA flanking sequences corresponding to upstream (5') regions of the glucokinase; c) allowing integration of the first and the second DNA constructs, wherein the first DNA construct replaces an endogenous promoter of the nucleic acid encoding the galactose permease and the second DNA construct replaces an endogenous promoter of the nucleic acid encoding the glucokinase wherein both the galactose permease and the glucokinase are expressed in the host cell and wherein said expression results in an increase in carbon flow into a metabolic pathway of the transformed host cell compared to carbon flow into the same metabolic pathway in the corresponding unaltered $PTS^-/Glu^-$ bacterial cell. In one embodiment the metabolic pathway is the common aromatic pathway. In a second embodiment the method further comprises transforming the $PTS^-/Glu^-$ host cell with a polynucleotide encoding a protein selected from the group consisting of a transketolase, a transaldolase and a phosphoenolpyruvate synthase.

In a fifth aspect, the invention pertains to a method of restoring a Glu+ phenotype to a $PTS^-/Glu^-$ bacterial host cell which was originally capable of utilizing a phosphotransferase transport system (PTS) for carbohydrate transport which comprises a) modifying an endogenous chromosomal regulatory region which is operably linked to a nucleic acid encoding a glucose transporter in a PTS⁻/Glu⁻ host cell by transforming the PTS⁻/Glu⁻ host cell with a first DNA construct comprising a promoter and DNA flanking sequences corresponding to upstream (5') regions of the glucose transporter; b) allowing integration of the first DNA construct, wherein the first DNA construct replaces an endogenous promoter of the nucleic acid encoding the glucose transporter; and c) allowing expression of the glucose transporter, wherein said expression restores a Glu+ phenotype to the PTS⁻/Glu⁻ host cell. In a preferred embodiment the method according to this aspect further comprises modifying an endogenous chromosomal regulatory region which is operably linked to a nucleic acid encoding a glucokinase in the PTS⁻/Glu⁻ host cell by transforming the PTS⁻/Glu⁻ host cell with a second DNA construct comprising an exogenous promoter and DNA flanking sequences corresponding to upstream (5') regions of the glucokinase; allowing integration of the second DNA construct wherein the second DNA construct replaces an endogenous promoter of the nucleic acid encoding the glucokinase; and allowing expression of the glucokinase. In one embodiment the restored Glu⁺ cells have a specific growth rate of at least about 0.4 hr⁻¹. In another embodiment the glucose transporter is a galactose permease.

In a sixth aspect the invention pertains to a method of increasing phosphoenolpyruvate (PEP) availability in a bacterial host cell which comprises a) selecting a bacterial host cell having a PTS⁻/Glu⁻ phenotype, wherein the bacterial host was originally capable of utilizing a phosphotransferase transport system (PTS) for carbohydrate transport; b) modifying an endogenous chromosomal regulatory sequence of the selected bacterial host cell comprising transforming said selected bacterial host cell with a DNA construct comprising a promoter, wherein said DNA construct is chromosomally integrated into the selected bacterial host cell replacing an endogenous promoter which is operably linked to a nucleic acid encoding a glucose assimilation protein; c) culturing the transformed bacterial host cell under suitable conditions; and d) allowing expression of the glucose assimilation protein to obtain an altered host cell having a PTS⁻/Glu⁺ phenotype, wherein the PEP availability is increased compared to the PEP availability in a corresponding unaltered PTS bacterial host cell cultured under essentially the same culture is conditions. In one embodiment the glucose assimilation protein is a galactose permease and the DNA construct comprises an exogenous promoter which replaces the endogenous promoter of the galactose permease. In another embodiment the glucose assimilation protein is a glucokinase and the DNA construct comprises an exogenous promoter which replaces the endogenous promoter of a glucokinase.

In an eighth aspect, the invention pertains to a method for increasing the growth rate of a PTS⁻/Glu⁻ bacterial host cell originally capable of utilizing a phosphotransferase transport system (PTS) for carbohydrate transport which comprises, a) modifying an endogenous chromosomal regulatory region which is operably linked to a nucleic acid encoding a galactose permease in a PTS⁻/Glu⁻ host cell by transforming the PTS⁻/Glu⁻ host cell with a first DNA construct comprising an exogenous promoter and DNA flanking sequences corresponding to (5') upstream region of the galactose permease; b) modifying an endogenous regulatory region which is operably linked to a nucleic acid encoding a glucokinase in the PTS⁻/Glu⁻ host cell by transforming the PTS⁻/Glu⁻ host cell with a second DNA construct comprising an exogenous promoter and DNA flanking sequences corresponding to upstream (5') regions of the glucokinase; c) allowing integration of the first and the second DNA constructs, wherein the first DNA construct replaces the endogenous promoter of the nucleic acid encoding the galactose permease and the second DNA construct replaces the endogenous promoter of the nucleic acid encoding the glucokinase d) culturing the transformed bacterial host cell under suitable conditions; and e) allowing expression of the galactose permease and the glucokinase from the modified regulatory regions to obtain an altered bacterial cell having an increase specific growth rate compared to the specific growth rate of a corresponding unaltered PTS bacterial host cell cultured under essentially the same culture conditions.

In a ninth aspect, the invention pertains to a method for increasing the production of a desired product in a PTS⁻/Glu⁻ E. coli host cell originally capable of utilizing a PTS for carbohydrate transport which comprises a) modifying an endogenous chromosomal regulatory region which is operably linked to a nucleic acid encoding a galactose permease in an E. coli PTS⁻/Glu⁻ cell by transforming the E. coli PTS⁻/Glu⁻ cell with a first DNA construct comprising an exogenous promoter and DNA flanking sequences corresponding to upstream (5') regions of the galactose permease; b) modifying an endogenous chromosomal regulatory region which is operably linked to a nucleic acid encoding a glucokinase in the E. coli PTS⁻/Glu⁻ cell by transforming the E. coli PTS⁻/Glu⁻ cell with a second DNA construct comprising an exogenous promoter and DNA flanking sequences corresponding to upstream (5') regions of the glucokinase; c) culturing the transformed E. coli PTS⁻/Glu⁻ cell under suitable conditions to allow expression of the galactose permease and expression of the glucokinase; and d) obtaining an increased amount of a desired product in the transformed E. coli cells compared to the amount of the desired product in a corresponding PTS⁻/Glu⁻ E. coli cell cultured under essentially the same culture conditions wherein the desired product is ethanol, chorismate or succinate.

In a tenth aspect, the invention pertains to the transformed bacterial cells obtained according to the methods of the first through ninth aspects. In one preferred embodiment, the transformed bacterial cells are E. coli cells, Bacillus cells or Pantoea cells.

Figure 1A:
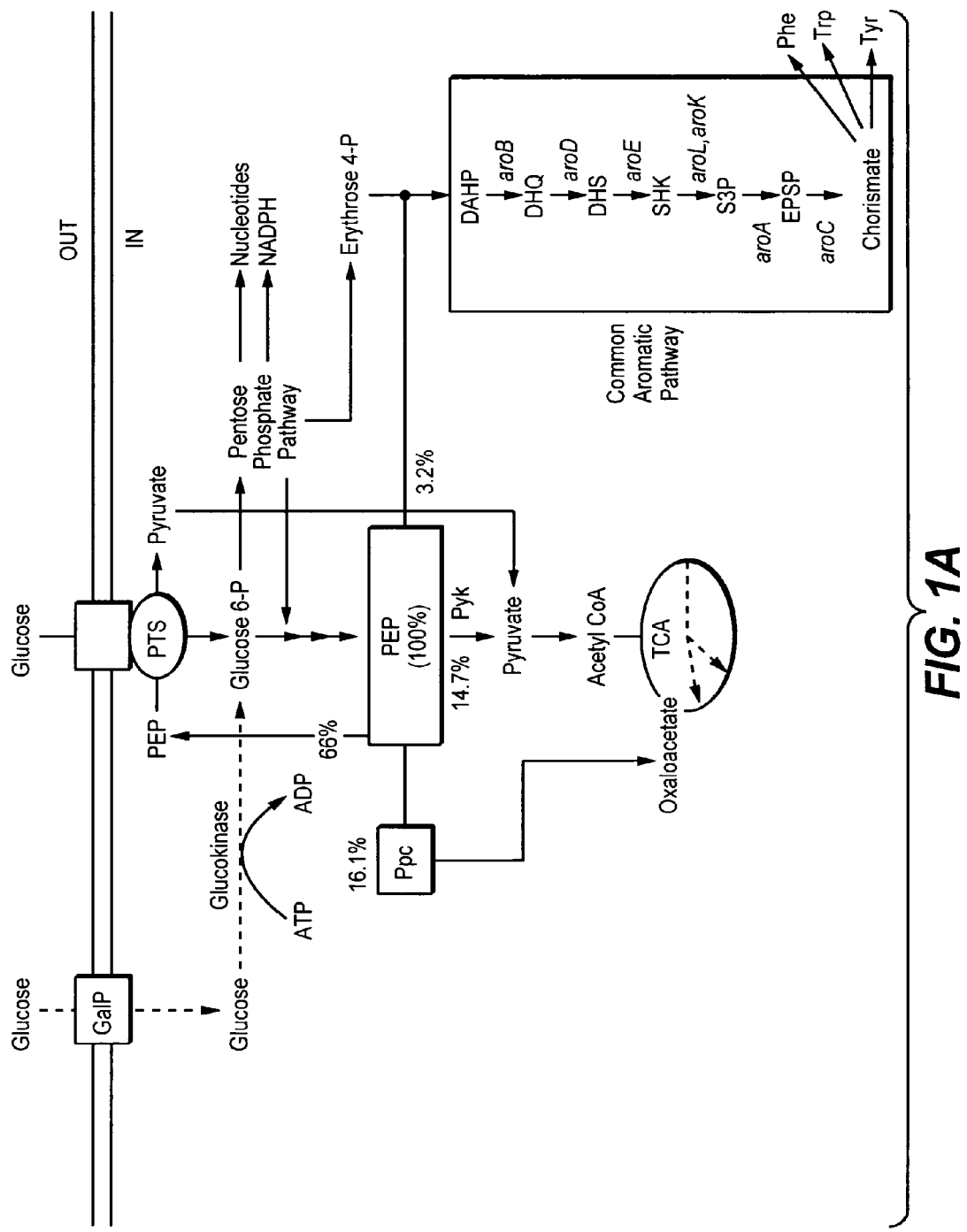
FIGS. 1A and 1B illustrate the pathways of central carbon metabolism in E. coli, showing derivation of the carbon skeletons for various desired compounds including compounds in the biosynthesis of amino acids. From FIG. 1A it can be observed that (a) glucose is transported across the cell membrane by a galactose permease (GalP) transport protein and (b) that glucose moves across the membrane as to be phosphorylated by PEP in the PTS system. The phosphorylation of glucose by the PTS is the major consumer of PEP in PTS cells and the percentages shown in the figure represent the amount of PEP channeled into competing pathways as described by Holms (1986) *The central metabolic pathways of Escherichia coli: relationship between flux and control at a branch point, efficiency of conversion to biomass, and excretion of acetate.* In: CURRENT TOPICS IN CELLULAR REGULATION, Vol. 28, pp. 69-105 Academic Press, New York. For example, 66% of the PEP produced is used in the PTS system. The following metabolic systems are schematically illustrated in the figure: Embden-Meyerhoff pathway (glycolysis), the pentose phosphate pathway, tricarboxylic acid (TCA) pathway, common aromatic pathway, and the Entner-Doudoroff pathway.
Figure 1B:
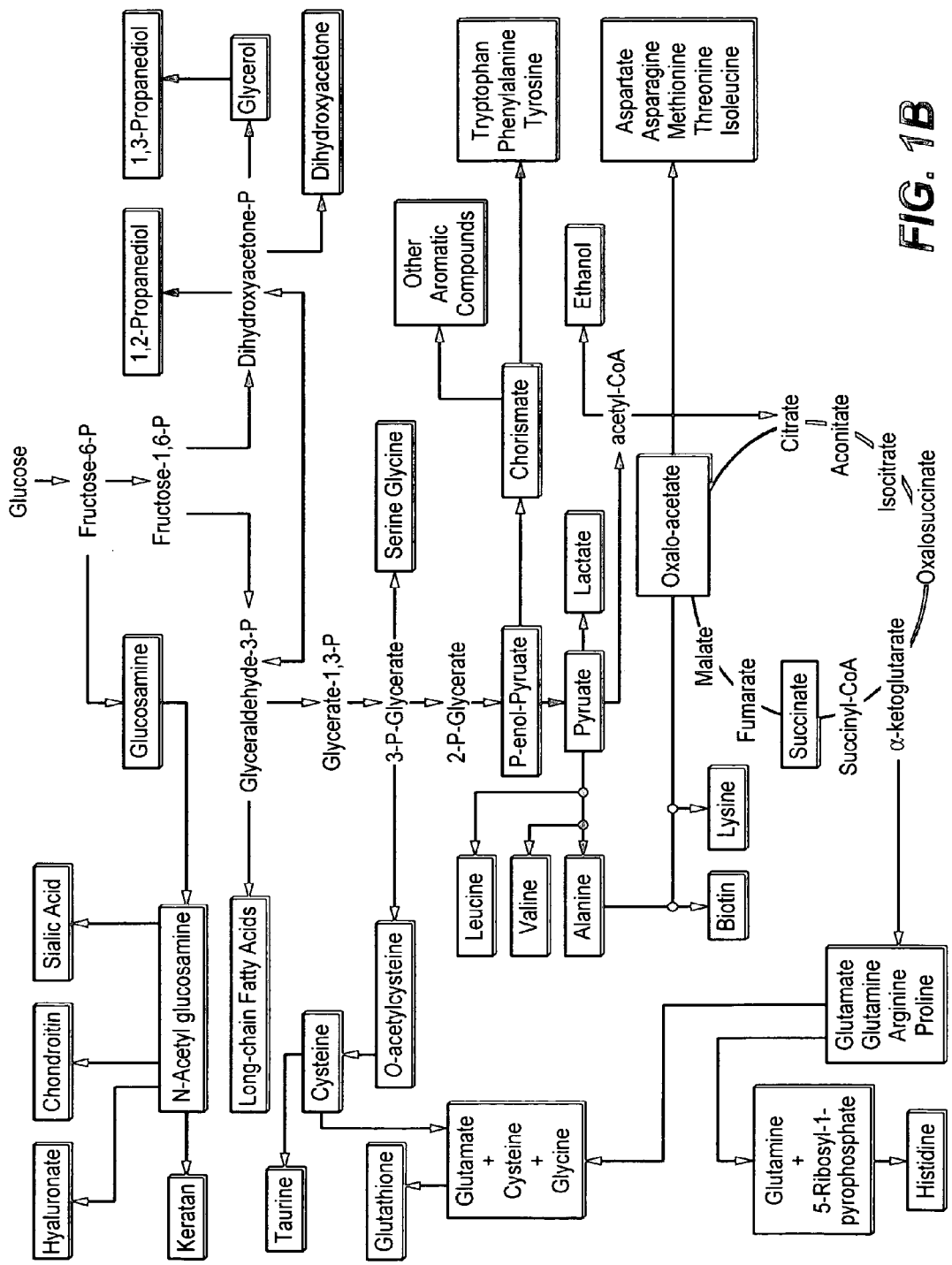

The following abbreviations are used in the figure and throughout the disclosure: PEP=phosphoenolpyruvate; DAHP=3-deoxy-D-arabino-heptulosonate 7-phosphate;

DHQ=3-dehydroquinate; DHS=3-dehydroshikimate; SHK=shikimate; S3P=shikimate 3-phosphate; EPSP=5-enolpyruvyl shikimate 3-phosphate; PHE=phenylalanine; TYR=tyrosine; TRP=tryptophan; Pyk=pyruvate kinase, which is encoded by the gene pyk; and Ppc=PEP carboxylase, which is encoded by the gene ppc. Further, the following genes are illustrated for the common aromatic pathway: aroB which encodes DHQ synthase; aroD which encodes DHQ dehydratase; aroE which encodes shikimate dehydrogenase; aroL and aroK which encode shikimate kinase; aroA which encodes EPSP synthase and aroC which encodes chorismate synthase. While not specifically illustrated, one skilled in the art is aware that aroG, aroF and aroH encode the three isozymes of DAHP synthase which catalyzes the conversion of Erythrose-4P (E4P) and PEP to DAHP in $E.\ coli$. FIG. 1B illustrates the varied compounds, the production of which, may be enhanced by an increase in carbon flux and PEP availability according to the methods encompassed by the invention.

FIG. 2 illustrates the DNA sequence of the GalP-ptrc DNA cassette as set forth in SEQ ID NO. 1 cloned into the R6K vector (creating pR6K-galP). Italics and bold nucleotide sequences represent the loxP sequences; bold and underlined nucleotide sequences represent the chloramphenicol acetyltransferase (CAT) gene in reverse orientation to galP; underlined sequences represent the −35 region (TTGACA) and the −10 region (TATAAT) of the trc promoter; the italicized nucleotides represent the lac operator of the trc promoter; and the bold nucleotides represent the galP ATG start codon. (Reference is made to example 1B).

FIG. 3 illustrates the DNA sequences of the galP-trc DNA cassette after removal of the CAT gene (SEQ ID NO. 2). The bold nucleotides represent the galP upstream sequence; italicized nucleotides represent a single loxP site, and bold and italics nucleotides represent the trc promoter region, wherein the −35 box and the −10 box are underlined. (Reference is made to example 1E).

FIG. 4 illustrates the DNA sequence of the glk-trc DNA cassette as set forth in SEQ ID NO. 3 and which was used to clone into the R6K vector. Italics and bold nucleotide sequences represent the loxP sequences; bold and underlined nucleotide sequences represent the CAT gene in reverse orientation to glk; underlined sequences represent the −35 region (CTGACA) and the −10 region (TATAAT) of a trc derivative promoter; the italicized nucleotides represent the lac operator of the trc promoter; and the bold nucleotides represent the glk ATG start codon. (Reference is made to example 1F).

Figure 5:
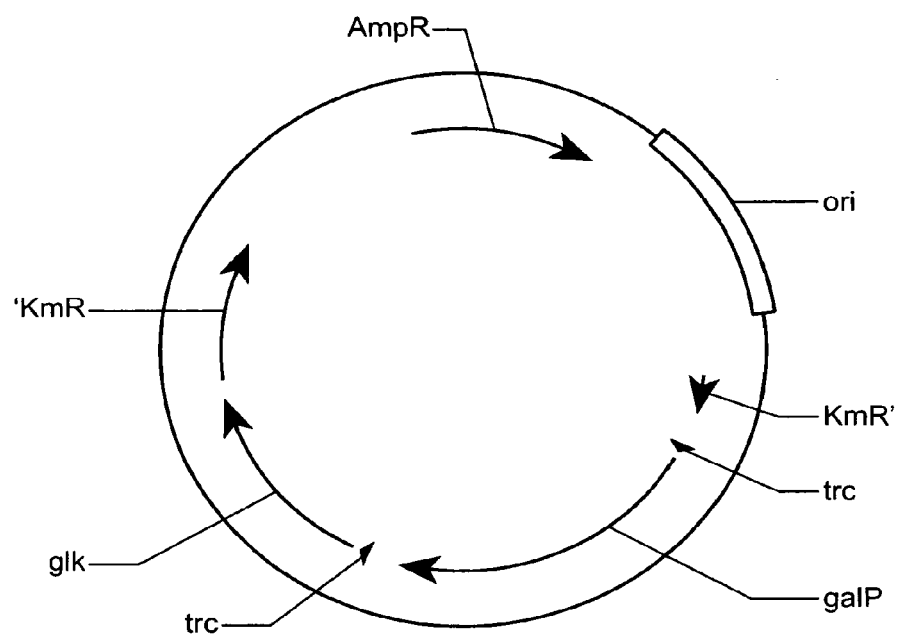

FIG. 5 illustrates a plasmid map of pMCGG and reference is made to example 1G. The galP and glk open reading frames (orfs) were cloned into pACYC177, each under the control of the trc promoter. Trc=trc promoter; galP=galactose permease coding sequence; glk=glucokinase coding sequence; KmR'=kanamycin resistance marker of pACYC177 (interrupted by cloned genes); Amp=ampicillin resistance marker of pACYC177 and ori=plasmid origin of replication.

Figure 6:
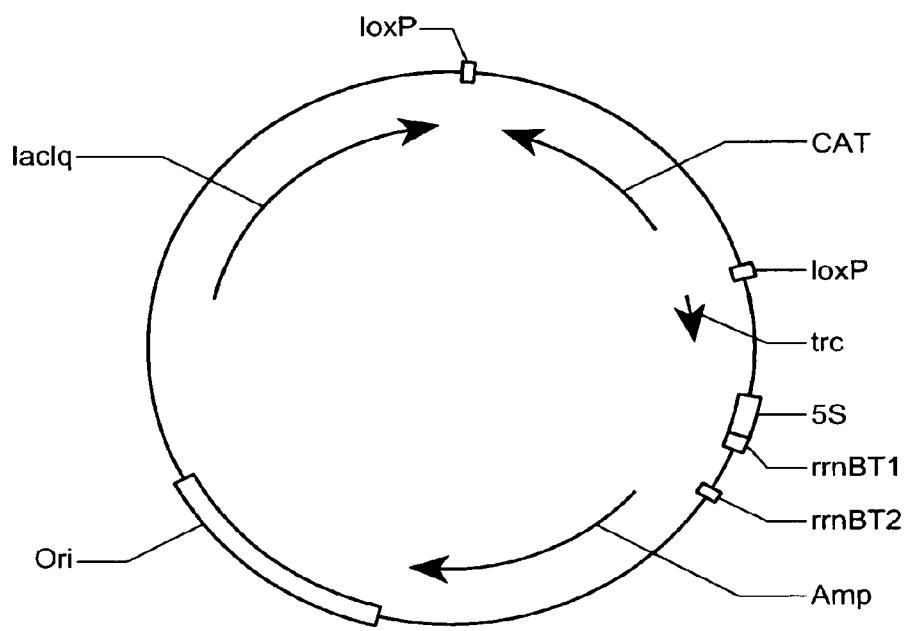

FIG. 6 illustrates a plasmid map of pTrcm42 and reference is made to example 1A. LoxP=loxP sites; trc=trc promoter, lacIq=gene encoding the LacI$^q$ repressor protein; CAT=CAT encoding gene; 5S=5StRNA; rrnBT1 and 2=ribosomal RNA terminators; Amp=ampicillin resistance gene of pTrc99a; and ori=pMB1origin of replication.

Figure 7A:
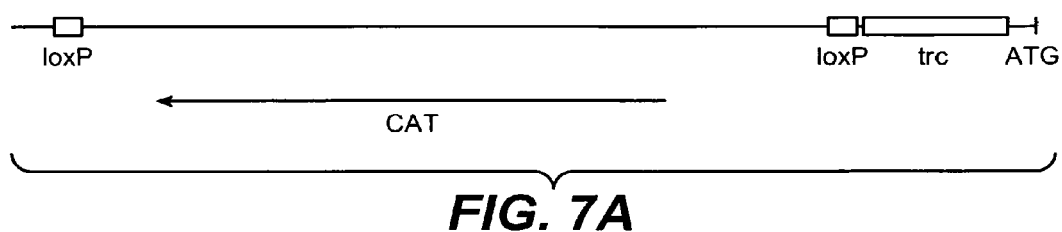
Figure 7B:
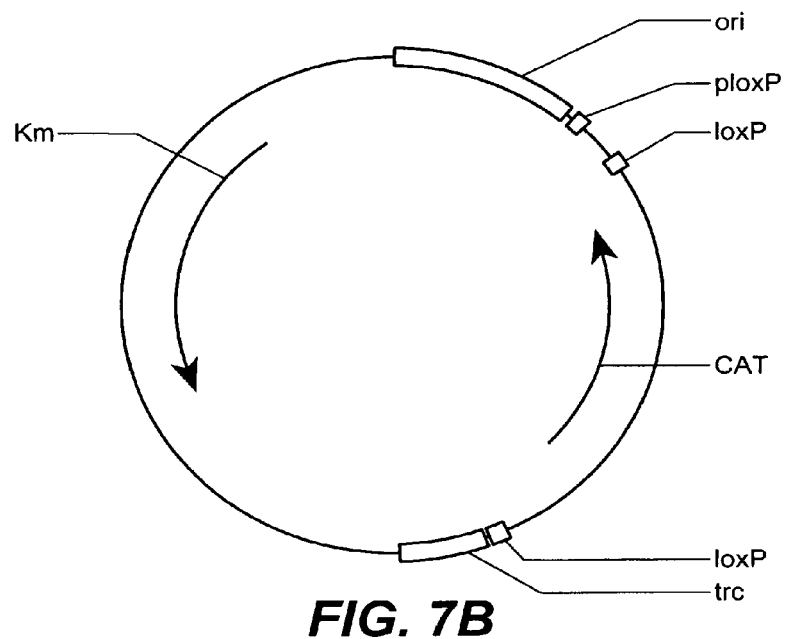

FIGS. 7A and 7B. FIG. 7A illustrates a diagram of a schematic promoter DNA integration cassette comprising loxP-CAT-loxP-ptrc. DNA homology to a desired site of integration is added by PCR such that it flanks the entire cassette and reference is made to example 1E and 1F. loxP=loxP sites; CAT=chloramphenicol acetyltransferaces gene, trc=trc promoter; and ATG=start codon of the glucose assimilation gene targeted for integration of the DNA cassette. FIG. 7B illustrates a plasmid map of pRGK-galP-trc, which was created by amplifying the DNA cassette of FIG. 7A flanked by 40-bp of homology to the regulatory region of galP from 221-183 bp upstream of the ATG start codon of galP (5' flank) and 40 bp upstream of and including the ATG start codon of galP (3' flank) wherein ploxP=plasmid encoded loxP; loxP=introduced loxP sequences from the DNA cassette; trc=trc promoter; Km=kanamycin resistance gene; CAT is as defined above and ori=R6K plasmid origin of replication.

FIG. 8 illustrates the nucleotide sequence of plasmid pSYCO101 (SEQ ID NO. 4).

Figure 9:
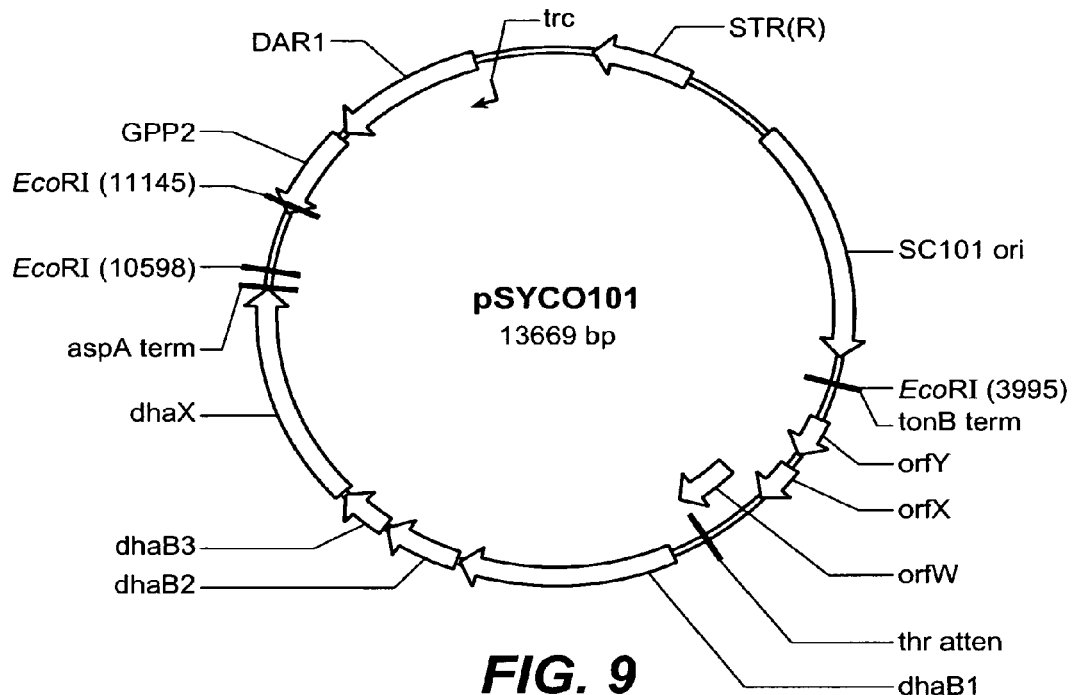

FIG. 9 depicts a plasmid map of pSYCO101, wherein DAR1 (dihydroxyacetone phosphate reductase) and GPP2 (glycerol-phosphate phosphatase) are glycerol pathway genes; STR(R) is a spectinomycin resistance encoding gene; pSC101 ori is an origin of replication of the plasmid; AspA term is an aspartate ammonia lyase gene terminator; dhaB1-3, dhaX, and orf W, X, Y are 1, 3 propanediol pathway genes; Thr atten is an $E.\ coli$ threonine operon attenuator; TonB term is an $E.\ coli$ tonB gene terminator; trc is the trc promoter and EcoR1 is the EcoR1 restriction enzyme sites in pSYCO101. (Reference is made to example 1H).

Figure 10A:
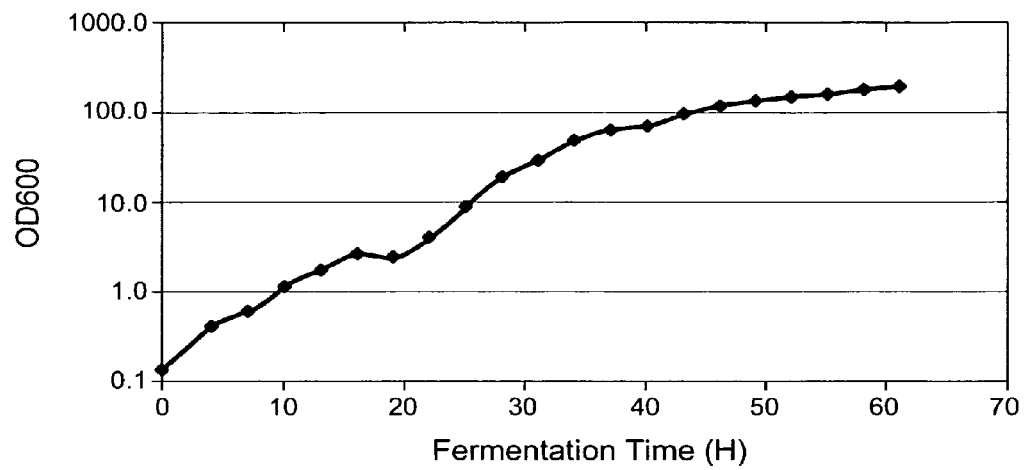
Figure 10B:
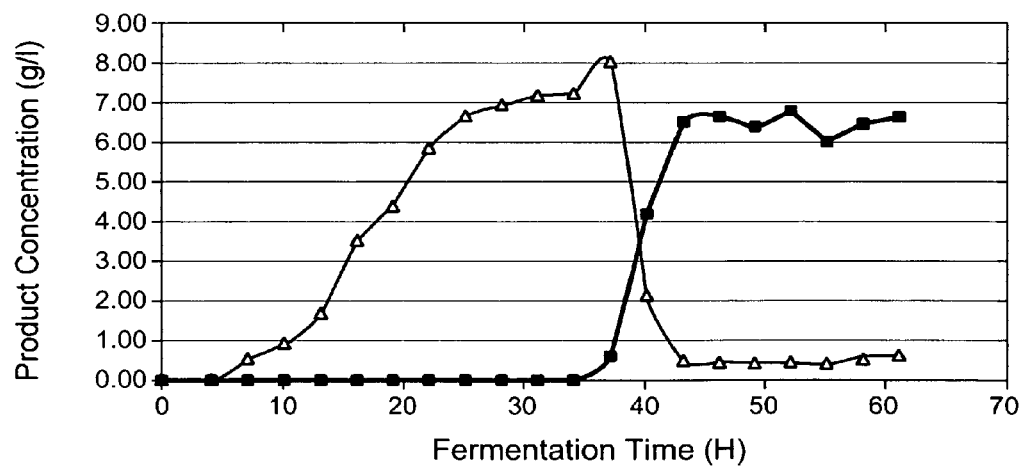

FIGS. 10A and 10B illustrate cell growth and the production of glycerol and 1,3-propanediol over fermentation time (h) in a PTS$^-$/Glu$^+$ $E.\ coli$ with a plasmid encoded PEP-independent glucose transport system. The PTS$^-$/Glu$^-$ strain, KLpts7 (example 1D) was transformed with pMCGG (example 1G) and with pSYCO101 and the resultant strain was tested and analyzed for cell growth, glycerol and 1,3-propanediol production. Optical density (OD$_{600}$) is represented by -♦-, glycerol concentration is represented by -▲-, and 1,3-propanediol concentration is represented by -■-.

Figure 11A:
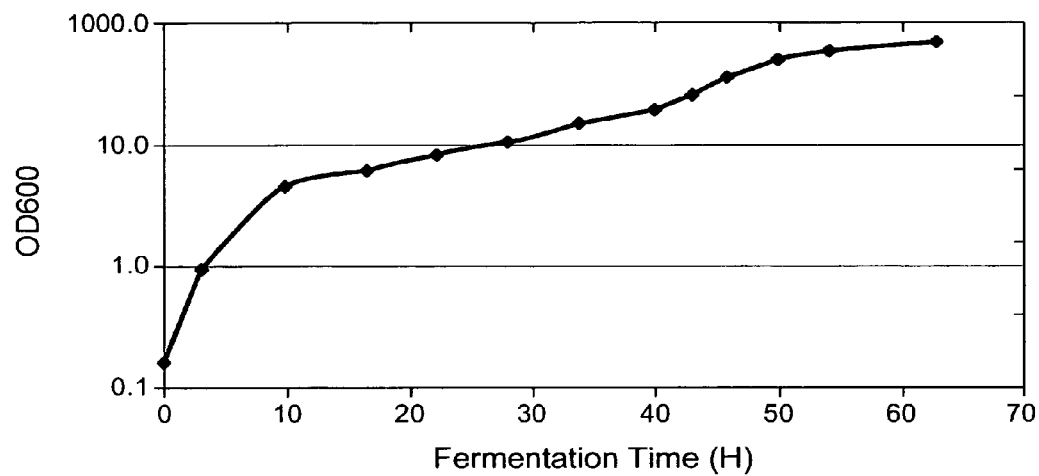
Figure 11B:
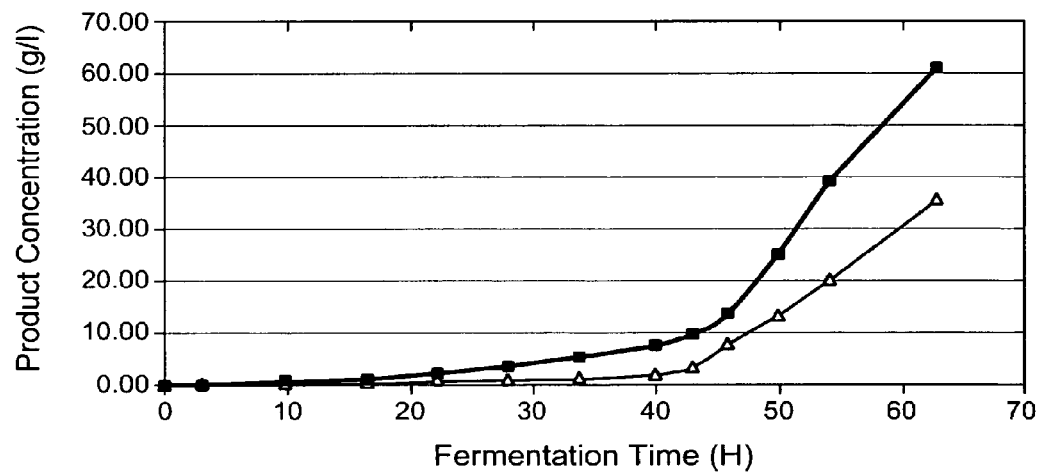

FIGS. 11A and 11B illustrate cell growth and the production of glycerol and 1,3-propanediol over fermentation time (h) in a PTS$^-$/Glu$^+$ $E.\ coli$ with the expression of galP controlled by a chromosomally integrated trc promoter and that of glk by natural regulation. The PTS$^-$/Glu$^-$, KLpts7 (example 1D) was made Glu$^+$ by integration of the trc promoter at the galP target site to yield strain KlgalP-ptrc (example 1E). This strain was transformed with pSYCO103 and analyzed by fermentation (example 2). The parameters examined include, for FIG. 11A cell density (OD$_{600}$) (-♦-) and for FIG. 11B glycerol concentration (-▲-) and 1,3-propanediol concentration (-■-).

Figure 12A:
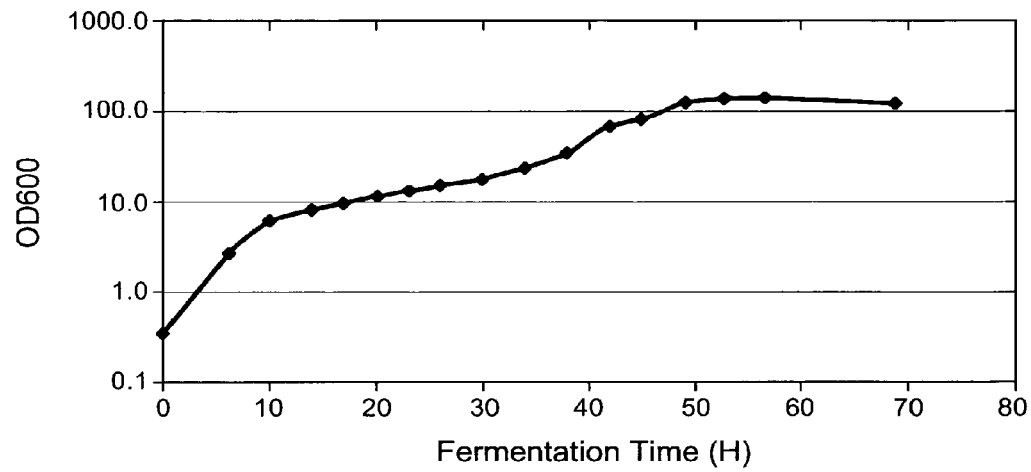
Figure 12B:
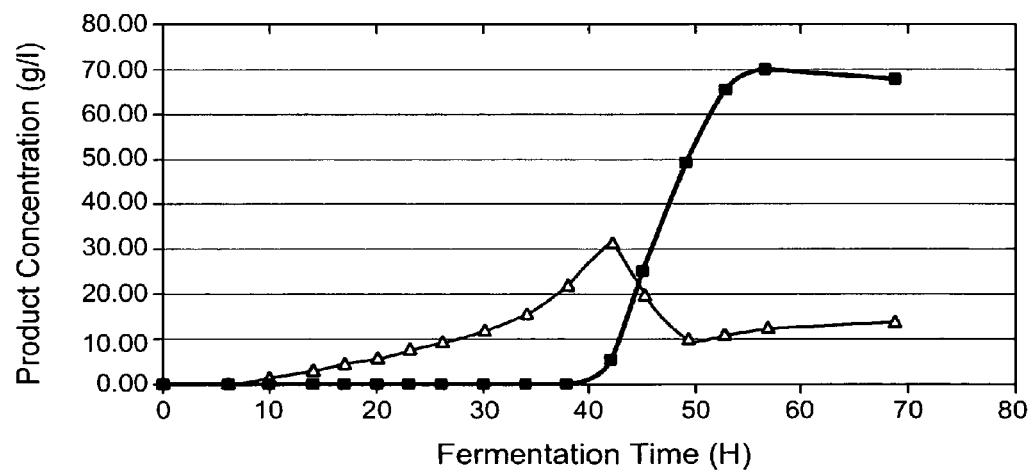

FIGS. 12A and 12B illustrate cell growth and the production of glycerol and 1,3-propanediol over fermentation time (h) in a PTS$^-$/Glu$^+$ $E.\ coli$ with the expression of galP and glk controlled by a chromosomally integrated trc promoter. The PTS$^-$/Glu$^-$, KLpts7 (example 1D) was made Glu+ by integration of the trc promoter at the galP and glk target sites to yield strain KLGG (example 1F). This strain was transformed with pSYCO101 and analyzed by fermentation (example 3). The parameters examined include, for FIG. 12A cell density (OD$_{600}$) (-♦-) and for FIG. 12B glycerol concentration (-▲-) and 1,3-propanediol concentration (-■-).

Figure 13:
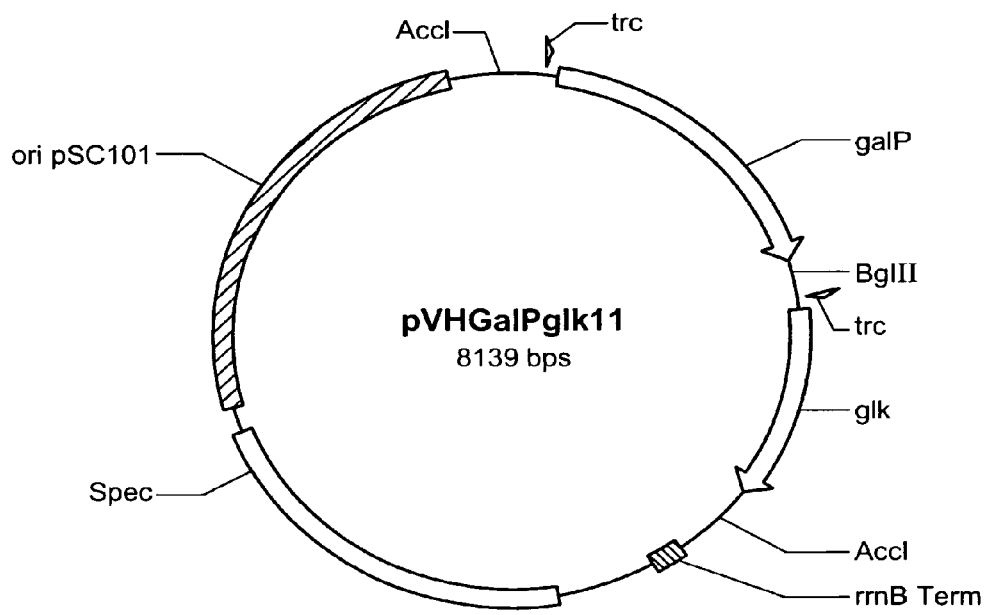

FIG. 13 is a map of plasmid pVHGalPglk11 as described in example 1G.

Figure 14A:
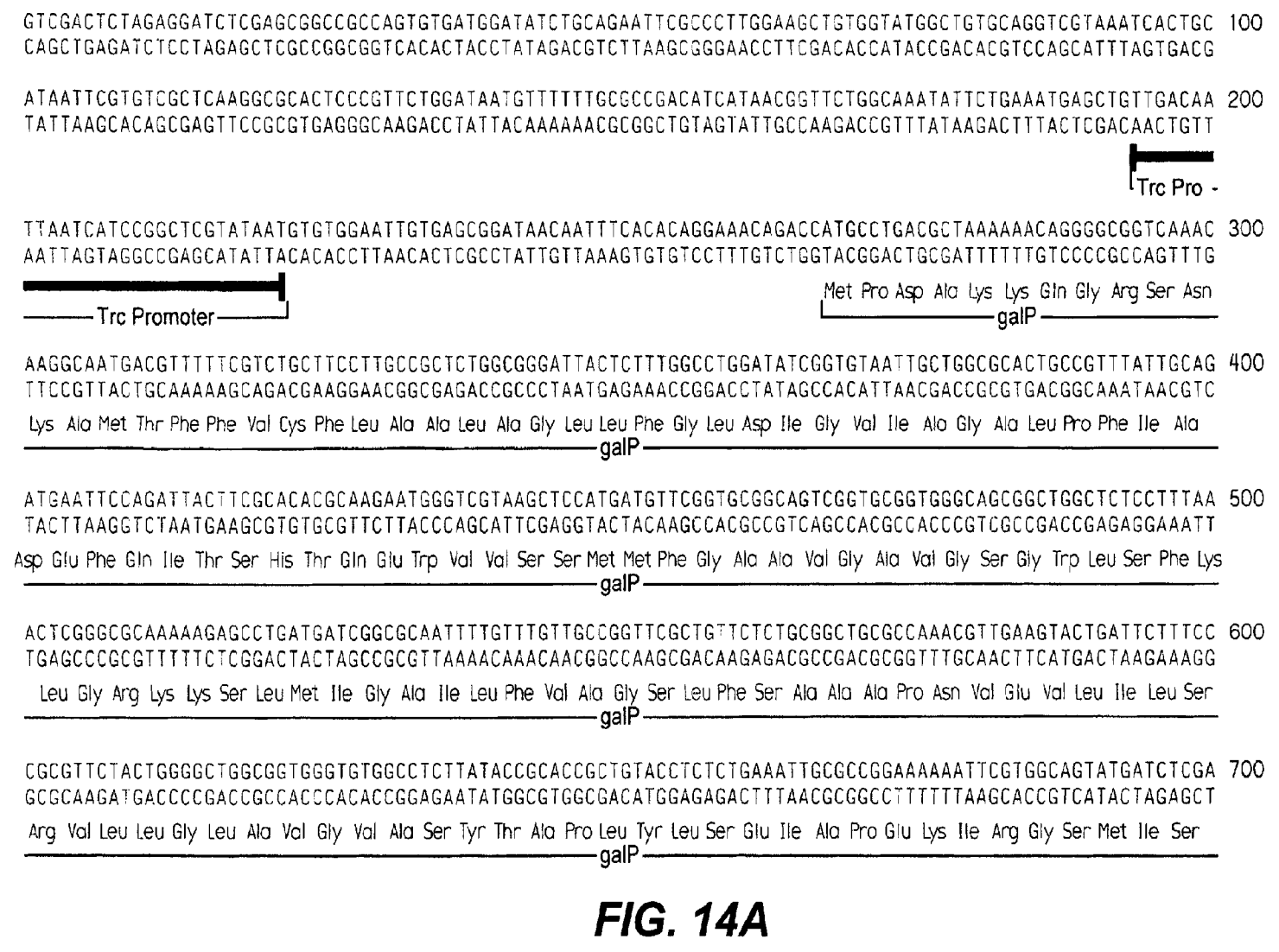
Figure 14B:
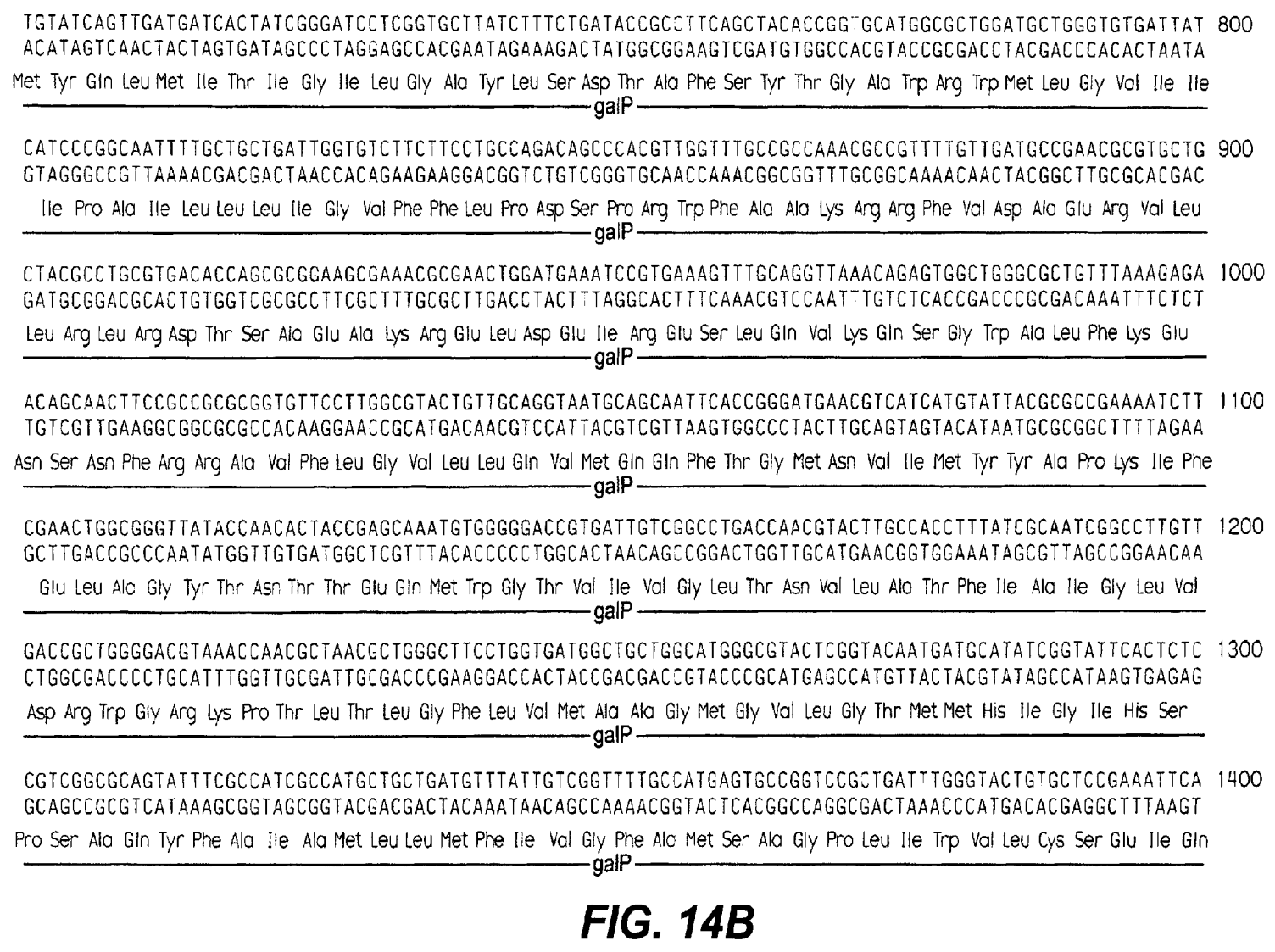

FIG. 14A-E illustrates the nucleotide sequences (SEQ ID NO. 25) and coding sequences for galP and Glk (SEQ ID NO. 26) of pVHGalPglk11.

DETAILED DESCRIPTION OF THE PREFERRED EMBODIMENTS

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, MOLECULAR CLONING: A LABORATORY MANUAL, second edition (Sambrook et al., 1989) Cold Spring Harbor Laboratory Press; CURRENT PROTOCOLS IN MOLECULAR BIOLOGY (F. M. Ausubel et al., eds., 1987 and annual updates); GENE EXPRESSION TECHNOLOGY, (Goeddel, D. ed., 1991, METHODS IN ENZYMOLOGY Vol. 185 Academic Press, San Diego, Calif.); GUIDE TO PROTEIN PURIFICATION (Deutshcer M. P. ed., 1989, METHODS IN ENZYMOLOGY, Academic Press, San Diego, Calif.); PCR PROTOCOLS: A GUIDE TO METHODS AND APPLICATIONS (Innis et al., 1990, Academic Press, San Diego, Calif.); OLIGONUCLEOTIDE SYNTHESIS (M. J. Gait, ed., 1984); PCR: THE POLYMERASE CHAIN REACTION, (Mullis et al., eds., 1994); MANUAL OF INDUSTRIAL MICROBIOLOGY AND BIOTECHNOLOGY, Second Edition (A. L. Demain, et al., eds. 1999); MANUAL OF METHODS FOR GENERAL BACTERIOLOGY (Phillipp Gerhardt, R. G. E. Murray, Ralph N. Costilow, Eugene W. Nester, Willis A. Wood, Noel R. Krieg and G. Briggs Phillips, eds), pp. 210-213 American Society for Microbiology, Washington, D.C.; and BIOTECHNOLOGY: A TEXTBOOK OF INDUSTRIAL MICROBIOLOGY, (Thomas D. Brock) Second Edition (1989) Sinauer Associates, Inc., Sunderland, Mass.

Definitions

Unless defined otherwise herein, all technical and scientific terms used herein have the same meaning as commonly understood by one of ordinary skill so in the art to which this invention pertains. Singleton, et al., DICTIONARY OF MICROBIOLOGY AND MOLECULAR BIOLOGY, 2D ED., John Wiley and Sons, New York (1994) and Hale and Marham, THE HARPER DICTIONARY OF BIOLOGY, Harper Perennial, New York (1991) provide one of skill with general dictionaries of many of the terms used in this invention.

Numeric ranges are inclusive of the numbers defining the range. Unless otherwise indicated nucleic acids are written left to right in the 5' to 3' orientation and amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The references, issued patents and pending patent applications cited herein are incorporated by reference into this disclosure.

The phosphotransferase system (PTS) (E.C. 2.7.1.69) refers to the phosphoenolpyruvate-dependent sugar uptake system. This is a system of transporter proteins that participate in transport and phosphoenolpyruvate dependent phosphorylation of several sugars. The system is comprised of two phosphoproteins, enzyme I and HPr, which are common to all PTS carbohydrates and catalyze the transfer of a phosphoryl group from PEP to the carbohydrate specific membrane bound enzyme II and then to the carbohydrate. In some cases enzyme III is positioned between HPr and enzyme II. To distinguish the various enzymes II and enzymes III, a three letter superscript is used to indicate which carbohydrate is the preferred substrate. For example Enzyme II$^{glc}$ means glucose is the preferred substrate. However other substrates may be used.

The terms "PtsI" and "Enzyme I" refer to the phosphotransferase EC 2.7.3.9 encoded by ptsI in $E.\ coli$. The terms "HPr" and "PtsH" refer to the phosphocarrier protein encoded by ptsH in $E.\ coli$. The terms "glucose-specific IIA component", "Enzyme II$^{glc}$" and "Crr" refer to EC 2.7.1.69 encoded by err in $E.\ coli$. The PTS comprises PtsI, PtsH and Crr and functionally equivalent proteins.

The terms "PTS$^-$/Glu$^-$ phenotype" and "PTS$^-$/Glu$^-$" mean a host cell which has a significantly reduced ability to utilize glucose as a carbon source because the PEP-dependent PTS is inactivated compared to the corresponding wild-type PTS cell. Effectively, less PEP is utilized to transport glucose than in the wild-type PTS cell.

"Restoring the glucose$^+$ (Glu$^+$) phenotype" means a host cell capable of using glucose as a carbon source despite the inactivation of the PTS. Further a "PTS$^-$/Glu$^+$ phenotype" as used herein means a PTS$^-$/Glu$^-$ host cell that has a restored Glu$^+$ phenotype.

"Increased phosphoenolpyruvate (PEP) availability" means increasing the amount of intracellular PEP which enhances carbon committed to a metabolic or productive pathway, said PEP which would otherwise have been metabolized in the PTS for phosphorylation of glucose.

The phrase "increasing carbon flow" means increasing the availability of carbon substrates to metabolic or productive pathways, said carbon substrate which would otherwise be diverted by the metabolism of PEP in the PTS. Carbon flow to a particular pathway can be measured by well know methods such as gas chromatography and mass spectroscopy. Carbon flow as measured by produced product may be at least 2%, 5%, 10%, 15%, 20%, 25%, 30%, or greater than the carbon flow in a corresponding PTS cell grown under essentially the same growth conditions.

The term "specific growth rate ($\mu$)" refers to the increase of mass or cell number per time. In one embodiment of the invention a cell having a restored Glu$^+$ phenotype will have a specific growth rate ($\mu$) of about at least 0.3 hr$^1$, at least 0.4 hr$^{-1}$, at least 0.5 hr$^1$, at least 0.6 hr$^{-1}$, at least 0.7 hr$^{-1}$ and at least 0.8 hr$^{-1}$ when grown on is glucose.

The terms "regulatory region" and "regulatory sequence" are used interchangeably herein and mean a nucleic acid sequence that is operably linked with a coding region of a gene to effect expression of the coding region. A regulatory sequence can inhibit, repress or promote expression of the operably linked coding sequence or translation of the mRNA. Examples of regulatory sequences include promoters, enhancers, ribosome binding sites, operators and silencers.

An "endogenous chromosomal regulatory region" and "homologous chromosomal regulatory region" refer to a chromosomal regulatory region, which naturally occurs in a host cell and which is operably linked to a polynucleotide encoding a glucose assimilation protein in said host cell.

The term "promoter" as used herein refers to a regulatory nucleic acid sequence that functions to direct transcription of a downstream gene or genes. A promoter according to the invention comprises two consensus regions. The first consensus region is centered about 10 base pairs (bp) upstream from the start site of transcription initiation and is referred to as the −10 consensus region (also the −10 box or Pribnow box). The second consensus region is centered about 35 bp upstream of the start site and is referred to as the −35 consensus box or sequence. A linker or spacer sequence is positioned between the consensus boxes and generally comprises 14 to 20 bp.

An "exogenous promoter" as used herein is a promoter, other than a naturally occurring promoter, which is operably linked to an endogenous coding region of a glucose assimilation protein of interest in a host cell and includes but is not limited to non-native promoters, synthetic promoters, and modified naturally occurring promoters. Modified naturally occurring promoters include native endogenous promoters which are operably linked to a polynucleotide encoding a glucose assimilation protein, wherein the native promoter has been altered and then reintroduced into a host cell chromosome and include native endogenous promoters which are not operably linked to an endogenous coding region of a glucose assimilation protein.

The terms "derivative promoter", "modified promoter" and "variant promoter" mean a promoter, wherein at least one nucleotide of the promoter has been altered. In one preferred embodiment, a derivative promoter will comprise a modification, such as a substitution, of at least one nucleotide of the −35 box of the promoter.

"Under transcriptional control" or "transcriptionally controlled" are terms well understood in the art that indicate that transcription of a polynucleotide sequence, usually a DNA sequence, depends on its being operably linked to an element which contributes to the initiation of, or promotes, transcription.

"Operably linked" refers to a juxtaposition wherein the elements are in an arrangement allowing them to be functionally related. For example, a promoter is operably linked to a coding sequence if it directs transcription of the sequence.

"Under translational control" is a term well understood in the art that indicates a regulatory process that occurs after the messenger RNA has been formed.

As used herein the term "gene" means a DNA segment that is involved in producing a polypeptide and includes regions preceding and following the coding regions as well as intervening sequences (introns) between individual coding segments (exons).

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, DNA constructs and primers. A polynucleotide may comprise modified nucleotides, such as methylated nucleotides and nucleotide analogs, uracyl, other sugars and linking groups such as fluororibose and thioate, and nucleotide branches.

A "structural sequence" is a putative polynucleotide sequence of DNA that encodes the formation of a product. A structural sequence can encode the amino acid sequence of a polypeptide chain having messenger RNA is its primary product. A structural sequence can also encode the formation of an RNA with structural or regulatory function.

As used herein, the term "vector" refers to a polynucleotide construct designed to introduce nucleic acids into one or more cell types. Vectors include cloning vectors, expression vectors, shuttle vectors, plasmids, cassettes and the like. In the specific case of a DNA cassette, the DNA may be generated in vitro by PCR or any other suitable techniques.

The term "over expressed" means an increased number of copies of the same gene product in a host cell.

The terms "protein" and "polypeptide" are used interchangeability herein. The 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

As used herein when describing proteins, and genes that encode them, the term for the gene is not capitalized and is italics, i.e. glkA. The term for the protein is generally not italicized and the first letter is capitalized, i.e. GlkA.

"A glucose assimilation protein" or "an enzyme involved in glucose assimilation" means an enzyme or protein that enables a host cell to utilize glucose as a carbon source. Enzymes and proteins involved in glucose assimilation include those involved in glucose transport across the cell membrane and those involved in phosphorylation of glucose to glucose-6-phosphate.

"A phosphorylating enzyme" means an enzyme that catalyzes the reaction of glucose to glucose 6-phospahte.

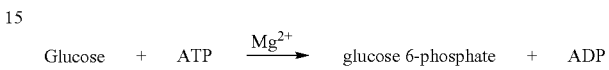

Enzymes known to catalyze this reaction include hexokinases (E.C. No.: 2.7.1.1) and glucokinases (E. C. No. 2.7.1.2). Glucokinase is encoded by glk in *E. coli*.

A "transport protein" or "transporter" refers to a protein that catalyzes the movement of a molecule across a cell membrane. In a preferred embodiment, the transporter, also referred to as a permease is a glucose transporter. A glucose transporter catalyzes the active transport of glucose across a cell membrane into the cytoplasm. A glucose transporter may also catalyze the transport of other sugars. One example of a glucose transporter is a galactose-proton symporter (also known as a galactose permease), GalP. GalP is encoded by galP in *E. coli* (Henderson et al., (1990) *Phil. Trans. R. Soc.*, London 326:391-410).

"Active transport" refers to the transport of a compound into a cell that is coupled to an expenditure of energy. One example emcompassed by the invention is the use of membrane potential by glucose transporters.

As used herein a "selectable marker" refers to a gene capable of expression in a host cell which allows for ease of selection of those hosts containing an introduced nucleic acid or vector. Examples of such selectable markers include but are not limited to antimicrobials (e.g. kanamycin, erythromycin, actinomycin, chloramphenicol, spectinomycin, and tetracycline). The designation "Cm$^R$" and "CAT" for example both refer to the same gene, a chloramphenicol resistance gene and also known as the chloroamphenicol acetyltransferase gene.

A "flanking sequence" refers to any sequence that is either upstream or downstream of the sequence being discussed (e.g. for genes A, B, and C; gene B is flanked by the A and the C gene sequences). In some embodiments, a flanking sequence is present on only a single side (either 3' or 5') of a DNA fragment, but in preferred embodiments, each side of the sequence being discussed is flanked.

The term wild-type refers to a native or naturally occurring host cell or host cell sequence.

As used herein, the term "endogenous" refers to a nucleic acid or protein encoded by a nucleic acid naturally occurring in the host. The term "exogenous" refers to a nucleic acid or protein from a different host cell strain. An exogenous sequence can be a non-host sequence and a synthetically modified native sequence.

The term "homologous" means of the same organism, strain or species. A "homologous sequence" is a sequence that is found in the same genetic source or species. For example if a host strain lacks a specific gene, but the same gene is found in other strains of the same species the gene would be considered a homologous sequence. The term "heterologous"

means of a different organism, strain or species and more specifically refers to nucleic acid or amino acid sequences not naturally occurring in the host cell.

The terms "transformation", "transduction" and "transfection" refer to the incorporation or introduction of new polynucleotides into a cell. The introduced polynucleotides may be integrated into the chromosomal DNA or introduced as extra chromosomal replicating sequences.

The terms "isolated" or "purified" as used herein refer to an enzyme, nucleic acid, protein, peptide or co-factor that is removed from at least one component with which it is naturally associated.

"Desired product" as used herein refers to the desired compound into which a carbon substrate is bioconverted. Exemplary desired products are succinate, lysine, glycerol, methionine, threonine, isoleucine, pyruvate, ethanol, formate, acetate, DAHP, DHQ, DHS, SHK, S3P, EPSP, chorismate, phenylalanine, tyrosine, tryptophan, and ascorbic acid intermediates.

As used herein, the term "carbon source" encompasses suitable carbon substrates ordinarily used by microorganisms, such as 6 carbon sugars, including but not limited to glucose (G), gulose, lactose, sorbose, fructose, idose, galactose and mannose all in either D or L form, or a combination of 6 carbon sugars, such as glucose and fructose, and/or 6 carbon sugar acids. Preferred carbon substrates include glucose and fructose.

The terms "non-functional", "inactivated" and "inactivation" when referring to a gene or a protein means that the known normal function or activity of the gene or protein has been eliminated or highly diminished. Inactivation which renders the gene or protein non-functional includes such methods as deletions, mutations, substitutions, interruptions or insertions in the nucleic acid sequence.

A "host cell" is a cell capable of receiving introduced, heterologous polynucleotides. In one embodiment the host cell is a gram-negative or gram-positive bacteria.

As used herein, the term "bacteria" refers to any group of microscopic organisms that are prokaryotic, i.e., that lack a membrane-bound nucleus and organelles. All bacteria are surrounded by a lipid membrane that regulates the flow of materials in and out of the cell. A rigid cell wall completely surrounds the bacterium and lies outside the membrane. There are many different types of bacteria, some of which include, but are not limited to *Bacillus, Streptomyces, Pseudomonas*, and strains within the families of Enterobacteriaceae.

As used herein, the family "Enterobacteriaceae" refers to bacterial strains having the general characteristics of being gram negative and being facultatively anaerobic. Included in the family of Enterobacteriaceae are *Erwinia, Enterobacter, Gluconobacter, Klebsiella, Escherichia, Acetobacter, Coyrnebacteria* and *Pantoea*.

An "altered bacterial host" or "modified bacterial host" according to the invention is a genetically engineered bacterial cell having a PTS$^-$/Glu$^+$ phenotype.

An "unaltered bacterial host cell" refers to a bacterial host cell which uses PTS to transport and phosphorylate glucose or a PTS$^-$/Glu$^-$ cell.

As used herein "chromosomal integration" is a process whereby an introduced polynucleotide is incorporated into a host cell chromosome. The process preferably takes place by homologous recombination. Homologous recombination is the exchange of DNA fragments between two DNA molecules is wherein the homologous sequences of the introduced polynucleotide align with homologous regions of the host cell chromosome and the sequence between the homologous regions of the chromosome is replaced by the sequences of the introduced polynucleotide in a double crossover.

A "target site" is intended to mean a predetermined genomic location within a host cell chromosome where integration of a DNA construct is to occur.

As used herein, "modifying" the level of protein or enzyme activity produced by a host cell refers to controlling the levels of protein or enzymatic activity produced during culturing, such that the levels are increased or decreased as desired.

As used herein, the term "modified" when referring to nucleic acid or a polynucleotide means that the nucleic acid has been altered in some way as compared to a wild type nucleic acid, such as by mutation in; substitution of; insertion of; deletion of part or all of the nucleic acid; or by being operably linked to a transcriptional control region. As used herein the term "mutation" when referring to a nucleic acid refers to any alteration in a nucleic acid such that the product of that nucleic acid is partially or totally inactivated. Examples of mutations include but are not limited to point mutations, frame shift mutations and deletions of part or all of a gene.

A polynucleotide or polypeptide having a certain percentage (for example, 80%, 85%, 90%, 95%, 96%, 97% or 99%) of "sequence identity" to another sequence means that, when aligned, that percentage of bases or amino acids are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18. Preferred programs include the GCG Pileup program, FASTA (Pearson et al. (1988) Proc. Natl. Acad. Sci. USA 85:2444-2448) and BLAST (*BLAST Manual*, Altschul et al., Natl. Cent. Biotechnol. Inf., Natl Library Med. (NCBI NLM), NIH, Bethesda Md. and Altschul et al., (1997) *NAR* 25:3389-3402). Another preferred alignment program is ALIGN Plus (Scientific and Educational Software, Pennsylvania), preferably using default parameters, which are as follows: mismatch=2; open gap=0; extend gap=2. Another sequence software program that could be used is the TFastA Data Searching Program available in the Sequence Analysis Software Package Version 6.0 (Genetic Computer Group, University of Wisconsin, Madison, Wis.). One skilled in the art will recognize that sequences encompassed by the invention are also defined by the ability to hybridize under stringent conditions with the sequences exemplified.

A nucleic acid is "hybridizable" to another nucleic acid when a single stranded form of the nucleic acid can anneal to the other nucleic acid under appropriate conditions of temperature and solution ionic strength. Hybridization and washing conditions are well known and exemplified in Sambrook 1989, supra (see in particular chapters 9 and 11). Low stringency hybridization conditions correspond to a Tm of 55° C. (for example, 5×SSC, 0.1% SDS, 0.25 milk and no formamide or 5×SSC, 0.5% SDS and 30% formamide). Moderate stringency conditions correspond to a 6×SSC, 0.1% SDS, 0.05% milk with or without formamide, and stringent conditions correspond to for example, a Tm of 65° C. and 0.1×SSC, 0.1% SDS.

It is well understood in the art that the acidic derivatives of saccharides and other compounds such as organic acids, may exist in a variety of ionization states depending upon their surrounding media, if in solution, or out of solution from which they are prepared if in solid form. The use of a term, such as, for example, gluconic acid or acetic acid to designate such molecules is intended to include all ionization states of the organic molecule referred to. Thus, for example, "gluconic acid" and "gluconate" refer to the same organic moiety, and are not intended to specify particular ionization states or chemical forms.

The term "culturing" as used herein refers to fermentative bioconversion of a carbon substrate to a desired product within a reactor vessel. Bioconversion means contacting a microorganism with a carbon substrate to convert the carbon substrate to the desired product.

As used herein, the term "comprising" and its cognates are used in their inclusive sense; that is, equivalent to the term "including" and its corresponding cognates.

"A," "an" and "the" include plural references unless the context clearly dictates otherwise.

"Allowing the production of a desired product from a carbon source, wherein the production of the desired product is enhanced compared to the production of the desired product in a corresponding unaltered bacterial host cell" means contacting the substrate, e.g. carbon source, with the PTS⁻/Glu⁻ bacterial cell to produce the desired product.

Preferred Embodiments

The present invention is directed to a method for increasing carbon flow into a desired metabolic pathway of a host cell originally capable of utilizing a PTS for carbohydrate transport, said method including the steps of selecting a host cell which is effectively phenotypically PTS⁻ and modifying at least one homologous chromosomal regulatory region, which is operably linked to a chromosomal nucleic acid which encodes a polypeptide involved in glucose assimilation, resulting in the restoration of a glucose⁺ phenotype and thereby increasing the carbon flow into and through a desired metabolic pathway.

A. PTS Host Cells.

A general review of the PTS can be found in (Postma et al., 1993, *Microbiol. Rev.* 57:543-594; Romano et al., 1979, *J. Bacteriol.* 139:93-97 and Saier et al. 1990, In: BACTERIAL ENERGETICS pp. 273-299, T. A. Krulwich, Ed. Academic Press, NY). Host cells or strains useful in the present invention include any organism capable of utilizing a PTS system for carbohydrate transport. This includes prokaryotes belonging to the genus *Escherichia, Corynebacterium, Brevibacterium, Bacillus, Pseudomonas, Streptomyces, Pantoea* or *Staphylococcus*. A list of suitable organisms is provided in Table 1. The inactivation of the PTS in any of these organisms should potentially increase carbon flux and PEP (and PEP precursor) availability in the cell for alternative metabolic routes and consequently could increase production of desired compounds (e.g., aromatics) from such cells.

TABLE 1

| Host cell | Reference |
|---|---|
| *Escherichia coli* | Postma, et al (1993) Microbiol. Rev. 57: 543-594 |
| *Salmonella typhimurium* | Postma, et al (1993) Microbiol. Rev. 57: 543-594 |
| *Klebsiella pneumoniae* | Postma, et al (1993) Microbiol. Rev. 57: 543-594 |
| *Bacillus subtilis* | Postma, et al (1993) Microbiol. Rev. 57: 543-594 |
| *Mycoplasma capricolum* | Postma, et al (1993) Microbiol. Rev. 57: 543-594 |
| *Acholeplasma florum* | Navas-Castillo et al. (1993) Biochimie 75: 675-679 |
| *Staphylococcus aureus* | Postma, et al (1993) Microbiol. Rev. 57: 543-594 |
| *Staphylococcus carnosus* | Postma, et al (1993) Microbiol. Rev. 57: 543-594 |
| *Staphylococcus xylosus* | Wagner et al. (1993) Mol. Gen. Genet. 24: 33-41 |

TABLE 1-continued

| Host cell | Reference |
|---|---|
| *Rhodobacter capsulatus* | Postma, et al (1993) Microbiol. Rev. 57: 543-594 |
| *Rhodopseudomonas sphaeroides* | Meadow et al. (1990) Annu. Rev. Biochem. 59: 497-542 |
| *Streptococcus (Enterococcus) faecalis* | Postma, et al (1993) Microbiol. Rev. 57: 543-594 |
| *Streptococcus mutans* | Postma, et al (1993) Microbiol. Rev. 57: 543-594 |
| *Streptococcus salivarius* | Postma, et al (1993) Microbiol. Rev. 57: 543-594 |
| *Streptococcus sanguis* | Postma, et al (1993) Microbiol. Rev. 57: 543-594 |
| *Streptococcus sobrinus* | Chen et al. (1993) Infect. Immun. 61: 2602-2610 |
| *Erwinia chrysanthemi* | Postma, et al (1993) Microbiol. Rev. 57: 543-594 |
| *Xanthmonas campestris* | Postma, et al (1993) Microbiol. Rev. 57: 543-594 |
| *Corynebacterium glutamicum* | Cocaign et al. (1993) Appl. Microbiol. and Biotechnol. 40: 526-530 |
| *Brevibacterium lactofermentum* | K-H Yoon (1993) Abstr. Ann. Meet. Am. Soc. Microbiol. 0-25 |
| *Bifidiobacterium breve* | Degnan et al. (1993) Arch. Microbiol. 160: 144-151 |
| *Azospirillum brasiliense* | Chattopadhyay et al. (1993) J. Bacteriol. 175: 3240-3243 |
| *Listeria monocytogenes* | Mitchell et al., (1993) J. Bacteriol. 175: 2758-2761. |
| *Spirocheta aurantia* | Meadow et al. (1990) Annu. Rev. Biochem. 59: 497-542 |
| *Lactobacillus brevis* | Meadow et al. (1990) Annu. Rev. Biochem. 59: 497-542 |
| *Lactobacillus buchneri* | Meadow et al. (1990) Annu. Rev. Biochem. 59: 497-542 |
| *Lactobacillus casei* | Postma, et al (1993) Microbiol. Rev. 57: 543-594 |
| *Lactococcus cremoris* | Benthin et al. (1993) Biotechnol. Bioeng. 42: 440-448 |
| *Lactococcus lactis* | Postma, et al (1993) Microbiol Rev. 57: 543-594 |
| *Pseudomonas aeruginosa* | Meadow et al. (1990) Annu. Rev. Biochem. 59: 497-542 |
| *Vibrio alginolyticus* | Postma, et al (1993) Microbiol. Rev. 57: 543-594 |
| *Vibrio furnissii* | Yu et al. (1993), J. Biol. Chem. 268: 9405-9409 |
| *Vibrio parahaemolytica* | Meadow et al. (1990) Annu. Rev. Biochem. 59: 497-542 |

Preferred host strains are those known to be useful in producing aromatic compounds, including strains selected from the genera *Escherichia, Corynebacterium, Brevibacterium, Pantoea* and *Bacillus*. The genus *Pantoea* includes all members known to those of skill in the art, including but not limited to *P. citrea, P. ananratis, P. stewarti, P. agglomerans, P. punctata* and *P. terrea*. Useful *Bacillus* strains include cells of *B. subtilis, B. licheniformis, B. lentus, B. brevis, B. stearothermophilus, B. alkalophius, B. amyloliquefaciens, B. coaglulans, B. ciculans, B. lautus* and *B. thuringiensis*.

B. Selection of PTS⁻/Glu⁻ Host Cells.

Selection of PTS⁻ cells can be achieved using techniques available to those skilled in the art. Inactivation will effectively reduce PEP phosphorylation to undetectable levels as measured by PEP-dependent phosphorylation of 2-deoxy-D-glucose using the protocols described by Gachelin, G. (1969). *Biochem. Biophys. Acta.* 34:382-387; Romero, et al., (1979) *J. Bact.* 139:93-97; or Bouvet and Grimont., (1987) *Ann. Inst. Pasteur/Microbiol.* 138:3-13. Also PEP phosphorylation assays are useful in determining the level of PTS⁻ expression.

PST⁻/Glu⁻ host cells may be selected from PTS wild-type host cells by inactivation of at least one gene encoding part or all of the enzymes comprising the PTS. By way of example, in one embodiment, the PTS is inactivated by the deletion of at least one gene selected from the group consisting of ptsI, ptsH and crr encoding the El, HPr and IIA$^{Glc}$ proteins of the PTS respectively (Postma, et al (1993) *Microbiol. Rev.* 57:543-594). In other embodiments, at least two of the genes are inactivated. The nucleotide sequences of ptsI, ptsH and crr have been determined (Saffen et al., (1987) *J. Biol. Chem.* 262:16241-16253; Fox et al., (1984) *Biochem. Soc. Trans.* 12:155-157; Weigel et al., (1982) *J. Biol. Chem.* 257:14461-14469 and DeReuse et al., (1988) *J. Bacteriol.* 176:3827-3837). In other embodiments, the inactivation of all three genes ptsI, ptsH and crr by deletion will effectively reduced PEP phosphorylation to undetectable levels.

Generally, methodology employed in the present invention to inactivate the PTS is as follows. It is known that in *E. coli* the ptsI, ptsH and crr are linked together in an operon. The ptsHIcrr operon in *E. coli* strains JM101 (Yanisch-Perron et al. (1985) *Gene* 33:103-119) and strain PB103 (Mascarenhas (1987) PCT WO87/01130) was inactivated by deletion using a generalized transduction method as described by Silhavy, et al. (1984) In: EXPERIMENTS WITH GENE FUSIONS, pp 110-112, Cold Spring Harbor Laboratory Press, NY. P1vir phage was used to perform the transduction and strain TP2811 (Levy et al., (1990) *Gene* 86:27-33) was used as the donor of the ptsHIcrr deletion. The process was carried out in two stages. First, a cell-free suspension of phage was prepared by growing bacteriophage P1vir on strain TP2811. In the TP2811 strain most of the ptsHIcrr operon has been deleted and a kanamycin-resistant marker was inserted in the same DNA region (Levy et al., (1990) *Gene* 86:27-33). The obtained P1vir lysate was able to transduce the ptsHIcrr deletion and kanamycin resistance marker simultaneously. Secondly, these phage were used to infect the recipient strains, JM101 or PB103 and transductants were selected by plating the infected cells on MacConkey-glucose plates containing kanamycin. After incubating the plates for 16 hours at 37° C., several white colonies appeared.

The recipient strains (JM101 and PB103) are kanamycin sensitive and form red colonies on MacConkey-glucose plates. The MacConkey-glucose plates contain an indicator dye that, depending on the pH, can vary from white to deep red. If the cells can transport glucose at a fast rate, normally they will secrete organic acids and produce red colonies. If glucose transport is diminished or absent, the cells will not produce organic acids and the colonies will be white. This enables one to ascertain whether the host cell exhibits a glucose$^+$ or glucose$^-$ phenotype.

Transduction of the resulting kanamycin resistant colonies were white, which indicates that the ability of the cells to assimilate glucose was affected, and it is believed this is due to the transfer of the ptsHIcrr operon deletion. To corroborate this assumption transductants can be selected and inoculated in minimal medium containing glucose as the only carbon source. One would expect after incubation (for 12 hours at 37° C.) the transductants would have no detectable cell growth and the PTS parent strains JM101 and P8103 would grow very well and reference is made to WO 96/34961. This result was observed and based on these results, the PTS$^-$ derivative of JM101 was designated PB11 and the PTS$^-$ derivative of P8103 was designated NF6.

Another test for the absence of the PTS system is based on the fact that PTS$^-$ strains become resistant to the antibiotic fosfomycin Cordaro et al., (1976) *J. Bacteriol.* 128:785-793.

While the above methodology is a preferred means of providing an inactivated PTS (PTS$^-$/Glu$^-$) other methods can also be used. One further nonlimiting method includes inserting or modifying a repressor binding region operably linked with a gene encoding an expressed protein such that the expression of the gene occurs in the presence of a specific molecule. For example, the lac operator is a DNA sequence recognized by the Lac repressor. If this operator is located in the proper position, relative to the promoter, then if the repressor is bound to the operator, it will interfere with the binding of the RNA polymerase and block gene transcription. This blockage can be removed by the addition of the inducer IPTG (isopropyl-β-D-thiogalactoside). The level of repression and/or induction will depend on the strength of the promoter, the location and sequence of the operator, as well as the amount of the repressor and the inducer (Muller J. et al., (1996) *J. Mol. Biol.* 257:21-29). The lac operator is used to regulate a number of promoters, among them several variants of the lac promoter and the hybrid trc promoter.

Another nonlimiting method to affect a PTS$^-$/Glu$^-$ phenotype includes the incorporation of a promoter which affects the expression of the structural gene sequence when certain conditions are present. For example, the Pm promoter from the TOL plasmid can be used to control gene expression. In this system, gene expression is achieved when benzoate or toluate is added to the media, (Mermod et al., (1986) *J. Bact.* 167:447-454). Still a further nonlimiting method to affect a PTS$^-$ phenotype is to alter the mRNA stability as described by Carrier and Keasling (1997) *Biotechnol. Prog.* 13:699-708.

However, to increase or redirect carbon flow to desired metabolic pathways in inactivated PTS host cells, glucose transport and phosphorylation must be deregulated or amplified.

C. Restoring the Glucose$^+$ Phenotype.

While not wanting to be limited by theory, it is thought that the modification of alternative glucose assimilation pathways compensates for the inability to actively transport glucose by the PTS, thereby allowing the host cell to utilize PEP otherwise metabolized in the transport of glucose for other purposes.

Once a PTS$^-$/Glu$^-$ host cell is obtained, a homologous chromosomal regulatory region operably linked to a chromosomal nucleic acid encoding a polypeptide involved in glucose assimilation is modified to restore a glucose$^+$ phenotype, thereby obtaining a PTS$^-$/Glu$^+$ phenotype. The regulatory region that is operably linked to the expression of the polypeptide involved in glucose assimilation can be an operator, a promoter, an inhibitor or a repressor.

In one preferred embodiment, a DNA cassette comprising a regulatory region including a promoter is introduced into a PTS$^-$/Glu$^-$ host cell and a homologous chromosomal regulatory region operably linked to a chromosomal nucleic acid encoding a polypeptide involved in glucose assimilation is modified to restore a glucose$^+$ phenotype.

D. Construction of DNA Integration Cassettes Comprising Regulatory Regions.

Typically a DNA cassette or construct according to the invention which is useful for modifying endogenous chromosomal regulatory regions in a PTS$^-$/Glu$^-$ host includes regulatory sequences, such as promoters. In another embodiment, the DNA cassette further includes a selectable marker and sequences allowing autonomous replication or chromosomal integration, such as recombinase recognition sites. In another embodiment the DNA cassette further includes flanking sequences, which are located upstream (5') and downstream (3') of the recombinase recognition sites.

Promoters—

In one embodiment, the regulatory region comprising the DNA cassette includes a promoter. In further embodiments, the promoter is an exogenous promoter. In other embodiments the exogenous promoter is a non-native promoter and derivatives thereof. In further embodiments, the promoter is a native promoter which in its native endogenous form is not operably linked to a polynucleotide encoding a glucose assimilation protein. In some embodiments the exogenous promoter is a modified naturally occurring promoter, which in its native endogenous form is linked to a polynucleotide encoding a glucose assimilation protein, wherein the native promoter has been altered and then reintroduced into a host cell chromosome. For example the native promoter could be modified at the −35 region, the −10 region or the linker region or the native promoter could include a modification of a repressor binding site. In other embodiments, the native promoter, is one that is not linked to a polynucleotide encoding a glucose transporter such as a galactose-proton symporter, and more specifically to galP. Further in other embodiments, the native promoter, is one that is not linked to a polynucleotide encoding a phosphorylating protein such as glucokinase, and more specifically is not linked to glk. A regulatory region and specifically including a promoter useful in a DNA cassette according to the invention includes sequences of between about 20 to 200 bp, of between about 20 to 150 bp and of between about 20 to 100 bp.

Preferably the promoter will be stronger that the naturally occurring endogenous wild-type promoter and will result in increased expression of the glucose assimilation protein. Those skilled in the art will recognize that various methodologies are known to determine the relative strength of the promoters. Promoter strength can be quantified using in vitro methods that measure the kinetics of binding of the RNA polymerase to a particular piece of DNA, and also allows the measurement of transcription initiation (Hawley D. K et al., Chapter 3: in: PROMOTERS: STRUCTURE AND FUNCTION. R. L/Rodriguez and M. J. Chamberlin eds. Praeger Scientific. New York). Also in vivo methods may be used also to quantify promoter strength. For example a promoter can be fused to a reporter gene and the efficiency of RNA synthesis measured. Deuschle et al., (1986) (*EMBO J.* 5: 2987-2994.) determined the strength of 14 *E. coli* promoters using 3 different reporter genes. These promoters include the following trc, tac, D/E20, H207, N25, G25, J5, A1, A2, A3, L, Lac, LacUV5, Con, β-lactamase (bla), T5"early" $P_L$, and H/McC. Each of these promoters or derivatives thereof may be used as exogenous promoters in accordance with the present invention.

Additionally, a modified naturally occurring promoter and a native promoter, which in its native endogenous form is not linked to a polynucleotide encoding a glucose assimilation protein may be used according to the invention. Native promoters may be determined by various exemplary methods. While not wanting to be limited, in one embodiment, sequencing of the particular genome may be performed and putative promoter sequences identified using computerized searching algorithms, For example a region of a genome may be sequences and analyzed for the presence of putative promoters using Neural Network for Promoter Prediction software (NNPP). NNPP is a time delayed neural network consisting mostly of two feature layers, one for recognizing TATA-boxes and one for recognizing so called, "initiators" which are regions spanning the transcription start site. Both feature layers are combined into one output unit. The putative sequences may then be cloned into a cassette suitable for preliminary characterization in *E. coli* and/or direct characterization in *E. coli*. In another embodiment, identification of consensus promoter sequences can be identified by homology analysis, for example by using BLAST. The putative promoter sequence may then be cloned into a cassette suitable for preliminary characterization in *E. coli*.

While numerous promoters and their derivatives may be used, preferred promoters include, the trc promoter and derivatives thereof (Amann et al., (1983) *Gene* 25:167-178). The trc promoter is illustrated in FIG. 2 wherein the −35 box is TTGACA and the −10 box is TATAAT. Another preferred promoter is the tac promoter. The nucleic acid sequence of the tac promoter and the trc promoter is the same with the exception of the linker region. The linker region of tac promoter differs by 1 bp. (Russell and Bennett (1982) *Gene* 20:231-243).

Another preferred promoter is a glucose isomerase (GI) promoter (also known as a xylose isomerase promoter). Reference is made to Amore et al. (1989) *Appl. Microbiol. Biotechnol.* 30:351-357. The sequence of a short segment of the GI promoter (+50 to −7 of the −10 box) is set forth in SEQ ID NO. 5 5'CGAGCCGTCACGCCC TTGACAATGCCACATCCTGAGCAAATAAT 3' wherein the −35 box is represented by TTGACA and the −10 box is represented by AATAAT.

A derivative promoter may include a modification to at least one nucleotide in a position corresponding to a nucleotide in the −35 box, linker region or −10 box. In a preferred embodiment these derivative promoters are altered in a position corresponding to a position in the −35 box. Particularly preferred derivative promoters include a modification to a −35 box corresponding to TTGACA and TTTACA. Some TTGACA modifications include TTGAAA, TTCAC and CTGACA. One particular modification is to the position corresponding to position −35. Particularly preferred derivative promoters also include a modification to a −10 box corresponding to TATAAT, TAAGAT and TATGTT. Linker regions may also be modified (Burr et al., (2000) *NAR* 28:1864-1870). Preferably linker regions whether modified or unmodified are between 14 to 20 bp in length, preferably 16 bp, 17 bp, 18 bp and 19 bp. Those skilled in the art are well aware of methods used to make modifications in promoters and the present invention is not limited by these methods. One exemplary method includes use of the Quikchange Kit (Stratagene); Reference is also made to WO 98/07846; Russell and Bennett (1982) *Gene* 231-243 and Sommer et al. (2000) *Microbiol,* 146:2643-2653.

Further preferred derivatives promoters include trc derivative promoters. The trc derivative promoter may include at least one modification in the −35 consensus box, the −10 consensus box or the linker region. The modification may be an insertion, substitution, or deletion. In a preferred embodiment the trc derivative promoter includes at least one modification to the −35 box. For example in *E. coli* since the codon at position −30 is adenine (A), it may be substituted with thymine (T), guanine (G) and cytosine (C); since the codon at position −31 is C it may be substituted with A, T and G; since the codon at position −32 is A, it may be substituted with T, G and C; since the codon at position −33 is G it may be substituted with C, T and A; since the codon at position −34 is T it may be substituted with A, C and G; and since the codon at position −35 is T, it may be substituted with A, G and C. One particularly preferred trc derivative promoter includes a modification to the codon at position −35 and most preferably a modification wherein T is substituted with C.

Other preferred trc derivative promoters include a modification in the −10 box. For example, since the nucleotide at −7 is T, it may be substituted with a nucleotide selected from the group consisting of C, G, and A.; since the nucleotide at −8 is A, it may be substituted with a nucleotide selected from the group consisting of C, G, and T; since the nucleotide at −9 is G, it may be substituted with a nucleotide selected from the group consisting of C, T, and A; since the nucleotide at −10 is A, it may be substituted with a nucleotide selected from the group consisting of C, G, and T; since −11 is A, it may be substituted with a nucleotide selected from the group consisting of T, G, and C, and since −12 is T, it may be substituted with a nucleotide selected from the group consisting of A, C, and G.

Selective Markers and Recombinase Recognition Sites—

A DNA cassette encompassed by the invention will include a selectable marker and a number of genes can be used to detect insertion of the gene in *E. coli*. Some of these genes confer selectable phenotypes. In this case, media conditions can be established so that only colonies which have expression of these genes activated will grow. Other genes confer phenotypes which can be screened. A screenable phenotype can often yield information about levels of gene expression. While any desired marker can be used, based on these properties, useful antibiotic resistance ($Anb^R$) markers include but are not limited to, $Cm^R$, $Km^R$ and $Gm^R$. A preferred non-limiting example of a selectable marker is a chloramphenicol acetyltransferase (CAT) gene.

In a preferred embodiment, a DNA cassette comprising the promoter to be integrated into a host cell chromosome at a target site will include a selectable marker flanked on both sides by a recombinase recognition site. Recombinase sites are well known in the art and generally fall into two distinct families based on their mechanism of catalysis and reference is made to Huang et al., (1991) *NAR*, 19:443; Datsenko and Warner (2000) *Proc. Natl. Acad. Sci.* 97:6640-6645 and Nunes-Duby, D, et al (1998) *NAR* 26:391-406. Preferably the recognition sites are the same.

One well known recombination system is the *Saccharomyces* Flp/FRT recombination system, which comprises a Flp enzyme and two asymmetric 34 bp FRT minimum recombination sites (Zhu et al., (1995) *J. Biol. Chem* 270:11646-11653). A FRT site comprises two 13 bp sequence inverted and imperfectly repeated, which surround an 8 bp core asymmetric sequence where crossing-over occurs. (Huffman et al., (1999) *J. Mol. Biol.* 286:1-13)

One preferred recombinase system is the Cre/loxP site-specific recombination system of bacteriophage P1, which comprises a Cre enzyme and two asymmetric 34 bp loxP recombination sites (Sternberg and Hamilton (1981) *J. Mol. Biol.* 150:467-486); Palmeros, B, et al. (2000) *Gene* 247:255-264; Hoess et al. (1986) *NAR* 14:2287-2300; Sauer B. (1994) *Curr. Opinions in Biotechnol.* 5:521-527). A loxP site comprises two 13 bp sequences, inverted and imperfectly repeated, which surround an 8 bp core asymmetric sequence, where crossing-over occurs. The Cre-dependent intramolecular recombination between two parallel loxP sites results is excision of any intervening DNA sequence as a circular molecule, producing two recombination products, each containing one loxP site (Kilby et al., (1993) *Trends Genet.* 9:414-421).

Homologous Flanking Regions—

An integration DNA cassette according to the invention may also include nucleic acid sequences homologous to upstream (5') regions of a gene encoding a glucose assimilation protein. These homologous sequences will preferably flank the first recombinase recognition site (5' thereto) and the promoter (3' thereto). Nucleic acid sequences homologous to upstream (5') regions of a gene encoding a glucose assimilation protein include sequences derived from a) a sequence 5' to the endogenous regulatory region that is targeted for modification, and b) a sequence 3' of the endogenous regulatory region that is targeted for modification. The 3' sequence may include parts of a glucose assimilation protein coding sequence. A homologous flanking sequence may include from about 2 to 300 bp, about 5 to 200 bp, about 5 to 150 bp, about 5 to 100 bp and about 5 to 50 bp.

Isolation of Genes and Glucose Assimilation Proteins—

Methods of obtaining a desired gene from bacterial cells are common and well known in the art of molecular biology. For example, if a sequence of a gene is known, suitable genomic libraries may be created and screened. Once a sequence is isolated the DNA may be amplified using standard techniques such as polymerase chain reaction (PCR) (U.S. Pat. No. 4,683,202) to obtain amounts of DNA by restriction. Also reference is made to Sambrook et al., suprae For the purpose of the present invention, upstream sequences as defined above of any gene encoding a glucose assimilation protein is suitable for use in the disclosed methods.

In one embodiment, a gene encoding a glucose assimilation protein is a glucose transporter. Transporters are discussed in Saier et al., (1998) ADVANCES IN MICROBIAL PHYSIOLOGY, Poole, R. K. Ed. pp 81-136 Academic press, San Diego, Calif. In general, the glucose transporters as defined herein fail with the Transport Council (TC) classification of transport class 2 (GALP) and/or transport class 4 (PTS).

A preferred glucose transporter is GalP, which is encoded by galP in *E. coli*. One of skill in the art will appreciate that genes encoding GalP isolated from sources other than *E. coli* will also be suitable for use in the present invention. Moreover, proteins functioning as glucose transporters and having at least 20%, 30%, 35%, 40%, 45%, 50%, 55%, 60%, 65%, 70%, 75%, 80%, 85%, 90%, 95%, 97% and 98% amino acid sequence identity to GalP from *E. coli* will be suitable for use according to the invention.

Additionally publicly available computer programs can be used to determine sequences with identity to a glucose assimilation protein and specifically to a glucose transporter. Preferred programs include the GCG Pileup program, FASTA (Pearson et al. (1988) *Proc. Nat. Aced. Sci. USA* 85:2444-2448) and BLAST (*BLAST Manuael*, Altschul et al., Natl. Cent. Biotechnol. Inf., Natl Library Med. (NCBI NLM), NIH, Bethesda Md. and Altschul et al., (1997) *NAR* 25:3389-3402).

By using BLAST at least 3 permeases with protein sequence similarity to GalP have been found. For example, areE with 64% protein sequence identity; xylE with 34% protein sequence identity and yaaU with 23% protein sequence identity. These peremases may also function as glucose transporters.

In many cases, transporter proteins are highly regulated in cells and commonly the expression of transporter genes is induced by the presence of a substrate in the media. The glucose transporter, galactose permease (GalP) from *E. coli* is induced by galactose, but the preferred substrate is glucose (Henderson & Maidenn (1990). *Phil. Trans. R. Soc. Lond.* 326: 391-410). In *E. coli*, besides GalP, other permeases can recognize and transport glucose, for example:

(a) the high affinity galactose transport system encoded by the mglBCA genes (Hogg et al. (1991) *Mol. Gen. Genet.* 229:453-459 and Ferenci T. (1996) *FEMS Microbiol. Rev.* 18:301-317); and (b) the mannose PTS system, where the membrane component PtsM has a broad substrate specificity and is capable of transporting glucose and fructose (Postma & Lengeler (1985) *Microbial Rev.* 49:232-269 and Erni et al., (1987) *J. Biol. Chem.* 262:5238-5247).

Further the product of the ptsG gene, which normally is part of the glucose-PTS system, can be converted by mutagenesis to a PTS-independent transporter, that functions as a glucose assimilation protein and more specifically as a glucose-facilitator. (Ruijter et al (1992) *J. Bact.* 174: 2843-2850 and Erni et al (1986) *J. Biol. Chem.* 261:16398-16403).

Besides the well characterized examples above, other glucose transporters include those cataloged in the TransportDB database. This is a relational database describing the predicted cytoplasmic membrane transport protein complement for organisms whose complete genome sequence is available (http://66.93.129.133/transporter/wb/index.html).

In another embodiment, the glucose assimilation protein is a phosphorylating protein. The phosphorylating protein may be a hexokinase and preferably is a glucokinase. One preferred glucokinase is Glk and reference is made to NCBI (NC 000913). As indicated above for glucose transporters, other glucose phosphorylating enzymes may be identified using the computer programs such as FASTA, GCG Pileup and BLASTA.

*E. coli* includes other glucose phosphorylating enzymes as suggested by the result of Flores et al. (2002) *Met. Eng.* 4:124-137 and Curtis et al. (1975) J. Bacteriol, 122:1189-1199). When glk was interrupted in *E. coli*, the cells had a residual glucose phosphorylating activity of 22 to 32% compared to a wild-type strain. A BLAST search of the *E. coli* genome using the Glk sequence, did not showed any protein with a level of sequence identity of greater than 34%. This may indicate that the measured glucokinase activity depends on one or more enzyme(s) not or distantly related to Glk. Some of these glucose assimilation proteins which may contribute to glucokinase activity are listed below:

| Gene name | Current annotation in the NCBI database | |
|---|---|---|
| gntK | gluconate kinase 2 | NP 417894 |
| idnK | gluconate kinase | NP 418689 |
| kdgK | Ketodeoxygluconokinase | NP 417983 |
| galK | Galactokinase | NP 415278 |
| pfkA | 6-phosphofructokinase | NP 418351 |
| rbsK | ribokinase | NP 418208 |
| fruK | 1-phosphofructokinase | NP 416673 |
| yoaC(b1511) | putative kinase | NP 416028 |
| yajF(b0394) | possible transcriptional regulator | NP 414928 |
| ycfX(b1119) | putative transcriptional regulator | NP 415637 |
| fucI | L-fuculokinase | NP 417283 |

This list is not exhaustive, and it is suggested by the inventors that by using the proper mutagenesis-selection protocols, these and/or other kinases can be modified to increase their ability to phosphorylate glucose.

E. Introduction of DNA Cassettes into PTS⁻/Glu⁻ Cells—

Once suitable DNA cassettes are constructed they may be introduced into plasmids or directly used to transform appropriate PTS⁻/Glu⁻ host cells. Plasmids which can be used as vectors in bacterial organisms are well known and reference is made to Maniatis, et al., MOLECULAR CLONING: A LABORATORY MANUAL, 2d Edition (1989) AND MOLECULAR CLONING: A LABORATORY MANUAL, second edition (Sambrook et al., 1989) and Bron, S, Chapter 3, Plasmids, in MOLECULAR BIOLOGY METHODS FOR BACILLUS, Ed. Harwood and Cutting, (1990) John Wiley & Sons Ltd.

Useful vectors in the present invention include the vectors pSYCO101 (FIGS. 8 and 9), and the pSYCO 101 derivative plasmids pSYCO103 and pSYCO106; pKD46; pR6K-ECHO (Invitrogen); pJW168 (Palmeros et al., 2000 *Gene,* 247:255-264); ptrcM2; ptrc99A; pTrc99 (Pharmacia); pACYC177; pMCGG; pSC101; pKD46 (Datsenko and Wanner (2000) *PNAS* 97:6640-6645); and pKP32 WO 01/012833).

Introduction of a DNA cassette and other vectors into a host cell may be accomplished by known transfer techniques. These gene transfer techniques include transformation, transduction, conjugation and protoplast fusion. Gene transfer is the process of transferring a gene or polynucleotide to a cell or cells wherein exogenously added DNA is taken up by a bacterium. General transformation procedures are taught in CURRENT PROTOCOLS IN MOLECULAR BIOLOGY (vol. 1, edited by Ausubel et al., John Wiley & Sons, Inc. 1987, Chapter 9) and include calcium phosphate methods, transformation using DEAE-Dextran and electroporation. A variety of transformation procedures are known by those of skill in the art for introducing nucleic acids in a given host cell. (Reference is also made to U.S. Pat. No. 5,032,514; Potter H. (1988) *Anal, Biochem* 174:361-373; Sambrook, J. et al., MOLECULAR CLONING: A LABORATORY MANUAL, Cold Spring Harbor Laboratory Press (1989); and Ferrari et al., Genetics, pgs 57-72 in BACILLUS, Harwood et al., Eds. Plenum Publishing Corp).

The introduction of a DNA cassette comprising a promoter and upstream sequences of a gene encoding a glucose assimilation protein into a PTS⁻/Glu⁻ host cell results in modification of the endogenous chromosomal regulatory region, preferably by replacement of the endogenous regulatory region. In one embodiment, the DNA cassette includes an exogenous promoter and the promoter of the endogenous regulatory region is replaced. The introduced regulatory sequence (including the promoter) is chromosomally integrated into the PTS⁻/Glu⁻ cell and the introduced sequence becomes operably linked with a coding sequence of the glucose assimilation protein replacing endogenous regulatory sequences. In a preferred embodiment, a selectable marker gene, which was introduced with the integrating DNA cassette is removed, preferably by using the methods described in Palmeros et al. (2000) *Gene* 247:255-264. The expression of the glucose assimilation protein, which is linked to the exogenous promoter, results in a cell having a glucose⁺ phenotype. Bacterial strains having a glucose⁺ phenotype (PTS⁻/Glu⁺), as disclosed herein are also encompassed by the present invention.

In a further embodiment, the modified endogenous regulatory region is the regulatory region of a glucose transporter. In a preferred embodiment, the glucose transporter gene encodes GalP from *E. coli* and glucose transporters having at least 60%, 70%, 75%, 80%, 85%, 90%, 95%, 97% and 98% amino acid sequence identity to GalP from *E. coli*. In another embodiment, the modified endogenous regulatory region is the regulatory region of a phosphorylating protein. In a preferred embodiment, the phosphorylating protein is a glucokinase and more preferrably a Glk from *E. coli* and phosphorylating proteins having at least 60%, 70%, 75%, 80%, 85%, 90%, 95%, 97% and 98% amino acid sequence identity to Glk from *E. coli*.

In one embodiment, the obtained PTS⁻/Glu⁺ cells having a modified endogenous regulatory sequence operably linked to a glucose assimilation protein, and particularly to a modified endogenous regulatory sequence operably linked to a galactose permease and a modified endogenous regulatory sequence operably linked to a glucokinase according to the invention, will be capable of increased production of a desired compound compared to a wild type host cell. The desired compounds include the compounds illustrated in FIG. 1B. Particularly preferred compounds include dihydroxyacetone-P, glycerol, 1,3-propanediol, pyruvate, lactate, chorismate, tryptophan, phenylalanine, tyrosine, oxaloacetate, aspartate, asparagine, tyrosine, succinate, ethanol, and acetyl-CoA. In particular the desired compounds include pyruvate, chorismate and succinate.

F. Further Modifications of PTS⁻/Glu⁺ Cells—

The PTS⁻/Glu⁺ cells obtained according to the method of the invention may further include heterologous polynucleotides encoding one or more proteins which direct carbon flow into and through the common aromatic pathway. The heterologous polynucleotide may be introduced into a PTS⁻/Glu⁺ cell either prior to, during or following the reversion to a Glu⁺ phenotype.

In one embodiment a PTS⁻/Glu⁺ cell according to the invention may overexpress a transketolase, which is encoded by a tktA or tktB. Transketolase is a pentose phosphate pathway enzyme that catalyzes two separate reactions each of which produces E4P as a product. (See FIG. 1). Amplification (overexpression) of the tktA gene, by introduction of nucleic acid sequences encoding transketolase may result in an increase in intracellular concentrations of the aromatic precursor E4P (U.S. Pat. No. 5,168,056).

In another embodiment, one or more of the genes (aroG, aroF and aroH) encoding DAHP synthase may be introduced or amplified in a PTS⁻/Glu⁺ cell according to the invention. The increased expression of both E4P and DAHP synthase can result in a significant increase in carbon committed to the aromatic pathway compared to strains containing elevated DAHP synthase activity alone (U.S. Pat. No. 5,168,056).

Thus in one embodiment the invention concerns a host cell which creates a surge of carbon flow due to the amplification of transketolase in addition to a host cell which conserves PEP via inactivation of the PTS (PTS⁻).

It should be noted that as the host cell is cultured in conditions which create an increase in carbon flow into the aromatic pathway, it may be necessary to identify and overcome rate-limiting steps in the pathway. This methodology is available to the artisan, see, for example, U.S. Pat. Nos. 5,168,056 and 5,776,736.

As an example, in the following conversion

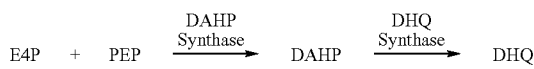

under conditions that create a surge of carbon flow into the pathway of, for example PTS⁻/Glu⁺ and Tkt overexpressed strains, the activity level of DHQ synthase is insufficient to consume DAHP as fast as it is formed. As a result of this natural rate-limiting step at aroB, DAHP accumulates and is excreted into the culture supernatant. This allows DAHP accumulation to be used as a means of testing the increased intracellular PEP levels resulting from the PTS⁻/Glu⁺ strains.

In addition to increasing the carbon flux through the aromatic pathway, the following genes may be overexpressed in PTS⁻/Glu⁺ cells according to the invention: pps which encodes PEP synthase in E. coli (see U.S. Pat. No. 5,985,617) and talA which encodes transaldolase (Iida et al. (1993) J. Bacterial. 175:5375-5383). Further any gene encoding an enzyme that catalyzes reactions within the common aromatic pathway (for example, DAHP synthase (aroF, aroG, aroH), DHQ synthase (aroB), DHQ dehydratase (aroD), shikimate dehydrogenase (aroE), shikimate kinase (aroL, aroK), EPSP synthase (aroA) and chorismate synthase (aroC) may be amplified in the PTS⁻/Glu⁺ cells encompassed by the present invention.

It will be readily apparent to those skilled in the art, that a variety of different genes can be overexpressed depending on the desired product.

In one embodiment, if the desired product is chorismate, a PTS⁻/Glu⁺ cell according to the invention may overexpress any one of the genes in the aromatic pathway including the genes coding for the enzymes DAHP synthase, DHQ synthase; DHQ dehydratase; shikimate dehydrogenase; shikimate kinase; EPSP synthase and chorismate synthase.

In one embodiment, if the desired product is tryptophan, any of the genes in the tryptophan-specific segment of the aromatic pathway may be amplified, including the genes coding for the enzymes tryptophan synthase (trpA and trpB), phosphoribosyl anthranilate isomerase-indoleglycerol phosphate synthase (trpC), anthranilate phosphoribosyl transferase (trpD) and anthranilate synthase (trpE). In another embodiment the gene (tnaA) encoding tryptophanase may be deleted.

In another embodiment, if the desired product is pyruvate a PTS⁻/Glu⁺ cell according to the invention may be genetically engineered to overexpress pyk. This gene encodes a pyruvate kinase. If the desired compound is oxaloacetate a PTS⁻/Glu⁺ cell according to the invention may be genetically engineered to overexpress a ppc which encodes a PEP carboxylase (EC 4.1.1.31).

If the desired compound is catechol, the PTS⁻/Glu⁺ cell according to the invention may be further transformed with DNA encoding one or more of the following enzyme(s): DAHP synthase (aroF, aroG, aroH); 3-dehydroquinate (DHQ) synthase (aroB); transketolase (tktA or tktB); 3-dehydroshikimate (DHS) dehydratase (aroZ) or protocatechuate (PCA) decarboxylase (aroY) (see U.S. Pat. Nos. 5,272,073 and 5,629,181).

Furthermore, by way of example, if the desired product is adipic acid, one or more of the following enzyme(s) may be overexpressed (by amplification of the corresponding gene): 3-dehydroshikimate (DHS) dehydratase (aroZ); protocatechuate (PCA) decarboxylase (aroY) or catechol 1,2-dioxygenase (catA); and, optionally, transketolase (tktA or tktB); DAHP synthase (aroF, aroG, aroH) or DHQ synthase (aroB) in a PTS⁻/Glu⁺ cell according to the invention. (See U.S. Pat. No. 5,487,987).

If the desired product is indigo, the PTS⁻/Glu⁺ cell according to the invention may be further transformed with DNA encoding a polypeptide analog of a tryptophan synthase beta-subunit and DNA encoding an aromatic dioxygenase enzyme. (See U.S. Pat. No. 5,374,543).

Thus, having provided a PTS⁻/Glu⁺ strain which conserves PEP resulting in an increase in carbon flux into a metabolic pathway, such as the aromatic amino acid pathway, glycolysis, the TCA cycle, and the pentose phosphate pathway, by redirecting PEP and PEP precursors, the inventors have provided a host system which can be utilized for enhanced production of desired compounds in comparison to the production of the same compounds in a corresponding PTS host cell.

G. Cell Cultures and Fermentations—

Methods suitable for the maintenance and growth of bacterial cells are well known and reference is made to the MANUAL OF METHODS OF GENERAL BACTERIOLOGY, Eds. P. Gerhardt et al., American Society for Microbiology, Washington D.C. (1981) and T. D. Brock in BIOTECHNOLOGY: A TEXTBOOK OF INDUSTRIAL MICROBIOLOGY, 2nd ed. (1989) Sinauer Associates, Sunderland, Mass.

Cell Precultures

Typically cell cultures are grown at 25 to 32° C., and preferably about 28 or 29° C. in appropriate media. Exemplary growth media useful in the present invention are common commercially prepared media such as but not limited to Luria Bertani (LB) broth, Sabouraud Dextrose (SD) broth or Yeast medium (YM) broth. These may be obtained from for example, GIBCO/BRL (Gaithersburg, Md.). Other defined or synthetic growth media may be used and the appropriate medium for growth of the particular bacterial microorganism will be known by one skilled in the art of microbiology or fermentation science. Suitable pH ranges preferred for the fermentation are between pH 5 to pH 8. Preferred ranges for seed flasks are pH 7 to pH 7.5 and preferred ranges for the reactor vessels are pH 5 to pH 6. It will be appreciated by one of skill in the art of fermentation microbiology that a number of factors affecting the fermentation processes may have to be optimized and controlled in order to maximize the ascorbic acid intermediate production. Many of these factors such as pH, carbon source concentration, and dissolved oxygen levels may affect enzymatic processes depending on the cell types used for ascorbic acid intermediate production.

The production of desired products can proceed in a fermentative environment, that is, in an in vivo environment, or a non-fermentative environment, that is, in an in vitro environment; or combined in vivo/in vitro environments. The fermentation or bioreactor may be performed in a batch process or in a continuous process.

Fermentation Media

Fermentation media in the present invention must contain suitable carbon substrates which will include but are not limited to monosaccharides such as glucose, oligosaccharides such as lactose or sucrose, polysaccharides such as starch or cellulose and unpurified mixtures from a renewable feedstocks such as cheese whey permeate, cornsteep liquor, sugar beet molasses, and barley malt. Additionally the carbon substrate may also be one-carbon substrates such as carbon. While it is contemplated that the source of carbon utilized in the present invention may encompass a wide variety of carbon containing substrates and will only be limited by the choice of organism, the preferred carbon substrates include glucose and/or fructose and mixtures thereof. By using mixtures of glucose and fructose in combination with the modified genomes described elsewhere in this application, uncoupling of the oxidative pathways from the catabolic pathways allows the use of glucose for improved yield and conversion to the desired ascorbic acid intermediate while utilizing the fructose to satisfy the metabolic requirements of the host cells.

Although it is contemplated that all of the above mentioned carbon substrates are suitable in the present invention preferred are the carbohydrates glucose, fructose or sucrose. The concentration of the carbon substrate is from about 55% to about 75% on a weight/weight basis. Preferably, the concentration is from about 60 to about 70% on a weight/weight basis. The inventors most preferably used 60% or 67% glucose.

In addition to an appropriate carbon source, fermentation media must contain suitable minerals, salts, vitamins, cofactors and buffers suitable for the growth or the cultures and promotion of the enzymatic pathway necessary for ascorbic acid intermediate production.

Batch and Continuous Fermentations

The present process employs either a batch, fed-batch or continuous fermentation method for its culture systems. These methods are well known in the art and examples may be found in Brock, supra. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Although in the present invention a batch or fed-batch method is preferred, a continuous fermentation method may also be used. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXPERIMENTAL

Example 1

Construction of PTS⁻ E. coli Strains with trc Promoters

A). Construction of the loxP-CAT-loxP-trc Cassette, Plasmid pTrcM42.

Linear DNA was obtained from plasmid pTrc99a (Pharmacia) digested with the restriction enzymes HindIII and NcoI according to the suppliers instructions (New England Biolabs). After purification, the ends of the digested DNA were filled by T4DNA polymerase as described by Sambrook et al. supra. The resulting blunt-end, linear DNA was circularized according standard protocols and transformed into E. coli TOP-10 competent cells (Invitrogen, Carlsbad, Calif.). Cells were plated on Luria-agar (LA) plates (LB medium containing 5 g/L yeast extract; 10 g/L tryptone, and 10 g/L NaCl plus 2% agar) containing 50 micrograms/ml of carbenicillin. After 16 hrs. of incubation at 37° C., four colonies were chosen for further analysis. Purified plasmid DNA was obtained from these colonies and subjected to restriction enzymes analysis. It was confirmed that the 4 colonies contained the same plasmid and that the DNA region between HindIII and NcoI was deleted. The resulting plasmid was named pTrc1.

Plasmid pTrc1 contains only one recognition site for the restriction enzyme BspM1, located approximately 120 bp upstream of the −35 region of the trc promoter. That location was selected to introduce an excisable selectable marker. pTrc1 was digested with the BspM1 enzyme according to the instructions of the supplier (New England Biolabs). The linear pTrc1 was gel-purified using a QIAquick gel extraction kit (QIAGEN), filled in with T4 DNA polymerase as described by Sambrook, supra, and ligated to a loxP-CAT-loxP DNA cassette. The loxP-CAT-loxP DNA cassette was obtained from plasmid pLoxCAT2 (Palmeros et al., (2000) *Gene* 247: 255-264) digested with Stu1 and Bam H1. The ligation mixture was transformed into *E. coli* TOP-10 competent cells (Invitrogen) and plated on Luria-agar plates containing 50 micrograms/ml of carbenicillin and 20 micrograms/ml of chloramphenicol. After 16 hrs of incubation at 37° C., several colonies appeared on the plate. Some of these colonies were transferred to a fresh LB plate containing carbenicillin and chloramphenicol. After plasmid purification and restriction enzyme analysis, two plasmids containing the loxP-CAT-loxP-trc with the loxP-CAT-loxP cassette in the same and in the opposite orientation relative to the trc promoter were selected and designated pTrcm41 and pTrcm42 (FIG. 6).

B). Construction of a trc Promoter Replacement Template for galP (pR6KgalP)

A DNA cassette containing the trc promoter and lac operator with an upstream loxP-CAT-loxP cassette was amplified by PCR from pTrcm42 using the primer set of GalA/GalP2

```
GalA:                                          (SEQ ID NO. 6)
5' TCGGTTTTCACAGTTGTTACATTTCTTTTCAGTAAAGTCTGGATGCA

TATGGCGGCCGCAT 3'

GaLP2:                                         (SEQ ID NO. 7)
5' CATGATGCCCTCCAATATGGTTATTTTTTATTGTGAATTAGTCTGTT

TCCTGTGTGAAATTGTTA. 3'
```

The primer pair incorporated 40 bp of homology to the galP upstream region to each end of the PCR product. The amplification used 30 cycles of (95° C. for 1 min; 55° C. for 1 min; 72° C. for 2 min) using Taq polymerase (Roche). This DNA cassette was cloned into Echo pUni/His5 R6K vector (Invitrogen) and transformed into *E. coli* Pir1 cells. Positive clones were confirmed by restriction enzyme digest to release the fragment. This construct was designated pR6KgalP.

C). Construction of a trc Promoter Replacement Template for glk (pR6Kglk).

A DNA cassette containing the trc promoter and lac operator with an upstream loxP-CAT-loxP cassette was amplified by PCR from pTrcm42 using the primer set of GlkA/Glk2.

```
GlkA:                                          (SEQ ID NO. 8)
5'-ACTTAGTTTGCCCAGCTTGCAAAAGGCATCGCTGCAATTGGATGCAT

ATGGCGGCCGCAT 3'

Glk2:                                          (SEQ ID NO. 9)
5'-CATTCTTCAACTGCTCCGCTAAAGTCAAAATAATTCTTTCTCGTCTG

TTTCCTGTGTGAAATTGTTA 3'
```

The primer pair incorporated 40 bp of homology to the glk upstream region to each end of the PCR product. The amplification used 30 cycles of (95° C. for 1 min; 55° C. for 1 min; 72° C. for 2 min) using Taq polymerase (Roche). This DNA cassette was cloned into Echo pUni/His5 R6K vector (Invitrogen) and transformed into *E. coli* Pir1 cells. Positive clones were confirmed by restriction enzymes and the plasmid was designated pR6Kglk D). Construction of an *E. coli* ptsHIcrr Deletion Strain KLpts7

A PTS⁻ (Δ ptsHIcrr) strain of *E. coli* KLndh81 (KLp23ndh), was obtained by replacing the entire operon comprising ptsH, ptst and crr with a kanamycin resistance marker (Levy et al., (1990) *Gene* 86:27-33). This was done by P1vir transduction using the phage lysate 2611 NF9pykF:: Gm as described in Flores et al., (1996) *Nature Biotechnol.*, 14:620-623. The deletion of the operon was confirmed by amplification of the region by PCR with primers (ptsHF/crrR) that hybridized to regions upstream or downstream of the deletion, and by plating the colonies on MacConkey (lactose⁻) agar+1% glucose.

```
ptsHF                                         (SEQ ID NO. 23)
5' AGAATTGCAACAGTAATGCCAGCTTGTTAAAAATGCGTA 3' crrR                                          (SEQ ID NO.24)
5' CCTGTTTTGTGCTCAGCTCATCAGTGGCTTGCTGAA 3'
```

Those colonies with a deletion in the glucose::PTS system exhibited a white phenotype on these plates as they were no longer able to utilize the glucose and as generate acid. This strain was designated KLpts7.

E). Replacement of the Natural Promoter of galP with the Synthetic Exogenous trc Promoter by Linear DNA Cassette Transformation.

A DNA cassette comprising a loxP-CAT-loxP-ptrc with 40 bp of flanking DNA on each end with homology to the *E. coli* galP upstream region was generated using rTth RNA polymerase (Perkin Elmer), pR6K-galP (SEQ ID NO. 1) as the template and the primer pairs GalA/GalP2 (SEQ ID NO. 6/SEQ ID NO. 7). The PCR product was transformed into electro-competent KLpts7 cells containing pKD46 for integration using the lambda Red system as described in Datsenko and Wanner (2000), *Proc. Natl. Acad. Sci. USA* 97:6640-6645. Integration of this cassette resulted in the replacement of the regulatory region from 36-183 bp upstream of the galP ATG start codon. (For reference see GenBank Accession # U28377) with a loxP-CAT-loxP-ptrc cassette to provide strain KLpts::galP-trc.

Colonies were selected on LA plates containing 10 µg/ml chloramphenicol. The integration was confirmed by PCR analysis using the primer pair GalA/GalP2 (SEQ ID NO.6/SEQ ID NO. 7) (amplifying the integration site to give a 1.4 kb product) and the primer pair GalB1/GalC11 (amplifying the integration site, including upstream and downstream regions to give a 2.1 kb product).

```
GalB1                                         (SEQ ID NO. 10)
5' ACTTTGGTCGTGAACATTTCCCGTGGGAAA 3'

GalC11                                        (SEQ ID NO. 11)
5' AGAAAGATAAGCACCGAGGATCCCGATA 3'
```

PCR parameters were 1 min at 95° C.; 1 min at 55° C.; 2 min at 72° C., 30 cycles using Taq DNA polymerase or rtth polymerase as suggested by the manufacturer. This strain, KLpts:: galP-trc, was plated on MacConkey agar (lactose⁻)+1% glucose. The colonies exhibited a slightly red phenotype compared to KLpts7 which was white, indicating that the former strain was able to make acid from glucose while the latter strain (parent) was not. This confirmed the expression of galP and that the GalP allowed uptake of glucose. The promoter region was sequenced to confirm the presence of the promoter. The chloramphenicol marker was removed using the Cre recombinase as described in (Palmeros et al., (2000) *Gene* 247:255-264 and the removal was confirmed by PCR using the primer set GalB1/GalC11 (SEQ ID NO. 10/SEQ ID NO. 11). The resultant strain was designated KLgalP-ptrc.

F). Replacement of the Natural Glucokinase Promoter with the Synthetic Exogenous trc Promoter (KLGG) by Linear DNA Cassette Transformation.

A DNA cassette consisting of loxP-CAT-loxP-ptrc with 40 bp of flanking DNA with homology to the upstream region of glk was prepared as described for the galP DNA cassette in example 1E) above. The primer set used was GlkA/Glk2 (SEQ ID NO. 8 and SEQ ID NO. 9) that adds the flanking DNA from 149-189 upstream of the glk ATG to the 5' end and from glk ATG to 37 bp upstream of the ATG to the 3' end (glk accession number AE000327). The template used for the PCR amplification was pR6Kglk with the rTth polymerase (Perkin Elmer). The glk-trc DNA cassette was transformed into electro-competent KLgalP-trc cells containing the pKD46 plasmid as described by Datsenko and Wanner (2000) supra. Positive clones were selected on LA agar containing 10 μg/ml chloramphenicol. Integration of the cassette was confirmed by PCR using the primer set GlkB1/GlkC11 and the PCR program described in construction of KLgalP-trc. GlkB1 is the forward primer that binds beginning at 700 bp upstream of the glk ATG and GlkC11 binds beginning at 500 bp downstream of the glk ATG start codon.

```
GlkB1                              (SEQ ID NO. 12)
5' AACAGGAGTGCCAAACAGTGCGCCGA 3'

GlkC11
                                   (SEQ ID NO. 13)
5' CTATTCGGCGCAAAATCAACGTGACCGCCT 3'
```

Colonies were plated onto MacConkey agar (lactose-)+1% glucose. Colonies exhibited a deep red color, indicating an increase in the conversion of glucose to acid compared to the parent (KLgalP-trc). The chloramphenicol marker was removed using the Cre recombinase as described in Palmeros et al., supra and removal was confirmed by PCR using the primer set GlkB1/GlkC11 to give a 1.3 kb product. The resultant strain was designated KLGG.

G). Construction of the PEP-Independent Glucose Transport System from ptrc Cloned into pACYC177 (pMCGG).

A moderate copy number plasmid that allowed expression of galP and glk from the trc promoter was constructed. A 3040 bp AccI fragment containing galP and glk each under the control of trc promoters was isolated from plasmid pVH-GalPglk11 (FIG. 13). Plasmid pVHGalPglk11 is a low copy number plasmid derived from the pCL1920 vector (Lerner et al. (1990) *NAR* 18:4631) that carries the resistance to the Spectinomycin antibiotic and the galP and glk genes from *E. coli* under the control of trc promoters. The nucleotide sequence (SEQ ID NO. 25) of the 3040 bp DNA fragment obtained by AccI digestion is illustrated in FIG. 14A-E. The ends were filled in using standard procedures (Sambrook et al., supra), This blunt-ended fragment was cloned into the ClaI site of pACYC177 (New England Biolabs) thereby inactivating the kanamycin resistance gene. Colonies were screened for growth on carbenicillin (100 micrograms/ml) and lack of growth on kanamycin (10 micrograms/ml). Plasmid DNA was isolated from a positive clone by standard method and the presence of the desired fragment was confirmed by restriction enzyme digestion using XbaI which cuts only 1 time within the cloned fragment, and separately with BamHI which has two recognition sites in the plasmid. This enabled the inventors to determine the orientation of the inserted fragment. This plasmid was designated pMCGG.

H). Construction of the pSYCO Constructs.

The utility of the PTS$^-$/Glu$^+$ strains (examples 1E-G) to convert carbon from glucose to a product was tested by plasmids carrying genes encoding enzymes that carry out conversion of DHAP to 1, 3 propanediol. The pSYCO constructs were pSC101 (Stratagene) based plasmids that carry genes for conversion of DHAP (dihydroxyacetone-P) to glycerol (dar1 and gpp2) from *Saccharomyces cerevisiae* (referred to as the glycerol pathway) and subsequently glycerol to 1,3-propanediol (dhaB1-3, dhaX, orfW, X, and Y from *Klebsiella*, (referred to as the 1,3-propanediol pathway). The pSYCO constructs used in the current examples were pSYCO101, 103 and 106 and reference is made to FIGS. 8 and 9 which depict the nucleotide sequence and plasmid map of pSYCO 101, respectively. The pSYCO103 construct is identical to pSYCO101 except the DNA region which includes the glycerol pathway genes and the two EcoR1 sites in the opposite orientation to that of pSYCO101. The pSYCO106 construct is identical to pSYCO103 except for the removal of the 126 bp of non-coding plasmid DNA between the EcoR1 sites and bp 10589-11145 as indicated in FIG. 9. For the experiments described herein, the plasmids are functionally equivalent.

Example 2

Constitutive Expression of galP Encoding Galactose Permease from the Chromosome of a Strain Lacking a PEP-PTS System for Glucose Uptake The production of glycerol and 1,3-propanediol in an PTS$^-$/Glu$^+$ *E. coli* strain having a Glu+ phenotype was determined. The PTS$^-$/Glu$^+$ *E. coli* strain was obtained by transformation of the PTS$^-$/Glu$^-$ strain (KLpts7) with pMCGG (example 1G) by standard procedures (Sambrook et al. supra) to create KLpts7/pMCGG or by chromosomal integration of the trc promoter to replace the endogenous native galP promoter in KLpts7 creating a KlgalP-ptrc (example 1E). Both KLpts7/pMCGG and KlgalP-ptrc were transformed by standard procedures (Sambrook et al., supra) with a plasmid carrying the pathways for glycerol and 1,3-propanediol production. The production of cell mass, glycerol and 1,3-propanediol was tested in fermentations.

A standard fermentation was carried out as follows: A 500 ml seed flask was grown at 35° C. in standard 2YT medium (Sambrook et al. supra) for 4-6 hours with shaking at 200 rpm. This seed culture was used to incubate a 14 L fermentor which was run in glucose excess conditions at 35° C., pH 6.8, for 60 h in a TN2 medium consisting of—

(g/L): $K_2HPO_4$ (13.6); $KH_2PO_4$ (13.6): $MgSO_4.7H_2O$ (2); citric acid monohydrate (2), ferric ammonium citrate (0.3), $(NH_4)_2SO_4$ (3.2) yeast extract (5) solution of trace elements (1 ml) and pH adjusted to 6.8.

The solution of trace elements contained (g/L) citric acid. $H_2O$ (4.0), $MnSO_4$. $H_2O$ (3.0), NaCl (1.0), $FeSO_4.7H_2O$ (0.10), $CoCL_2.6H_2O$ (0.10), $ZnSO_4.7H_2O$ (0.10), $CuSO_4.5H_2O$ (0.01), $H_3BO_3$ (0.01) and $Na_3MoO_4.2H_2O$ (0.01)

The fermentation was analyzed for cell density by determining the optical density (OD) of the culture at 600 nM in a spectrophotometer and glycerol and 1,3-propanediol concentrations were determined using HPLC.

Isolation and Identification of 1,3-propanediol:

The conversion of glucose to glycerol and 1,3-propanediol was monitored by HPLC. Analyses were performed using standard techniques and materials available to one of skill in the art of chromatography. One suitable method utilized a Waters Alliance HPLC system using RI detection. Samples were injected onto a Aminex HPX87H column (7.8 mm×300 mm, BioRad, Hercules, Calif.) equipped with a Cation H Refill Cartridge precolumn (4.6 mm×30 mm, Biorad, Hercules, Calif.), temperature controlled at 50° C., using 5 mM $H_2SO_4$ as mobile phase at a flow rate of 0.4 ml/min. The system was calibrated weekly against known concentration standards. Typically, the retention times of glucose, glycerol, 1,3-propanediol, and acetate were 12.7 min, 19.0 min, 25.2 min, and 21.5 min, respectively.

In this example, two systems were compared. In the first system, the trc promoter was integrated into the galP target site (galP locus-see example 1E) allowing the *E. coli* strain to produce glucokinase under the natural regulation of glk and in the second system, the trc promoter was integrated into both the galP target site and the glk target site (glk loci—see example 1F). FIGS. 10 and 11 illustrate the fermentation results for KLpts7/pMCGG and KLgalP-ptrc transformed with pSYCO101 and pSYCO103, respectively.

The plasmid encoded glucose transport system in KLpts7/pMCGG allowed the strain to grow to high cell density (FIG. 10A) and produce glycerol and 1,3-propanediol (FIG. 10B). However, the amount of glycerol and 1,3-propanediol produced relative to the cell mass was low approx 7 g/L of 1,3 propanediol for an $OD_{600}$ of 194. In contrast, as shown in FIG. 11, KlgalP-ptrc produced much less cell mass in the fermentation and more product approx. 61 g/L 1,3-propanediol and 36 g/L glycerol (FIG. 11B) for an $OD_{600}$ of 70 (FIG. 11A).

By constitutively expressing galP on the chromosome from the trc promoter the flux of carbon from glucose was increased into the pathway for the desired products, glycerol and 1,3-propanediol rather than into pathways to produce cell mass.

Example 3

Constitutive Expression of galP and glk from the Chromosome of a PTS⁻ Strain

The PTS⁻/Glu⁻ strain, KLpts7 was made Glu⁺ by integration of the trc promoter at the galP and glk target sites to create strain KLGG and reference is made to example 1 above. The strain was transformed by standard procedures with pSYCO101. The production of cell mass, glycerol and 1,3-propanediol was tested in a standard fermentation (see example 2).

As illustrated in FIGS. 11 and 12, in comparison to KlgalP-trc, KLGG grew more rapidly (at T 33.9, KLGG had obtained an $OD_{600}$ of 24.7 while the $OD_{600}$ of KlgalP was 19.6). KLGG produced 70 g/L of 1,3-propanediol compared with 61 g/L produced by strain KlgalP-trc. Additionally, the peak concentration was reached earlier in the KLGG fermentation (56.8 h compared to 62.7 hours for KlgalP). The constitutive expression of galP and glk by chromosomal integration of the trc promoter therefore produces more 1,3-propanediol in less fermentation time than the constitutive expression of only galP.

Example 4

Selection and Analysis of a Fast Growing PTS⁻/Glu⁺ Strain of *E. coli*

The long lag phase in growth while producing glycerol and 1,3-propanediol demonstrated in fermentation studies of the strain KLGG (in example 3 above) was repeatable in shake flask experiments as shown in table 2 below for KLGG at 24 and 48 hours

TABLE 2

| Strain | Time (h) | OD 600 | Glucose Consumed (g/L) | Glycerol (g/L) | 1,3-propanediol | Molar Yield |
|---|---|---|---|---|---|---|
| KLGG | 24 | 6 | 5.5 | 2.6 | 1.5 | 1.6 |
| KLGG | 48 | 20 | 21 | 9.9 | 2.7 | 1.2 |
| FMP | 16 | 16.5 | 24.6 | 9.2 | 3.2 | 1.1 |

Molar yield is (moles glycerol + moles 1,3-propanediol/mole glucose consumed

To decrease the fermentation time a fast growing variant of KLGG was selected by growing KLGG in a fermentor in TM2 and glucose excess conditions at 35° C. pH 6.8. Cells were harvested at early log phase (for example see T31 in FIG. 12A) and plated for isolated colonies on L agar. Isolated colonies were screened for variants which produced glycerol and 1,3-propanediol when transformed with pSYCO at concentrations equivalent to KLGG. A variant was identified and designated FMP. FMP exhibited a performance equivalent to KLGG but accomplished the same performance in 16 h of shake flask growth compared to 48 h for KLGG (table 2).

Shake flasks experiments were done in TM2 with 2% glucose+spectinomycin at a concentration of 50 microgram/ml and $B_{12}$ at 2 milligram/liter. An overnight culture of the strain with the pSYCO plasmid was grown in LB+spectinomycin (50 microgram/ml) at 37° C. with shaking at 200 rpm. The shake flasks were inoculated with 200 microliters of the overnight culture (10 mls of culture in 250 ml baffled flask) and grown at 34° C. with shaking at 200 rpm. The cultures were analyzed for cell density ($OD_{600}$) and consumption of glucose and production of glycerol and 1,3-propanediol by HPLC. (Reference is made to example 2).

Analysis of the fast growing variant:: The FMP variant was analyzed for glucokinase activity, relative levels of glk mRNA and the gene and promoter sequence. As shown in table 3 the glucokinase activity of FMP was increased 3 fold over that of KLGG, from 0.08 units to 0.22 units. This suggests either a mutation in the coding region resulting in a more active enzyme or an increase in the amount of enzyme present.

TABLE 3

| STRAIN | Glucokinase activity (micromoles/min, mg protein in 1.0 mL) |
|---|---|
| KLGG | 0.083074232 |
| FMP | 0.218672457 |

To test the expression levels, the relative levels of glk mRNA was determined and reference is made to Table 4A and 4B. Using a light cycler, data is generated in the form of crossing times. The lower the crossing time, the more mRNA is present. The crossing times for galP were equivalent in KLGG and FMP indicating similar levels of mRNA in both strains. The crossing times of glk in FMP was lower than that of KLGG (15.7 compared to 18.47, respectively) and the ratio of the average crossing times was 1.18 (KLGG-g/k:FMP-g/k), which indicated that more glk mRNA was present in the FMP strain. Samples were tested in duplicate (1 or 2) and the average (Avg.) was taken. Averages were used to determine the ratios (glk-K/glk-F represents KLGG glk and FMP glk, respectively).

TABLE 4A

| | | | Crossing Time | | | | | | |
|---|---|---|---|---|---|---|---|---|---|
| Strain | galP1 | galP2 | galP Avg | glk1 | glk2 | glk Avg | rrsH1 | rrsH2 | rrsH Avg |
| KLGG | 18.48 | 18.42 | 18.45 | 18.47 | 18.46 | 18.47 | 11.64 | 11.67 | 11.66 |
| FMP | 17.75 | 17.72 | 17.74 | 15.69 | 15.7 | 15.7 | 11.7 | 11.7 | 11.7 |

TABLE 4B

| | | | Ratios | | |
|---|---|---|---|---|---|
| Strain | rrsH Avg./ galP Avg. | rrsH Avg./ glk Avg. | galP-K Avg./ glk-F Avg. | galP-K'/ galP-F' | glk-K/ glk-F |
| KLGG | 0.63 | 0.63 | 1.0 | 1.04 | 1.18 |
| FMP | 0.66 | 0.75 | 0.88 | | |

Sequence analysis was done on the KLGG and FMP glk gene and the trc promoter. No mutations were found in the glk coding sequence of FMP. The sequence of the trc promoter was determined by amplification by PCR from the chromosome of KLGG and FMP using glkB1/glkBC11 primers. Sequencing was also performed using the primer TrcF (SEQ ID NO. 14) 5' GCTGTGCAGGTCGTAAATCACTGCATAATT 3'
A single mutation from G to A was identified in the lac operator of the trc promoter in FMP as indicated below.
TGGAATTGTGAGCGGATAACAATT: wild type lac operator (KLGG) (SEQ ID NO. 15)
TGGAATTGTGAACGGATAACAATT: lac operator (FMP) (SEQ ID NO. 16)
This mutation has been previously described (THE OPERON, Miller, J H and Reznikoff, W S eds., 1980, p190-192 and references therein) as one of the $O^c$ operator constitutive mutations which increases expression of the linked gene(s) and decreases the affinity of the operator for the lac repressor. This effectively would increase the transcription of glk from the promoter and this was demonstrated by the increase in enzyme activity. The variant strain grows faster because there is more glucokinase to phosphorylate the incoming glucose and more G-6-P will be delivered into central metabolism.
Assays for Glucokinase Were Done Under the Following Conditions:
100 mM Phosphate Buffer pH 7.2, 5 mM $MgCl_2$, 500 mM NADP, 5 mM ATP, 2 Units of Glucose-6-Phosphate Dehydrogenase. This assay detects the conversion of glucose and ATP to glucose-6-phosphate by monitoring the appearance of $NADPH_2$ in the following scheme:

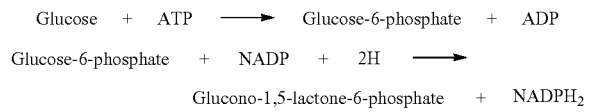

Light Cycler Determination of relative levels of mRNA of galP, glk and the 16S rRNA gene (rrsH) as a control in shake flask experiments.—The strains KLGG and FMP were grown in 10 mls of TM2+2% glucose to an $OD_{600}$ of 20. The cultures were poured directly into liquid nitrogen in a 50 ml conical tube and RNA was purified as described below. The following primers were used:

```
For galP
GalP-R1
5' GTGTCTTCTTCCTGCCAGAC 3'      (SEQ ID NO. 17)

GalP-F1
5' CCTGCAACAGTACGCCAAG 3'       (SEQ ID NO. 18)

For gLk
Glk-R1
5' CATCTGGTCCATGTCGATAAGC 3'    (SEQ ID NO. 19)

Glk-F1
5' GCGGTTGTCAGCTTTCACAA 3'      (SEQ ID NO. 20)

For rrsH
rrsH-F1
5' AGCTGGTCTGAGAGGATG 3'        (SEQ ID NO. 21)

rrsH-R1
5' AATTCCGATTAACGCTTGC 3'       (SE ID NO. 22)
```

The light cycler reactions were made according to the manufacturer's protocol using Lightcycler RNA Amplification Kit SYBR Green I (Roche) adjusted for 10 µl reactions. A total of 500 ng of RNA were used per reaction. The program used was: target temperature 55° C.; incubation time 10 min., and temperature transition rate 20° C./sec.

The RNA isolation procedure included growing a strain in a shake flask under appropriate conditions as specified in example 4 above and harvesting by pipeting 7 to 10 mls directly into liquid nitrogen in 50 ml conical tubes. The samples were frozen at −70° C. until ready for use. In general, standard procedures were used for RNA isolation with the following initial adjustments: 50 ml tubes of frozen sample were placed in a dry ice bucket; 15 ml of phenol:chloroform (1:1) and 1.5 ml of 3M NaOAc pH 4.8 were added to each 50 ml tube; a small amount of the frozen sample (ca 500 to 2000 µl of broth) was added to a pre-chilled (with dry ice) coffee grinder; additional dry ice (2 or 3 small pieces) was added to the coffee grinder and samples were ground for at least 1 min; the grinder was tapped to get all material into the grinder cap, and the cap, which contained the frozen ground cell broth and residual dry ice, was removed; an equal amount of 2×RNA extraction buffer was quickly pipetted into the cap; frozen material was stirred into a slurry using a disposable sterile loop and then placed into conical tubes containing 15 ml phenol:chloroform/NaOAc; mixed and placed on ice. Standard procedures known in the art were then followed. (Sambrook et al., supra).

The invention claimed is:

1. A method of increasing carbon flow into a metabolic pathway of a PTS⁻/Glu⁻ bacterial host cell originally capable of utilizing a phosphotransferase transport system (PTS) for carbohydrate transport comprising,
  a) modifying an endogenous chromosomal regulatory region which is operably linked to a nucleic acid encoding a glucose assimilation protein in a PTS⁻/Glu⁻ host cell by transforming the PTS⁻/Glu⁻ host cell with a DNA construct comprising a promoter and DNA flanking sequences corresponding to upstream (5') regions of the glucose assimilation protein;
  b) allowing integration of the DNA construct to restore a Glu+ phenotype; and
  c) culturing the transformed host cell under suitable culture conditions,
  wherein carbon flow into a metabolic pathway of the transformed host cell is increased compared to carbon flow into the corresponding metabolic pathway in a PTS bacterial host cell cultured under essentially the same culture conditions.

2. The method according to claim 1, wherein the promoter is a non-host cell promoter.

3. The method according to claim 1, wherein the promoter is a modified endogenous promoter.

4. The method according to claim 1, wherein the glucose assimilation protein is a glucose transporter.

5. The method according to claim 4, wherein the glucose transporter is a galactose permease obtained from *E. coli* or a glucose transporter having at least 80% sequence identity thereto.

6. The method according to claim 1, wherein the glucose assimilation protein is a phosphorylating protein.

7. The method according to claim 6, wherein the phosphorylating protein is a glucokinase.

8. The method according to claim 5, further comprising modifying an endogenous chromosomal regulatory region which is operably linked to a nucleic acid encoding a glucokinase in the PTS⁻/Glu⁻ host cell by transforming the PTS⁻/Glu⁻ host cell with a second DNA construct comprising a promoter and DNA flanking sequences corresponding to upstream (5') regions of the glucokinase.

9. The method of claim 1, wherein the bacterial host cell is selected from the group consisting of *E. coli* cells, *Bacillus* cells and *Pantoea* cells.

10. The method according to claim 1, wherein the PTS⁻/Glu⁻ host cell is obtained from a PTS cell by deletion of one or more genes selected from the group consisting of ptsI, ptsH and crr.

11. The method according to claim 1, further comprising transforming the PTS⁻/Glu⁺ host cell with a polynucleotide encoding a protein selected from the group consisting of a transketolase, a transaldolase, and a phosphoenolpyruvate synthase.

12. The method according to claim 1, further comprising transforming the PTS⁻/Glu⁺ host cell with a polynucleotide encoding at least one enzyme selected from the group consisting of DAHP synthase, DHQ synthase, DHQ dehydratase, shikimate dehydrogenase, shikimate kinase EPSP synthase and chorismate synthase.

13. A bacterial cell, wherein the bacterial cell has increased carbon flow into a metabolic pathway, comprising:
a PTS⁻ bacterial cell incapable of utilizing a phosphotransferase transport system (PTS) for carbohydrate transport, whererin the PTS⁻ bacterial cell comprises a modified endogenous chromosomal regulatory region which is operably linked to a nucleic acid that encodes a glucose assimilation protein,
wherein carbon flow into the metabolic pathway is increased compared to carbon flow into the corresponding metabolic pathway in a PTS bacterial cell cultured under essentially the same culture conditions.

14. A method of increasing carbon flow into a metabolic pathway of a PTS⁻/Glu⁻ bacterial host cell originally capable of utilizing a phosphotransferase transport system (PTS) for carbohydrate transport comprising,
a) modifying an endogenous chromosomal regulatory region which is operably linked to a nucleic acid encoding a galactose permease in a PTS⁻/Glu⁻ host cell by transforming the PTS⁻/Glu⁻ host cell with a first DNA construct comprising a promoter and DNA flanking sequences corresponding to upstream (5') regions of the galactose permease;
b) modifying an endogenous chromosomal regulatory region which is operably linked to a nucleic acid encoding a glucokinase in the PTS⁻/Glu⁻ host cell by transforming the PTS⁻/Glu⁻ host cell with a second DNA construct comprising a promoter and DNA flanking sequences corresponding to upstream (5') regions of the glucokinase;
c) allowing integration of the first and the second DNA constructs, wherein the first DNA construct replaces an endogenous promoter of the nucleic acid encoding the galactose permease and the second DNA construct replaces an endogenous promoter of the nucleic acid encoding the glucokinase wherein both the galactose permease and the glucokinase are expressed in the host cell and wherein said expression results in an increase in carbon flow into a metabolic pathway of the transformed host cell compared to carbon flow into the corresponding metabolic pathway in an unaltered PTS⁻/Glu⁻ bacterial cell.

15. The method according to claim 14, wherein the bacterial host cell is selected from the group consisting of *E. coli* cells, *Bacillus* cells and *Pantoea* cells.

16. The method according to claim 14, wherein the metabolic pathway is the common aromatic pathway.

17. The method according to claim 14, further comprising transforming the PTS⁻/Glu⁻ host cell with a polynucleotide encoding a protein selected from the group consisting of a transketolase, a transaldolase and a phosphoenolpyruvate synthase.

18. A method for increasing the growth rate of a PTS⁻/Glu⁻ bacterial host cell originally capable of utilizing a phosphotransferase transport system (PTS) for carbohydrate transport comprising,
a) modifying an endogenous chromosomal regulatory region which is operably linked to a nucleic acid encoding a galactose permease in a PTS⁻/Glu⁻ host cell by transforming the PTS⁻/Glu⁻ host cell with a first DNA construct comprising an exogenous promoter and DNA flanking sequences corresponding to (5') upstream region of the galactose permease;

b) modifying an endogenous regulatory region which is operably linked to a nucleic acid encoding a glucokinase in the PTS⁻/Glu⁻ host cell by transforming the PTS⁻/Glu⁻ host cell with a second DNA construct comprising an exogenous promoter and DNA flanking sequences corresponding to upstream (5') regions of the glucokinase;
c) allowing integration of the first and the second DNA constructs, wherein the first DNA construct replaces the endogenous promoter of the nucleic acid encoding the galactose permease and the second DNA construct replaces the endogenous promoter of the nucleic acid encoding the glucokinase;
d) culturing the transformed bacterial host cell under suitable conditions; and
e) allowing expression of the galactose permease and the glucokinase from the modified regulatory regions to obtain an altered bacterial cell having an increased specific growth rate compared to the specific growth rate of a corresponding unaltered PTS bacterial host cell cultured under essentially the same culture conditions.

19. A bacterial cell, wherein the bacterial cell has an increased growth rate, comprising:
a) a PTS⁻ bacterial cell incapable of utilizing a phosphotransferase transport system (PTS) for carbohydrate transport,
b) a modified endogenous chromosomal regulatory region which is operably linked to a nucleic acid that encodes a galactose permease, and
c) a modified endogenous chromosomal regulatory region which is operably linked to a nucleic acid that encodes a glucokinase,
wherein the growth rate is increased compared to the growth rate of a corresponding PTS bacterial cell cultured under essentially the same culture conditions.

20. The bacterial cell of claim 19, wherein said bacterial cell is a *Pantoea* cell.

21. The bacterial cell of claim 19, wherein said bacterial cell is an *E. coli* cell.

22. The method according to claim 18 further comprising transforming the selected bacterial host cell with a polynucleotide encoding a protein selected from the group consisting of a transketolase, a transaldolase and a phosphoenolpyruvate synthase.

23. The cell according to claim 13, wherein the modified regulatory region is a non-host cell promoter.

24. The cell according to claim 13, wherein the modified regulatory region is a modified endogenous promoter.

25. The cell according to claim 13, wherein the glucose assimilation protein is a glucose transporter.

26. The cell according to claim 25, wherein the glucose transporter is a galactose permease obtained from *E. coli* or a glucose transporter having at least 80% sequence identity thereto.

27. The cell according to claim 13, wherein the glucose assimilation protein is a phosphorylating protein.

28. The cell according to claim 27, wherein the phosphorylating protein is a glucokinase.

29. The cell according to claim 25, further comprising a modified endogenous chromosomal regulatory region which is operably linked to a nucleic acid that encodes a glucokinase.

30. The cell according to claim 13, wherein the bacterial host cell is selected from the group consisting of *E. coli* cells, *Bacillus* cells and *Pantoea* cells.

31. The cell according to claim 13, wherein the PTS⁻ bacterial cell is obtained from a PTS cell by deletion of one or more genes selected from the group consisting of ptsI, ptsH and crr.

32. The cell according to claim 13, further comprising a polynucleotide that encodes a protein selected from the group consisting of a transketolase, a transaldolase, and a phosphoenolpyruvate synthase.

33. The cell according to claim 13, further comprising a polynucleotide that encodes at least one enzyme selected from the group consisting of DAHP synthase, DHQ synthase, DHQ dehydratase, shikimate dehydrogenase, shikimate kinase EPSP synthase and chorismate synthase.

34. The cell according to claim 19, wherein the modified regulatory region is a non-host cell promoter.

35. The cell according to claim 19, wherein the modified regulatory region is a modified endogenous promoter.

36. The cell according to claim 19, wherein the glucose assimilation protein is a glucose transporter.

37. The cell according to claim 36, wherein the glucose transporter is a galactose permease obtained from *E. coli* or a glucose transporter having at least 80% sequence identity thereto.

38. The cell according to claim 19, wherein the glucose assimilation protein is a phosphorylating protein.

39. The cell according to claim 38, wherein the phosphorylating protein is a glucokinase.

40. The cell according to claim 37, further comprising a modified endogenous chromosomal regulatory region which is operably linked to a nucleic acid that encodes a glucokinase.

41. The cell according to claim 19, wherein the bacterial host cell is a *Bacillus* cell.

42. The cell according to claim 19, wherein the PTS⁻ bacterial cell is obtained from a PTS cell by deletion of one or more genes selected from the group consisting of ptsI, ptsH and crr.

43. The cell according to claim 19, further comprising a polynucleotide that encodes a protein selected from the group consisting of a transketolase, a transaldolase, and a phosphoenolpyruvate synthase.

44. The cell according to claim 19, further comprising a polynucleotide that encodes at least one enzyme selected from the group consisting of DAHP synthase, DHQ synthase, DHQ dehydratase, shikimate dehydrogenase, shikimate kinase EPSP synthase and chorismate synthase.

\* \* \* \* \*

SEQUENCE LISTING

```
<160> NUMBER OF SEQ ID NOS: 24

<210> SEQ ID NO 1
<211> LENGTH: 1350
<212> TYPE: DNA
<213> ORGANISM: Artificial Sequence
```

```
<220> FEATURE:
<223> OTHER INFORMATION: GalP-ptrc DNA cassette

<400> SEQUENCE: 1
tcggttttca cagttgttac atttcttttc agtaaagtct ggatgcatat ggcggccgca      60
taacttcgta tagcatacat tatacgaagt tatctagagt tgcatgcctg caggtccgaa     120
tttctgccat tcatccgctt attatcactt attcaggcgt agcaccaggc gtttaagggc     180
accaataact gccttaaaaa aattacgccc cgccctgcca ctcatcgcag tactgttgta     240
attcattaag cattctgccg acatggaagc catcacaaac ggcatgatga acctgaatcg     300
ccagcggcat cagcaccttg tcgccttgcg tataatattt gcccatggtg aaaacggggg     360
cgaagaagtt gtccatattg ccacgtttta atcaaaact ggtgaaactc acccagggat     420
tggctgagac gaaaaacata ttctcaataa accctttagg gaaataggcc aggttttcac     480
cgtaacacgc cacatcttgc gaatatatgt gtagaaactg ccggaaatcg tcgtggtatt     540
cactccagag cgatgaaaac gtttcagttt gctcatggaa aacggtgtaa caagggtgaa     600
cactatccca tatcaccagc tcaccgtctt tcattgccat acggaattcc ggatgagcat     660
tcatcaggcg ggcaagaatg tgaataaagg ccggataaaa cttgtgctta tttttctttta    720 cggtctttaa aaaggccgta atatccagct gaacggtctg gttataggta cattgagcaa     780
ctgactgaaa tgcctcaaaa tgttctttac gatgccattg gatatatca acggtggtat     840 atccagtgat tttttctcc attttagctt ccttagctcc tgaaaatctc gataactcaa      900
aaaatacgcc cggtagtgat cttatttcat tatggtgaaa gttggaacct cttacgtgcc     960
gatcaacgtc tcattttcgc caaaagttgg cccagggctt cccggtatca acagggacac    1020
caggatttat ttattctgcg aagtgatctt ccgtcacagg tatttattcg gactctagat    1080
aacttcgtat agcatacatt atacgaagtt atggatcatg gctgtgcagg tcgtaaatca    1140
ctgcataatt cgtgtcgctc aaggcgcact cccgttctgg ataatgtttt ttgcgccgac    1200
atcataacgg ttctggcaaa tattctgaaa tgagctgttg acaattaatc atccggctcg    1260
tataatgtgt ggaattgtga gcggataaca atttcacaca ggaaacagac taattcacaa    1320
taaaaaataa ccatattgga gggcatcatg                                    1350

<210> SEQ ID NO 2
<211> LENGTH: 364
<212> TYPE: DNA
<213> ORGANISM: Artificial Sequence
<220> FEATURE:
<223> OTHER INFORMATION: galP-trc DNA cassette after removal of CAT gene

<400> SEQUENCE: 2
cagcagtggt ggtgatcggt tttggctggg gccccctccc gcaccggagg ccgattacag      60
ccaaccacaa caggcaaagg gtttggaaga tattcatatt attattgcgg ttgtcacagt     120
tgttacattt cttttcagta aagtctggat gcatatggcg gccgcataac ttcgtatagc     180
atacattata cgaagttatg gatcatggct gtgcaggtcg taaatcactg cataattggt     240
gtcgctcaag gcgcactccc gttctggata atgtttttg cgccgacatc ataacggttc     300
tggcaaatat tctgaaatga gctgttgaca attaatcatc cggctcgtat aatgtgtggc     360
attg                                                                 364

<210> SEQ ID NO 3
<211> LENGTH: 1352
<212> TYPE: DNA
<213> ORGANISM: Artificial Sequence
```

<220> FEATURE:
<223> OTHER INFORMATION: glk-trc DNA cassette

<400> SEQUENCE: 3

| | | | | | |
|---|---|---|---|---|---|
| acttagtttg | cccagcttgc | aaaaaggcat | cgctgcaatt | ggatgcatat | ggcggccgca | 60 |
| taacttcgta | tagcatacat | tatacgaagt | tatctagagt | tgcatgcctg | caggtccgaa | 120 |
| tttctgccat | tcatccgctt | attatcactt | attcaggcgt | agcaccaggc | gtttaagggc | 180 |
| accaataact | gccttaaaaa | aattacgccc | cgccctgcca | ctcatcgcag | tactgttgta | 240 |
| attcattaag | cattctgccg | acatggaagc | catcacaaac | ggcatgatga | acctgaatcg | 300 |
| ccagcggcat | cagcaccttg | tcgccttgcg | tataatattt | gcccatggtg | aaaacggggg | 360 |
| cgaagaagtt | gtccatattg | gccacgttta | atcaaaact | ggtgaaactc | acccagggat | 420 |
| tggctgagac | gaaaaacata | ttctcaataa | acccttagg | gaataggcc | aggttttcac | 480 |
| cgtaacacgc | cacatcttgc | gaatatatgt | gtagaaactg | ccggaaatcg | tcgtggtatt | 540 |
| cactccgag | cgatgaaaac | gtttcagttt | gctcatggaa | acggtgtaa | caagggtgaa | 600 |
| cactatccca | tatccagc | tcaccgtctt | tcattgccat | acggaattcc | ggatgagcat | 660 |
| tcatcaggcg | ggcaagaatg | tgaataaagg | ccggataaaa | cttgtgctta | tttttctta | 720 |
| cggtctttaa | aaaggccgta | atatccagct | gaacggtctg | gttataggta | cattgagcaa | 780 |
| ctgactgaaa | tgcctcaaaa | tgttctttac | gatgccattg | gatatatca | acggtggtat | 840 |
| atccagtgat | tttttctcc | atttagctt | cctagctcc | tgaaaatctc | gataactcaa | 900 |
| aaaatacgcc | cggtagtgat | cttatttcat | tatggtgaaa | gttggaacct | cttacgtgcc | 960 |
| gatcaacgtc | tcattttcgc | caaaagttgg | cccagggctt | cccggtatca | acagggacac | 1020 |
| caggatttat | ttattctgcg | aagtgatctt | ccgtcacagg | tatttattcg | gactctagat | 1080 |
| aacttcgtat | agcatacatt | atacgaagtt | atggatcatg | gctgtgcagg | tcgtaaatca | 1140 |
| ctgcataatt | cgtgtcgctc | aaggcgcact | cccgttctgg | ataatgtttt | ttgcgccgac | 1200 |
| atcataacgg | ttctggcaaa | tattctgaaa | tgagctgctg | acaattaatc | atccggctcg | 1260 |
| tataatgtgt | ggaattgtga | gcggataaca | atttcacaca | ggaaacagac | gagaaagaat | 1320 |
| tattttgact | ttagcggagc | agttgaagaa | tg | | | 1352 |

<210> SEQ ID NO 4
<211> LENGTH: 13669
<212> TYPE: DNA
<213> ORGANISM: Artificial Sequence
<220> FEATURE:
<223> OTHER INFORMATION: pSYCO101 plasmid

<400> SEQUENCE: 4

| | | | | | |
|---|---|---|---|---|---|
| tagtaaagcc | ctcgctagat | tttaatgcgg | atgttgcgat | tacttcgcca | actattgcga | 60 |
| taacaagaaa | aagccagcct | ttcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |
| tccaactgat | ctgcgcgcga | ggccaagcga | tcttcttctt | gtccaagata | agcctgtcta | 360 |
| gcttcaagta | tgacgggctg | atactgggcc | ggcaggcgct | ccattgccca | gtcggcagcg | 420 |
| acatccttcg | gcgcgatttt | gccggttact | gcgctgtacc | aaatgcggga | caacgtaagc | 480 |
| actacatttc | gctcatcgcc | agcccagtcg | ggcggcgagt | tccatagcgt | taaggtttca | 540 |
| tttagcgcct | caaatagatc | ctgttcagga | accggatcaa | agagttcctc | cgccgctgga | 600 |

```
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt tgtttgttaa gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtattttt gtcaccattc   2520 atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttctttttg tgttagttct tttaataacc actcataaat cctcatagag   2820 tatttgttttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
```

```
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacctttt  3360 gctggaaaac ttgtaaattc tgctagaccc tctgtaaatt ccgctagacc tttgtgtgtt   3420 tttttttgttt atattcaagt ggttataatt tatagaataa agaaagaata aaaaagata   3480 aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg cctttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
```

```
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880 ttcaccttt gagccgatga acaatgaaaa gatcaaaacg atttgcagta ctggcccagc    5940
gccccgtcaa tcaggacggg ctgattggcg agtggcctga agagggctg atcgccatgg    6000 acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccgacccccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgc cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg gctattcgg    6720 agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagacttc tcccactcgg atattcgccg caccgcgcgc accctgatgc    6960
agatgctgcc gggcaccgac tttatttct ccggctacag cgcggtgccg aactacgaca    7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
```

```
gcattctgcg cacgtccgac gtctcctttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg catccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggagggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt    10020
ggaaagcctg ttcagtattc gtcacgagaa tggcgcggtg gagttctttc gggaagccct    10080
cagcccggcg gtgttcgcca aagtggtgta catcaaggag ggcgaactgg tgccgatcga    10140
taacgccagc ccgctggaaa aaattcgtct cgtgcgccgg caggcgaaag agaaagtgtt    10200
```

```
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380 gccgcgcaat gcggtcgcca ccgggctgct actggccggt caggcgaatt aaacgggcgc   10440
tcgcgccagc tctaggtac aaataaaaaa ggcacgtcag atgacgtgcc ttttttcttg    10500
tctagagtac tggcgaaagg gggatgtgct gcaaggcgat taagttgggt aacgccaggg   10560
ttttcccagt cacgacgttg taaaacgacg ccagtgaat tcgagctcgg tacccggggc    10620
ggccgcgcta gcgcccgatc cagctggagt ttgtagaaac gcaaaaggc catccgtcag    10680 gatggccttc tgcttaattt gatgcctggc agtttatggc gggcgtcctg cccgccaccc   10740
tccgggccgt tgcttcgcaa cgttcaaatc cgctcccggc ggatttgtcc tactcaggag   10800
agcgttcacc gacaaacaac agataaaacg aaaggcccag tctttcgact gagcctttcg   10860
ttttatttga tgcctggcag ttccctactc tcgcatgggg agaccccaca ctaccatcgg   10920
cgctacggcg tttcacttct gagttcggca tggggtcagg tgggaccacc gcgctactgc   10980
cgccaggcaa attctgtttt atcagaccgc ttctgcgttc tgatttaatc tgtatcaggc   11040
tgaaaatctt ctctcatccg ccaaaacagc caagcttgca tgcctgcagc ccgggttacc   11100
atttcaacag atcgtcctta gcatataagt agtcgtcaaa aatgaattca acttcgtctg   11160
tttcggcatt gtagccgcca actctgatgg attcgtggtt tttgacaatg atgtcacagc   11220 cttttttcctt taggaagtcc aagtcgaaag tagtggcaat accaatgatc ttacaaccgg   11280
cggcttttcc ggcggcaata cctgctggag cgtcttcaaa tactactacc ttagatttgg   11340
aagggtcttg ctcattgatc ggatatccta agccattcct gccttcaga tatggttctg    11400 gatgaggctt accctgtttg acatcattag cggtaatgaa gtactttggt ctcctgattc   11460
ccagatgctc gaaccatttt tgtgccatat cacgggtacc ggaagttgcc acagcccatt   11520 tctctttttgg tagagcgttc aaagcgttgc acagcttaac tgcacctggg acttcaatgg   11580 attttttcacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttctagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gccacatgtt   12000
tccaaccatt cgtgaacttc tttgcaggta attaaacctt gagcggattg gccattcaac   12060
aactcctttt cacattccca ggcgtcctta ccagaagtag ccattagcct agcaaccttg   12120
acgtttctac caccagcgca ggtggtgatc aaatcagcaa caccagcaga ctcttggtag   12180
tatgtttctt ctctagattc tgggaaaaac atttgaccga atctgatgat ctcacccaaa   12240
ccgactcttt ggatggcagc agaagcgttg ttacccagc ctagaccttc gacgaaacca    12300
caacctaagg caacaacgtt cttcaaagca ccacagatgg agataccagc aacatcttcg   12360
atgacactaa cgtggaagta aggtctgtgg aacaaggcct ttagaacctt atggtcgacg   12420
tccttgccct cgcctctgaa atcctttgga atgtggtaag caactgttgt tcagaccag    12480 tgttcttgag cgacttcggt ggcaatgtta gcaccagata gagcaccaca ttgaatacct   12540
agttcctcag tgatgtaaga ggatagcaat tggacacctt tagcaccaac ttcaaaaccc   12600
```

```
tttagacagg agatagctct gacgtgtgaa tcaacatgac ctttcaattg gctacagata   12660
cggggcaaaa attgatgtgg aatgttgaaa acgatgatgt cgacatcctt gactgaatca   12720
atcaagtctg gattagcaac caaattgtcg ggtagagtga tgccaggcaa gtatttcacg   12780
ttttgatgtc tagtatttat gatttcagtc aattttttcac cattgatctc ttcttcgaac   12840
acccacattt gtactattgg agcgaaaact tctgggtatc ccttacaatt ttcggcaacc   12900
accttggcaa tagtagtacc ccagttacca gatccaatca cagtaacctt gaaaggcttt   12960
tcggcagcct tcaaagaaac agaagaggaa cttctctttc taccagcatt caagtggccg   13020
gaagttaagt ttaatctatc agcagcagca gccatggaat tgtcctcctt actagtcatg   13080
gtctgtttcc tgtgtgaaat tgttatccgc tcacaattcc acacattata cgagccggat   13140
gattaattgt caacagctca tttcagaata tttgccagaa ccgttatgat gtcggcgcaa   13200
aaaacattat ccagaacggg agtgcgcctt gagcgacacg aattatgcag tgatttacga   13260
cctgcacagc cataccacag cttccgatgg ctgcctgacg ccagaagcat tggtgcacgc   13320
tagccagtac atttaaatgg taccctctag tcaaggcctt aagtgagtcg tattacggac   13380
tggccgtcgt tttacaacgt cgtgactggg aaaaccctgg cgttacccaa cttaatcgcc   13440
ttgcagcaca tcccccttc gccagctggc gtaatagcga agaggcccgc accgatcgcc   13500
cttcccaaca gttgcgcagc ctgaatggcg aatggcgcct gatgcggtat tttctcctta   13560
cgcatctgtg cggtatttca caccgcatat ggtgcactct cagtacaatc tgctctgatg   13620
ccgcatagtt aagccagccc cgacacccgc caacacccgc tgacgagct               13669
```

<210> SEQ ID NO 5
<211> LENGTH: 44
<212> TYPE: DNA
<213> ORGANISM: Artificial Sequence
<220> FEATURE:
<223> OTHER INFORMATION: promoter

<400> SEQUENCE: 5

```
cgagccgtca cgcccttgac aatgccacat cctgagcaaa taat             44
```

<210> SEQ ID NO 6
<211> LENGTH: 61
<212> TYPE: DNA
<213> ORGANISM: Artificial Sequence
<220> FEATURE:
<223> OTHER INFORMATION: primer

<400> SEQUENCE: 6

```
tcggttttca cagttgttac atttcttttc agtaaagtct ggatgcatat ggcggccgca   60
t                                                                    61
```

<210> SEQ ID NO 7
<211> LENGTH: 65
<212> TYPE: DNA
<213> ORGANISM: Artificial Sequence
<220> FEATURE:
<223> OTHER INFORMATION: primer

<400> SEQUENCE: 7

```
catgatgccc tccaatatgg ttatttttta ttgtgaatta gtctgtttcc tgtgtgaaat   60
tgtta                                                                65
```

<210> SEQ ID NO 8
<211> LENGTH: 60

```
<212> TYPE: DNA
<213> ORGANISM: Artificial Sequence
<220> FEATURE:
<223> OTHER INFORMATION: primer

<400> SEQUENCE: 8
acttagtttg cccagcttgc aaaaggcatc gctgcaattg gatgcatatg gcggccgcat      60

<210> SEQ ID NO 9
<211> LENGTH: 67
<212> TYPE: DNA
<213> ORGANISM: Artificial Sequence
<220> FEATURE:
<223> OTHER INFORMATION: primer

<400> SEQUENCE: 9
cattcttcaa ctgctccgct aaagtcaaaa taattctttc tcgtctgttt cctgtgtgaa      60
attgtta                                                                67

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
actttggtcg tgaacatttc ccgtgggaaa                                        30

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
agaaagataa gcaccgagga tcccgata                                          28

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
aacaggagtg ccaaacagtg cgccga                                            26

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ctattcggcg caaaatcaac gtgaccgcct                                        30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
```

```
gctgtgcagg tcgtaaatca ctgcataatt                                        30

<210> SEQ ID NO 15
<211> LENGTH: 24
<212> TYPE: DNA
<213> ORGANISM: Unknown
<220> FEATURE:
<223> OTHER INFORMATION: wild type lac operator

<400> SEQUENCE: 15
tggaattgtg agcggataac aatt                                              24

<210> SEQ ID NO 16
<211> LENGTH: 24
<212> TYPE: DNA
<213> ORGANISM: Artificial Sequence
<220> FEATURE:
<223> OTHER INFORMATION: mutated lac operator

<400> SEQUENCE: 16
tggaattgtg aacggataac aatt                                              24

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gtgtcttctt cctgccagac                                                   20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
cctgcaacag tacgccaag                                                    19

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
catctggtcc atgtcgataa gc                                                22

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gcggttgtca gctttcacaa                                                   20

<210> SEQ ID NO 21
<211> LENGTH: 18
<212> TYPE: DNA
<213> ORGANISM: Artificial Sequence
```

```
<220> FEATURE:
<223> OTHER INFORMATION: primer

<400> SEQUENCE: 21
agctggtctg agaggatg                                                    18

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
aattccgatt aacgcttgc                                                   19

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
agaattgcaa cagtaatgcc agcttgttaa aaatgcgta                             39

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
cctgttttgt gctcagctca tcagtggctt gctgaa                                36
```